United States Patent
Way et al.

(10) Patent No.: US 10,538,566 B2
(45) Date of Patent: *Jan. 21, 2020

(54) FUSION PROTEINS FOR TREATING CANCER AND RELATED METHODS

(71) Applicant: President and Fellows of Harvard College, Cambridge, MA (US)

(72) Inventors: Jeffrey Charles Way, Cambridge, MA (US); Avram Lev Robinson-Mosher, Cambridge, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/376,216

(22) Filed: Apr. 5, 2019

(65) Prior Publication Data

US 2019/0233492 A1   Aug. 1, 2019

Related U.S. Application Data

(63) Continuation of application No. 15/307,646, filed as application No. PCT/US2015/028653 on Apr. 30, 2015, now Pat. No. 10,308,697.

(60) Provisional application No. 61/986,866, filed on Apr. 30, 2014.

(51) Int. Cl.
| | |
|---|---|
| *C07K 14/56* | (2006.01) |
| *C07K 16/28* | (2006.01) |
| *A61K 38/21* | (2006.01) |
| *A61K 39/395* | (2006.01) |
| *C07K 16/32* | (2006.01) |
| *A61K 39/00* | (2006.01) |
| *A61K 45/06* | (2006.01) |

(52) U.S. Cl.
CPC ............ *C07K 14/56* (2013.01); *A61K 38/212* (2013.01); *A61K 39/39558* (2013.01); *A61K 45/06* (2013.01); *C07K 16/2863* (2013.01); *C07K 16/32* (2013.01); *A61K 2039/505* (2013.01); *C07K 2317/34* (2013.01); *C07K 2317/56* (2013.01); *C07K 2317/73* (2013.01); *C07K 2319/00* (2013.01); *C07K 2319/01* (2013.01)

(58) Field of Classification Search
CPC .... C07K 14/56; C07K 16/32; C07K 16/2863; C07K 2317/56; C07K 2319/00; C07K 2319/01; A61K 38/212; A61K 39/39558; A61K 2039/505
See application file for complete search history.

(56) References Cited

U.S. PATENT DOCUMENTS

| | | |
|---|---|---|
| 5,606,023 A | 2/1997 | Chen et al. |
| 5,652,353 A | 7/1997 | Fiers et al. |
| 6,787,133 B2 | 9/2004 | Weinrich et al. |
| 7,186,804 B2 | 3/2007 | Gillies et al. |
| 7,294,472 B2 | 11/2007 | Gilchrist et al. |
| 2002/0102257 A1 | 8/2002 | Johnson |
| 2003/0026779 A1 | 2/2003 | Yu et al. |
| 2003/0138401 A1 | 7/2003 | Dahiyat et al. |
| 2003/0166163 A1 | 9/2003 | Gillies |
| 2005/0036951 A1 | 2/2005 | Henderson |
| 2005/0089888 A1 | 4/2005 | Shaw et al. |
| 2006/0263368 A1 | 11/2006 | Rosenblum et al. |
| 2008/0171363 A1 | 7/2008 | Patten et al. |
| 2008/0214436 A1 | 9/2008 | Yu et al. |
| 2008/0279823 A1 | 11/2008 | Schreiber et al. |
| 2009/0238789 A1 | 9/2009 | Guyon et al. |
| 2010/0003266 A1 | 1/2010 | Simon |
| 2011/0274658 A1 | 11/2011 | Silver et al. |
| 2012/0178139 A1 | 7/2012 | Hubbell et al. |
| 2012/0288477 A1 | 11/2012 | Wang |
| 2012/0302733 A1 | 11/2012 | Padgett et al. |
| 2013/0230517 A1 | 9/2013 | Grewal et al. |
| 2013/0295004 A1 | 11/2013 | Hsieh et al. |
| 2014/0030222 A1 | 1/2014 | Kuo et al. |
| 2014/0121123 A1 | 5/2014 | Wang et al. |

FOREIGN PATENT DOCUMENTS

| | | |
|---|---|---|
| WO | 1999/016889 A1 | 4/1999 |
| WO | 2001/062931 A2 | 8/2001 |
| WO | 2005/033134 A2 | 4/2005 |
| WO | 2006/074451 A2 | 7/2006 |
| WO | 2007/000769 A2 | 1/2007 |
| WO | 2007/089753 A2 | 8/2007 |
| WO | 2007/092537 A2 | 8/2007 |
| WO | 2008/124086 A2 | 10/2008 |
| WO | 2009/023270 A2 | 2/2009 |
| WO | 2009/039409 A2 | 3/2009 |
| WO | 2011/020783 A1 | 2/2011 |
| WO | 2011/069799 A1 | 6/2011 |
| WO | 2013/148871 A1 | 10/2013 |

OTHER PUBLICATIONS

Keppler et al. "A general method for the covalent labeling of fusion proteins with small molecules in vivo." Nature Biotechnology 21(1):86-89 (2003).
Keyt et al., "Identification of vascular endothelial growth factor determinants for binding KDR and FLT-1 receptors Generation of receptor-selective VEGF variants by site-directed mutagenesis." Journal of Biological Chemistry 271(10):5638-5646 (1996).

(Continued)

*Primary Examiner* — Ruixiang Li
(74) *Attorney, Agent, or Firm* — Nixon Peabody LLP; David S. Resnick; Nicole D. Kling

(57) ABSTRACT

Aspects of the disclosure provide fusion proteins that bind cells expressing one or more target molecules including, for example, one or more cell surface multisubunit signaling receptors (e.g., EGFRvIII-expressing cells that also express interferon receptors) and that induce anti-proliferative effects, and related compositions and methods for the treatment of cancer.

11 Claims, 9 Drawing Sheets

Specification includes a Sequence Listing.

(56) References Cited

OTHER PUBLICATIONS

Khuri "Weighing the hazards of erythropoiesis stimulation in patients with cancer." New England Journal of Medicine 356(24):2445-2448 (2007).
Knappik et al., "Fully synthetic human combinatorial antibody libraries (HuCAL) based on modular consensus frameworks and CDRs randomized with trinucleotides." Journal of Molecular Biology 296(1):57-86 (2000).
Kontos et al. "Engineering antigens for in situ erythrocyte binding induces T-cell deletion." PNAS 110(1):E60-E68 (2013).
Kontos et al., "Improving protein pharmacokinetics by engineering erythrocyte affinity." Molecular Pharmaceutics 7(6)2141-2147 (2010).
Kreitman et al., Handbook of Experimental Pharmacology. Chapter 5: Targeted Toxin Hybridproteins. 89-110 (1999).
Kuan et al. "Increased binding affinity enhances targeting of glioma xenografts by EGFRvIII-specific scFv." International Journal of Cancer 88(6):962-969 (2000).
Leyland-Jones et al., "Maintaining normal hemoglobin levels with epoetin alfa in mainly nonanemic patients with metastatic breast cancer receiving first-line chemotherapy: a survival study." Journal of Clinical Oncology 23(25):5960-5972 (2005).
Liu et al., "Growth factor receptor expression varies among high-grade gliomas and normal brain: epidermal growth factor receptor has excellent properties for interstitial fusion protein therapy." Molecular Cancer Therapeutics 2(8):783-787 (2003).
Lorberboum-Galski et al., "Cytotoxic activity of an interleukin 2-Pseudomonas exotoxin chimeric protein produced in *Escherichia coli*." PNAS 85(6):1922-1926 (1988).
Lyu et al., "The immunocytokine scFv23/TNF sensitizes HER-2/neu—overexpressing SKBR-3 cells to tumor necrosis factor (TNF) via up-regulation of TNF receptor-1." Molecular Cancer Therapeutics 4(8):1205-1213 (2005).
Marks et al. "By-Passing Immunization: Building High Affinity Human Antibodies by Chain Shuffling." Nature Biotechnology 10(7):779-783 (1992).
Masui et al. "Growth inhibition of human tumor cells in athymic mice by anti-epidermal growth factor receptor monoclonal antibodies." Cancer Research 44(3):1002-1007 (1984).
McKay et al., "Integrating signals from RTKs to ERK/MAPK." Oncogene 26(22):3113-3121 (2007).
Miguez "The role of asymmetric binding in ligand-receptor systems with 1: 2 interaction ratio." Biophysical Chemistry 148(1):74-81 (2010).
Modjtahedi et al. "Targeting of cells expressing wild-type EGFR and type-III mutant EGFR (EGFRvIII) by anti-EGFR MAb ICR62: A two-pronged attack for tumour therapy." International Journal of Cancer 105(2):273-280 (2003).
Murzin et al., "SCOP: a structural classification of proteins database for the investigation of sequences and structures." Journal of Molecular Biology 247(4):536-540 (1995).
Ogiso et al. "Crystal structure of the complex of human epidermal growth factor and receptor extracellular domains." Cell 110(6):775-787 (2002).
Pabo et al. "The lambda repressor contains two domains." PNAS 76(4):1608-1612 (1979).
Pai et al. "Antitumor activity of a transforming growth factor α-Pseudomonas exotoxin fusion protein (TGF-α-PE40)." Cancer Research 51(11):2808-2812 (1991).
Piehler et al., "Biophysical analysis of the interaction of human ifnar2 expressed in *E. coli* with IFNα2." Journal of Molecular Biology 289(1):57-67 (1999).
Piehler et al., "New structural and functional aspects of the type I interferon-receptor interaction revealed by comprehensive mutational analysis of the binding interface." Journal of Biological Chemistry 275(51):40425-40433 (2000).
Platanias "Mechanisms of type-I-and type-II-interferon-mediated signalling." Nature Reviews Immunology 5(5)375-386 (2005).
Powers et al. "Expression of single-chain Fv-Fc fusions in Pichia pastoris." Journal of Immunological Methods 251(1):123-135 (2001).

Quadt-Akabayov et al., "Determination of the human type I interferon receptor binding site on human interferon-α2 by cross saturation and an NMR-based model of the complex." Protein Science 15(11):2656-2668 (2006).
Reginato et al., "Integrins and EGFR coordinately regulate the pro-apoptotic protein Bim to prevent anoikis." Nature Cell Biology 5(8):733-740 (2003).
Robinson-Mosher et al., "Dynamics simulations for engineering macromolecular interactions." Chaos: An Interdisciplinary Journal of Nonlinear Science 23(2):025110 (2013).
Roisman et al., "Mutational analysis of the IFNAR1 binding site on IFNα2 reveals the architecture of a weak ligand-receptor binding-site." Journal of Molecular Biology 353(2):271-281 (2005).
Roisman et al., "Structure of the interferon-receptor complex determined by distance constraints from double-mutant cycles and flexible docking." PNAS 98(23):13231-13236 (2001).
Samel et al., "Generation of a FasL-based proapoptotic fusion protein devoid of systemic toxicity due to cell-surface antigen-restricted activation." Journal of Biological Chemistry 278(34):32077-32082 (2003).
Scherf et al., "Cytotoxic and antitumor activity of a recombinant tumor necrosis factor-B1 (Fv) fusion protein on LeY antigen-expressing human cancer cells." Clinical Cancer Research 2(9):1523-1531 (1996).
Schier et al. "Identification of functional and structural amino-acid residues by parsimonious mutagenesis." Gene 169(2):147-155 (1996).
Shockett et al. "A modified tetracycline-regulated system provides autoregulatory, inducible gene expression in cultured cells and transgenic mice." PNAS 92(14):6522-6526 (1995).
Siegall et al., "Cytotoxic activities of a fusion protein comprised of TGF alpha and Pseudomonas exotoxin." The FASEB Journal 3(14):2647-2652 (1989).
Singhal et al., "Antibody-mediated targeting of liposomes to red cells in vivo." FEBS Letters 201(2):321-326 (1986).
Snitkovsky et al., "A TVA-single-chain antibody fusion protein mediates specific targeting of a subgroup A avian leukosis virus vector to cells expressing a tumor-specific form of epidermal growth factor receptor." Journal of Virology 14(20):9540-9545 (2000).
Southcott et al., "The expression of human blood group antigens during erythropoiesis in a cell culture system." Blood 93(12):4425-4435 (1999).
Stauber et al., "Crystal structure of the IL-2 signaling complex: paradigm for a heterotrimeric cytokine receptor." PNAS 103(8):2788-2793 (2006).
Streuli et al., "Target cell specificity of two species of human interferon-alpha produced in *Escherichia coli* and of hybrid molecules derived from them." PNAS 78(5):2848-2852 (1981).
Taylor et al., "Anti-glycophorin single-chain Fv fusion to low-affinitymutant erythropoietin improves red blood cell-lineage specificity" Protein Engineering, Design & Selection 23(4):251-260 (2010).
Todhunter et al., "A bispecific immunotoxin (DTAT13) targeting human IL-13 receptor (IL-13R) and urokinase-type plasminogen activator receptor (uPAR) in a mouse xenograft model." Protein Engineering Design and Selection 17 (2):157-164 (2004).
Urlaub et al. "Isolation of Chinese hamster cell mutants deficient in dihydrofolate reductase activity." PNAS 77(7):4216-4220 (1980).
Wajant et al., "Differential activation of TRAIL-R1 and-2 by soluble and membrane TRAIL allows selective surface antigen-directed activation of TRAIL-R2 by a soluble TRAIL derivative." Oncogene 20(30):4101-4106 (2001).
Wasniowska et al., "Analysis of peptidic epitopes recognized by the three monoclonal antibodies specific for the same region of glycophorin A but showing different properties." Molecular Immunology 29(6):783-791 (1992).
Wright et al., "Randomized, double-blind, placebo-controlled trial of erythropoietin in non-small-cell lung cancer with disease-related anemia." Journal of Clinical Oncology 25(9):1027-1032 (2007).
Wüest et al., "TNF-Selectokine: a novel prodrug generated for tumor targeting and site-specific activation of tumor necrosis factor." Oncogene 21(27):4257-4265 (2002).

(56) References Cited

OTHER PUBLICATIONS

Yelton et al. "Affinity maturation of the BR96 anti-carcinoma antibody by codon-based mutagenesis." The Journal of Immunology 155(4):1994-2004 (1995).
Zhang et al. "Primary targeting of recombinant Fv-immunotoxin hscFv25-mTNFα against hepatocellular carcinoma." World Journal of Gastroenterology: WJG 10(13):1872-1875 (2004).
Zhang et al. "Site-directed mutational analysis of human tumor necrosis factor-alpha receptor binding site and structure-functional relationship." Journal of Biological Chemistry 267(33):24069-24075 (1992).
Adam et al. "Reduction of dimensionality in biological diffusion processes." Structural Chemistry and Molecular Biology 198:198-215 (1968).
Adamson et al. "Analysis of erythropoiesis by erythroid colony formation in culture." Blood Cells 4(1-2):89-103 (1977).
Ahmed et al. "Interferon [alpha] 2b gene delivery using adenoviral vector causes inhibition of tumor growth in xenograft models from a variety of cancers." Cancer Gene Therapy 8(10):788-795 (2001).
Assohou-Luty et al., "A CD40-CD95L fusion protein interferes with CD40L-induced prosurvival signaling and allows membrane CD40L-restricted activation of CD95." Journal of Molecular Medicine 84(9):785-797 (2006).
Bachoo et al. "Epidermal growth factor receptor and Ink4a/Arf: convergent mechanisms governing terminal differentiation and transformation along the neural stem cell to astrocyte axis." Cancer Cell 1(3):269-277 (2002).
Barbas et al. "In vitro evolution of a neutralizing human antibody to human immunodeficiency virus type 1 to enhance affinity and broaden strain cross-reactivity." PNAS 91(9):3809-3813 (1994).
Barker et al. "Effect of a chimeric anti-ganglioside GD2 antibody on cell-mediated lysis of human neuroblastoma cells." Cancer Research 51(1):144-149 (1991).
Bellot et al. "High-affinity epidermal growth factor binding is specifically reduced by a monoclonal antibody, and appears necessary for early responses." The Journal of Cell Biology 110(2) (1990): 491-502.
Blair et al. "HIV-1 entry—an expanding portal for drug discovery." Drug Discovery Today 5(5):183-194 (2000).
Boehm et al. "Structural models for carcinoembryonic antigen and its complex with the single-chain Fv antibody molecule MFE23." FEBS letters 475(1):11-16 (2000).
Bremer et al., "CD7-restricted activation of Fas-mediated apoptosis: a novel therapeutic approach for acute T-cell leukemia." Blood 107(7):2863-2870 (2006).
Bremer et al., "Simultaneous inhibition of epidermal growth factor receptor (EGFR) signaling and enhanced activation of tumor necrosis factor-related apoptosis-inducing ligand (TRAIL) receptor-mediated apoptosis induction by an scFv: sTRAIL fusion protein with specificity for human EGFR." Journal of Biological Chemistry 280 (11):10025-10033 (2005).
Bremer et al., "Target cell-restricted and-enhanced apoptosis induction by a scFv: sTRAIL fusion protein with specificity for the pancarcinoma-associated antigen EGP2." International Journal of Cancer 109(2):281-290 (2004).
Brown et al. "lac repressor can regulate expression from a hybrid SV40 early promoter containing a lac operator in animal cells." Cell 49(5):603-612 (1987).
Caraglia et al. "Interferon-induces apoptoais in human KB cells through a stress-dependent mitegen activated protein Kinase pathway that is antagonized by epidermal growth factor." Cell Death and Differentiation 6:773-780 (1999).
Catimel et al., "Kinetics of the autologous red cell agglutination test." Journal of immunological methods 165 (2):183-192 (1993).
Chan et al. "HIV entry and its inhibition." Cell 93(5):681-684 (1998).
Cho et al. "Structure of the extracellular region of HER2 alone and in complex with the Herceptin Fab." Nature 421(6924):756-760 (2003).
Cironi et al. "Enhancement of cell type specificity by quantitative modulation of a chimeric ligand." Journal of Biological Chemistry 283(13):8469-8476 (2008).
Clare et al. "Production of mouse epidermal growth factor in yeast: high-level secretion using Pichia pastoris strains containing multiple gene copies." Gene 105(2 ):205-212 (1991).
Crawford "Erythropoietin: high profile, high scrutiny." J Clin Oncol. 1021-1023 (2007).
Czerwinski et al. "Only selected light chains combine with a given heavy chain to confer specificity for a model glycopeptide antigen." The Journal of Immunology 160(9):4406-4417 (1998).
Daly et al. "Expression of heterologous proteins in Pichia pastoris: a useful experimental tool in protein engineering and production." Journal of Molecular Recognition 18(2):119-138 (2005).
Deller et al., "Crystal structure and functional dissection of the cytostatic cytokine oncostatin M." Structure 8 (8):863-874 (2000).
Eketjall et al., "Distinct structural elements in GDNF mediate binding to GFRα1 and activation of the GFRα1-c-Ret receptor complex." The EMBO journal 18(21):5901-5910 (1999).
Elliott et al. "Mapping of the active site of recombinant human erythropoietin." Blood 89(2) (1997): 493-502.
Evinger et al. "Assay of growth inhibition in lymphoblastoid cell cultures." Methods in enzymology 79:362-368 (1981).
Franklin et al., "Insights into ErbB signaling from the structure of the ErbB2-pertuzumab complex." Cancer Cell 5(4):317-328 (2004).
French et al., "Intracellular trafficking of epidermal growth factor family ligands is directly influenced by the pH sensitivity of the receptor/ligand interaction." Journal of Biological Chemistry 270(9):4334-4340 (1995).
Garcia et al. "High level expression of human IFN-alpha2b in Pichia pastoris." Biotecnologia Aplicada 12(3):152-155 (1995) Last accessed at http://www.bioline.org.br/request?ba95052 on Mar. 16, 2004.
Garcin et al. "High efficiency cell-specific targeting of cytokine activity" Nature Communications 5:3016 (2014).
Garrett et al., "Crystal structure of a truncated epidermal growth factor receptor extracellular domain bound to transforming growth factor α." Cell 110(6):763-773 (2002).
GenBank Accession No. AAK85297.1 Aug. 13, 2001. 1 page.
Giles et al., "Gemtuzumab ozogamicin in the treatment of acute myeloid leukemia." Cancer 98(10):2095-2104 (2003).
Gossen et al. "Tight control of gene expression in mammalian cells by tetracycline-responsive promoters." PNAS 89 (12):5547-5551 (1992).
Hass et al. "Preparation of synthetic polypeptide domains of carcinoembryonic antigen and their use in epitope mapping." Cancer Research 51(7):1876-1882 (1991).
Hawkins et al. "Selection of phage antibodies by binding affinity: mimicking affinity maturation." Journal of Molecular Biology 226(3):889-896 (1992).
Heimbrook et al. "Transforming growth factor alpha-Pseudomonas exotoxin fusion protein prolongs survival of nude mice bearing tumor xenografts." PNAS 87(12):4697-4701 (1990).
Henke et al. "Do erythropoietin receptors on cancer cells explain unexpected clinical findings?." Journal of Clinical Oncology 24(29):4708-4713 (2006).
Henke et al. "Erythropoietin to treat head and neck cancer patients with anaemia undergoing radiotherapy: randomised, double-blind, placebo-controlled trial." The Lancet 362(9392):1255-1260 (2003).
Hirankarn et al., "Genetic association of interferon-alpha subtypes 1, 2 and 5 in systemic lupus erythematosus." HLA 72(6):588-592 (2008).
Huang et al. "A trimeric anti-HER2/neu ScFv and tumor necrosis factor-α fusion protein induces HER2/neu signaling and facilitates repair of injured epithelia." Journal of Pharmacology and Experimental Therapeutics 318(3):983-991 (2006).
Huston et al. "Antigen recognition and targeted delivery by the single-chain Fv." Cell Biophysics 22(1-3)189-224 (1993).
Hymowitz et al., "A unique zinc-binding site revealed by a high-resolution X-ray structure of homotrimeric Apo2L/TRAIL." Biochemistry 39(4):633-640 (2000).
Jackson et al. "In vitro antibody maturation. Improvement of a high affinity, neutralizing antibody against IL-1 beta." The Journal of Immunology 154(7):3310-3319 (1995).

(56) References Cited

OTHER PUBLICATIONS

Jaitin et al. "Inquiring into the differential action of interferons (IFNs): an IFN-α2 mutant with enhanced affinity to IFNAR1 is functionally similar to IFN-β." Molecular and Cellular Biology 269(5):1888-1897 (2006).

Jaks et al. "Differential receptor subunit affinities of type I interferons govern differential signal activation." Journal of Molecular Biology 366(2):525-539 (2007).

Johns et al. "Identification of the epitope for the epidermal growth factor receptor-specific monoclonal antibody 806 reveals that it preferentially recognizes an untethered form of the receptor." Journal of Biological Chemistry 279 (29):30375-30384 (2004).

Kalie et al., "The stability of the ternary interferon-receptor complex rather than the affinity to the individual subunits dictates differential biological activities." Journal of Biological Chemistry 283(47):32925-32936 (2008).

Kaufman et al. "Amplification and expression of sequences cotransfected with a modular dihydrofolate reductase complementary DNA gene." Journal of Molecular Biology 159(4):601-621 (1982).

Zhou et al. "Structural definition of a conserved neutralization epitope on HIV-1 gp120." Nature 445(7129):732-737 (2007).

Target cell

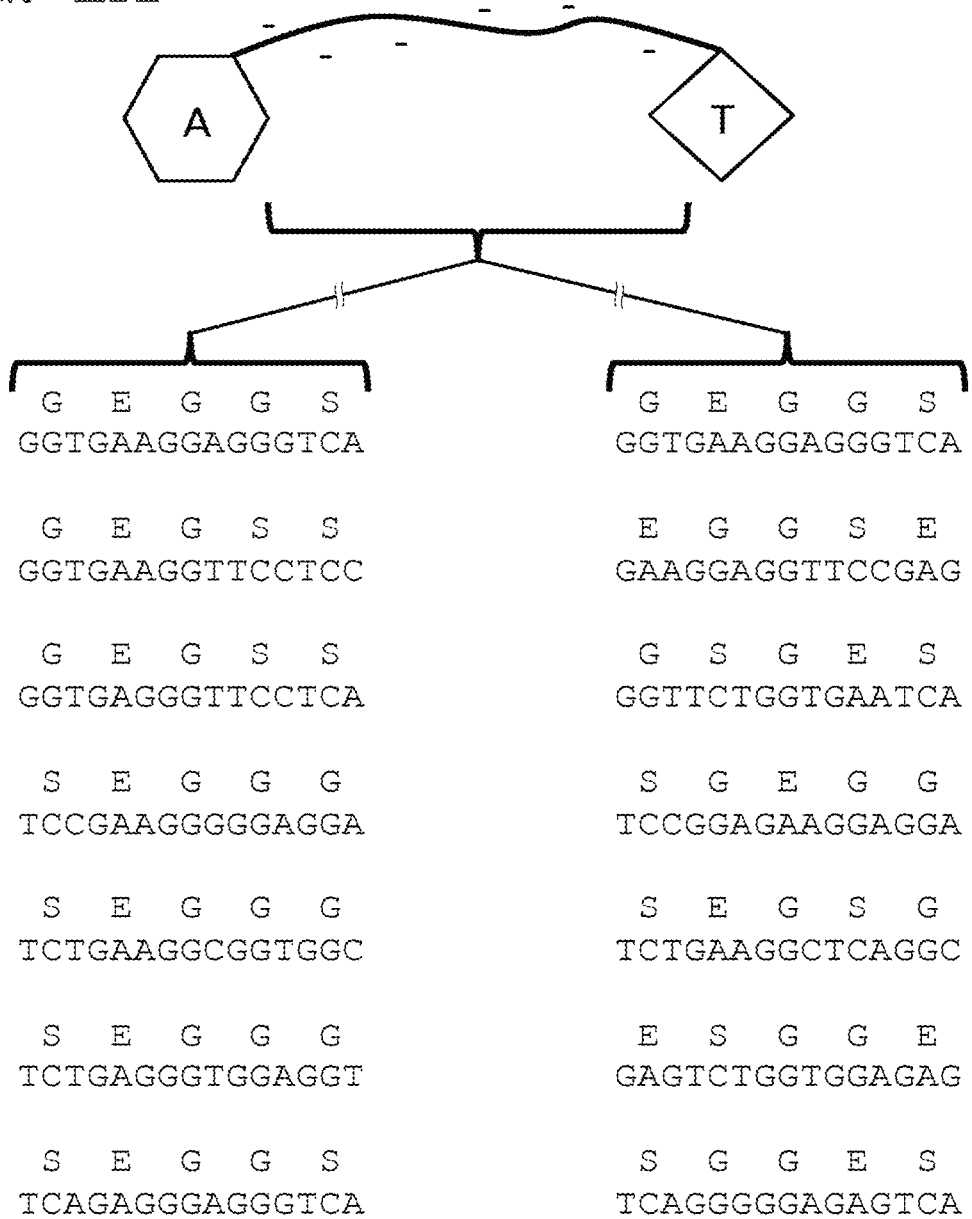

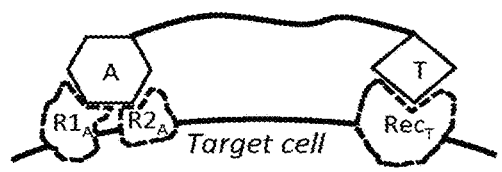
*FIG. 3A*
*FIG. 3B*
*FIG. 3C*
*FIG. 3D*
*FIG. 3E*
FIG. 3F
| Receptor subunits | | R1 | R2 | R1xR2 |
|---|---|---|---|---|
| Wild type IFNalpha2a | | 1600 | 2 | 3200 |
| L30A | | 3500 | 1700 | $6x10^6$ |
| H57A | R149A | 690 | 538 | 370,000 |
| E58A | M148A | 310 | 143 | 44,330 |
| R144A | | 1600 | 100 | 160,000 |
| R149A | | 1600 | 538 | 860,000 |

```
Hu IFNα's   ....|...|...|...20...|...|...|...40...|...|
IFNα2-1b    CDLPQTHSLGSRRTLMLLAQMRRISPFSCLKDRHDFGFPQEEFDGNQFQK
IFNα2a      CDLPQTHSLGSRRTLMLLAQMRKISLFSCLKDRHDFGFPQEEF-GNQFQK
IFNα1/13    CDLPETHSLDNRRTLMLLAQMSRISPSSCLMDRHDFGFPQEEFDGNQFQK
IFNα5       CDLPQTHSLSNRRTLMIMAQMGRISPFSCLKDRHDFGFPQEEFDGNQFQK
IFNα21      CDLPQTHSLGNRRALILLAQMGRISPFSCLKDRHDFGFPQEEFDGNQFQK
IFNα4       CDLPQTHSLGNRRALILLAQMGRISHFSCLKDRHDFGFPEEEFDGHQFQK
IFNα17      CDLPQTHSLGNRRALILLAQMGRISPFSCLKDRHDFGLPQEEFDGNQFQK
IFNα6       CDLPQTHSLGHRRTMMLLAQMRRISLFSCLKDRHDFRFPQEEFDGNQFQK
IFNα14      CNLSQTHSLNNRRTLMLMAQMRRISPFSCLKDRHDFEFPQEEFDGNQFQK
IFNα10      CDLPQTHSLGNRRALILLGQMGRISPFSCLKDRHDFRIPQEEFDGNQFQK
IFNα2b      CDLPQTHSLGSRRTLMLLAQMRRISLFSCLKDRHDFGFPQEEF GNQFQK
IFNα16      CDLPQTHSLGNRRALILLAQMGRISHFSCLKDRYDFGFPQEVFDGNQFQK
IFNα8       CDLPQTHSLGNRRALILLAQMRRISPFSCLKDRHDFEFPQEEFDDKQFQK

...|...60...|...|...|...80...|...|...|..100...|...|
            AQAISVLHEMIQQIFNLFSTKDSSAAWDETLLEKFYTELYQQLNDLEACVTQEVGVEETP
            AETIPVLHEMIQQIFNLFSTKDSSAAWDETLLDKFYTELYQQLNDLEACVIQGVGVTETP
            APAISVLHELIQQIFNLFTTKDSSAAWDEDLLDKFCTELYQQLNDLEACVMQEERVGETP
            AQAISVLHEMIQQTFNLFSTKDSSATWDETLLDKFYTELYQQLNDLEACMMQEVGVEDTP
            AQAISVLHEMIQQTFNLFSTKDSSATWEQSLLEKFSTELNQQLNDLEACVIQEVGVEETP
            AQAISVLHEMIQQTFNLFSTEDSSAAWEQSLLEKFSTELYQQLNDLEACVIQEVGVEETP
            TQAISVLHEMIQQTFNLFSTEDSSAAWEQSLLEKFSTELYQQLNNLEACVIQEVGMEETP
            AEAISVLHEVIQQTFNLFSTKDSSVAWDERLLDKLYTELYQQLNDLEACVMQEVWVGGTP
            AQAISVLHEMMQQTFNLFSTKNSSAAWDETLLEKFYIELFQQMNDLEACVIQEVGVEETP
            AQAISVLHEMIQQTFNLFSTEDSSAAWEQSLLEKFSTELYQQLNDLEACVIQEVGVEETP
            AETIPVLHEMIQQIFNLFSTKDSSAAWDETLLDKFYTELYQQLNDLEACVIQGVGVTETP
            AQAISAFHEMIQQTFNLFSTKDSSAAWDETLLDKFYIELFQQLNDLEACVTQEVGVEEIA
            AQAISVLHEMIQQTFNLFSTKDSSAALDETLLDEFYIELDQQLNDLESCVMQEVGVIESP

...|..120...|...|...|..140...|...|...|..160...|
            LMNEDSILAVKKYFQRITLYLTEKKYSPCAWEVVRAEIMRSFSLSTNLQERLRRKE
            LMKEDSILAVRKYFQRITLYLKEKKYSPCAWEVVRAEIMRSFSLSTNLQESLRSKE
            LMNADSILAVKKYFRRITLYLTEKKYSPCAWEVVRAEIMRSLSLSTNLQERLRRKE
            LMNVDSILTVRKYFQRITLYLTEKKYSPCAWEVVRAEIMRSFSLSANLQERLRRKE
            LMNVDSILAVKKYFQRITLYLTEKKYSPCAWEVVRAEIMRSFSLSKIFQERLRRKE
            LMNEDSILAVRKYFQRITLYLTEKKYSPCAWEVVRAEIMRSLSFSTNLQKRLRRKD
            LMNEDSILAVRKYFQRITLYLTEKKYSPCAWEVVRAEIMRSLSFSTNLQKRLRRKD
            LMNEDSILAVRKYFQRITLYLTEKKYSPCAWEVVRAEIMRSFSSSRNLQERLRRKE
            LMNEDSILAVKKYFQRITLYLMEKKYSPCAWEVVRAEIMRSLSFSTNLQKRLRRKD
            LMNEDSILAVRKYFQRITLYLIERKYSPCAWEVVRAEIMRSLSFSTNLQKRLRRKD
            LMNEDSILAVRKYFQRITLYLKEKKYSPCAWEVVRAEIMRSFSLSTNLQESLRSKE
            LMNEDSILAVRKYFQRITLYLMGKKYSPCAWEVVRAEIMRSFSFSTNLQKGLRRKD
            LMYEDSILAVRKYFQRITLYLTEKKYSSCAWEVVRAEIMRSFSLSINLQKRLKSKE
```

*FIG. 4*

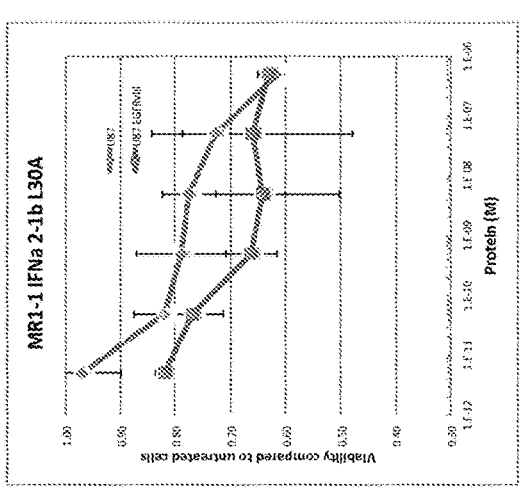
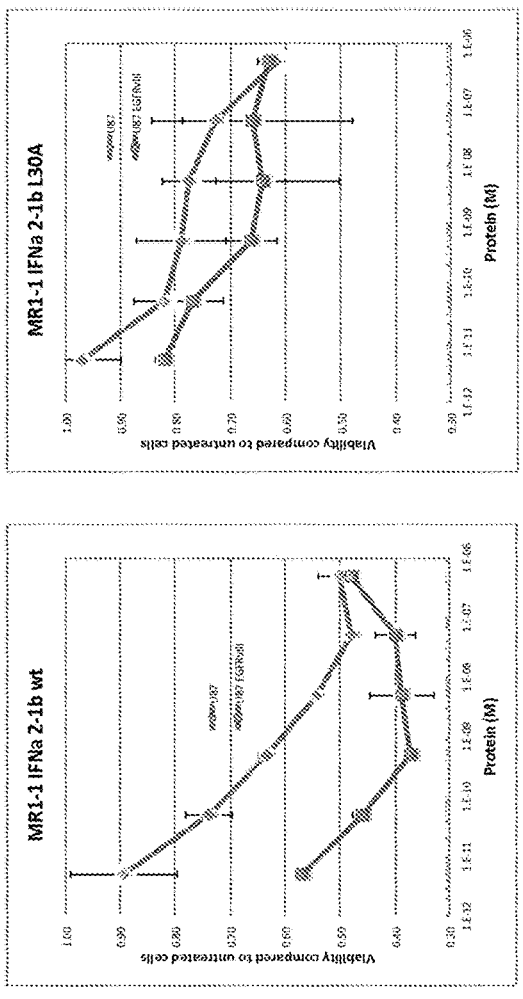
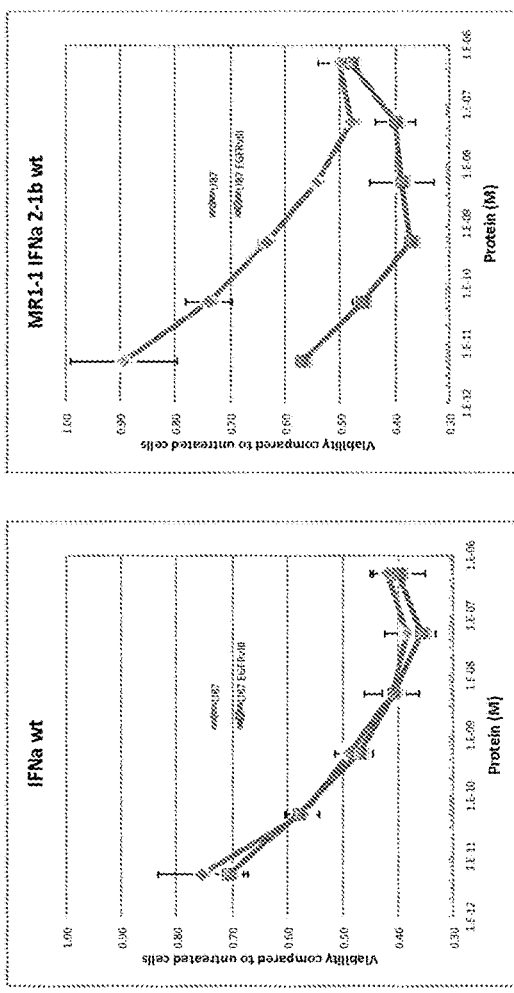
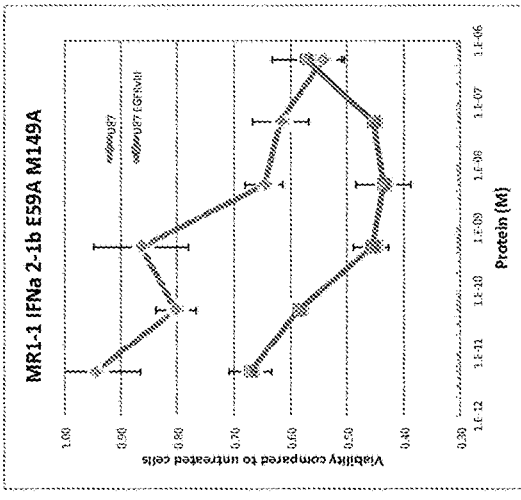
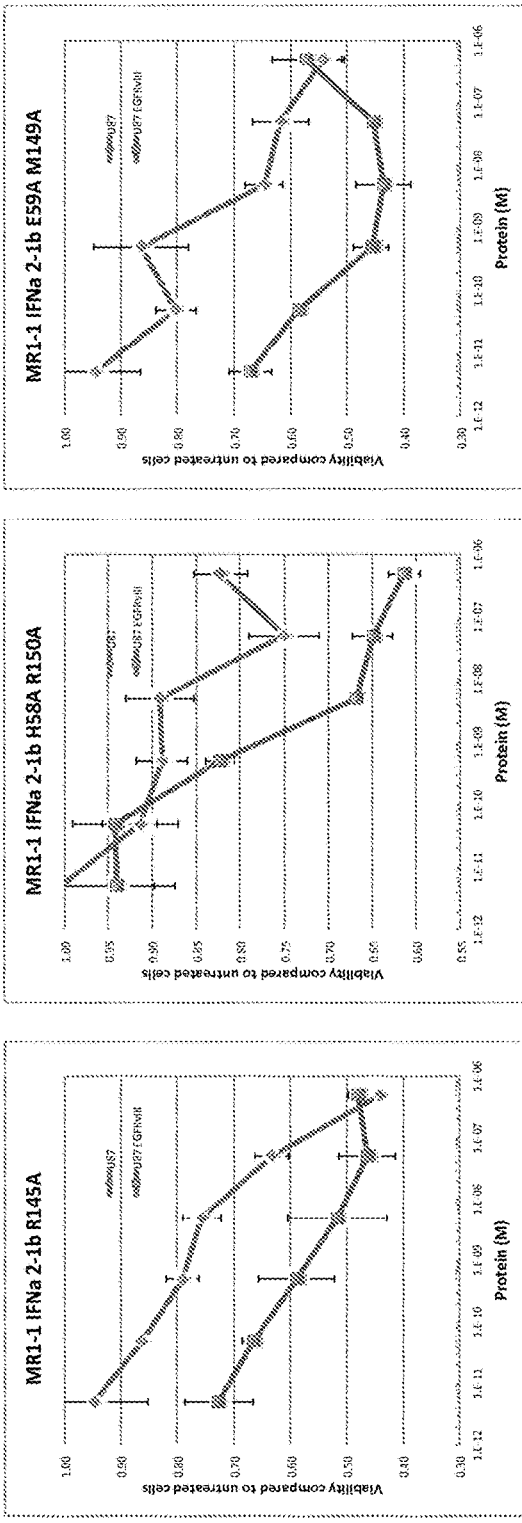

```
                          SEQUENCE LISTING

<160> NUMBER OF SEQ ID NOS: 40

<210> SEQ ID NO 1
<211> LENGTH: 449
<212> TYPE: PRT
<213> ORGANISM: Artificial Sequence
<220> FEATURE:
<223> OTHER INFORMATION: Synthetic Polypeptide

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Lys Val Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ala Ser Ile Ser Thr Gly Gly Tyr Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Ser Pro Tyr Ser Tyr Ala Met Asp Tyr Trp Gly Gln
            100                 105                 110

Gly Thr Thr Val Thr Val Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Arg Ala
145                 150                 155                 160

Ser Thr Asp Ile Asp Asn Asp Met Asn Trp Tyr Gln Gln Lys Pro Gly
                165                 170                 175

Gln Ala Pro Lys Leu Leu Ile Tyr Glu Gly Asn Ser Leu Gln Ser Gly
            180                 185                 190

Val Pro Ser Arg Phe Ser Ser Ser Gly Ser Gly Thr Asp Phe Thr Leu
        195                 200                 205

Thr Ile Ser Ser Leu Gln Pro Glu Asp Phe Ala Thr Tyr Tyr Cys Leu
    210                 215                 220

Gln Ser Trp Asn Val Pro Leu Thr Phe Gly Gln Gly Thr Lys Leu Glu
225                 230                 235                 240

Ile Lys Gly Glu Gly Gly Ser Gly Glu Gly Ser Ser Gly Glu Gly Ser
                245                 250                 255

Ser Ser Glu Gly Gly Gly Ser Gly Gly Gly Ser Glu Gly Gly Gly
            260                 265                 270

Ser Glu Gly Gly Ser Cys Asp Leu Pro Gln Thr His Ser Leu Gly Ser
        275                 280                 285

Arg Arg Thr Leu Met Leu Leu Ala Gln Met Arg Arg Ile Ser Pro Phe
    290                 295                 300

Ser Cys Leu Lys Asp Arg His Asp Phe Gly Phe Pro Gln Glu Glu Phe
305                 310                 315                 320

Asp Gly Asn Gln Phe Gln Lys Ala Gln Ala Ile Ser Val Leu His Glu
                325                 330                 335
```

Met Ile Gln Gln Ile Phe Asn Leu Phe Ser Thr Lys Asp Ser Ser Ala
         340                 345                 350

Ala Trp Asp Glu Thr Leu Leu Glu Lys Phe Tyr Thr Glu Leu Tyr Gln
         355                 360                 365

Gln Leu Asn Asp Leu Glu Ala Cys Val Thr Gln Glu Val Gly Val Glu
    370                 375                 380

Glu Thr Pro Leu Met Asn Glu Asp Ser Ile Leu Ala Val Lys Lys Tyr
385                 390                 395                 400

Phe Gln Arg Ile Thr Leu Tyr Leu Thr Glu Lys Lys Tyr Ser Pro Cys
             405                 410                 415

Ala Trp Glu Val Val Arg Ala Glu Ile Met Arg Ser Phe Ser Leu Ser
         420                 425                 430

Thr Asn Leu Gln Glu Arg Leu Arg Arg Lys Glu His His His His
         435                 440                 445

His

<210> SEQ ID NO 2
<211> LENGTH: 449
<212> TYPE: PRT
<213> ORGANISM: Artificial Sequence
<220> FEATURE:
<223> OTHER INFORMATION: Synthetic Polypeptide

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Lys Val Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ala Ser Ile Ser Thr Gly Gly Tyr Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Ser Pro Tyr Ser Tyr Ala Met Asp Tyr Trp Gly Gln
            100                 105                 110

Gly Thr Thr Val Thr Val Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Arg Ala
145                 150                 155                 160

Ser Thr Asp Ile Asp Asn Asp Met Asn Trp Tyr Gln Gln Lys Pro Gly
                165                 170                 175

Gln Ala Pro Lys Leu Leu Ile Tyr Glu Gly Asn Ser Leu Gln Ser Gly
            180                 185                 190

Val Pro Ser Arg Phe Ser Ser Ser Gly Ser Gly Thr Asp Phe Thr Leu
        195                 200                 205

Thr Ile Ser Ser Leu Gln Pro Glu Asp Phe Ala Thr Tyr Tyr Cys Leu
    210                 215                 220

Gln Ser Trp Asn Val Pro Leu Thr Phe Gly Gln Gly Thr Lys Leu Glu
225                 230                 235                 240

```
Ile Lys Gly Glu Gly Gly Ser Gly Glu Gly Ser Ser Gly Glu Gly Ser
            245                 250                 255

Ser Ser Glu Gly Gly Gly Ser Gly Gly Gly Ser Gly Gly Gly
        260                 265                 270

Ser Glu Gly Gly Ser Cys Asp Leu Pro Gln Thr His Ser Leu Gly Ser
        275                 280                 285

Arg Arg Thr Leu Met Leu Leu Ala Gln Met Arg Arg Ile Ser Pro Phe
        290                 295                 300

Ser Cys Ala Lys Asp Arg His Asp Phe Gly Phe Pro Gln Glu Glu Phe
305                 310                 315                 320

Asp Gly Asn Gln Phe Gln Lys Ala Gln Ala Ile Ser Val Leu His Glu
                325                 330                 335

Met Ile Gln Gln Ile Phe Asn Leu Phe Ser Thr Lys Asp Ser Ser Ala
            340                 345                 350

Ala Trp Asp Glu Thr Leu Leu Glu Lys Phe Tyr Thr Glu Leu Tyr Gln
                355                 360                 365

Gln Leu Asn Asp Leu Glu Ala Cys Val Thr Gln Glu Val Gly Val Glu
        370                 375                 380

Glu Thr Pro Leu Met Asn Glu Asp Ser Ile Leu Ala Val Lys Lys Tyr
385                 390                 395                 400

Phe Gln Arg Ile Thr Leu Tyr Leu Thr Glu Lys Lys Tyr Ser Pro Cys
                405                 410                 415

Ala Trp Glu Val Val Arg Ala Glu Ile Met Arg Ser Phe Ser Leu Ser
                420                 425                 430

Thr Asn Leu Gln Glu Arg Leu Arg Arg Lys Glu His His His His
        435                 440                 445

His

<210> SEQ ID NO 3
<211> LENGTH: 449
<212> TYPE: PRT
<213> ORGANISM: Artificial Sequence
<220> FEATURE:
<223> OTHER INFORMATION: Synthetic Polypeptide

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Lys Val Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ala Ser Ile Ser Thr Gly Gly Tyr Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Ser Pro Tyr Ser Tyr Ala Met Asp Tyr Trp Gly Gln
            100                 105                 110

Gly Thr Thr Val Thr Val Ser Gly Gly Gly Gly Ser Gly Gly Gly
        115                 120                 125

Gly Ser Gly Gly Gly Gly Ser Asp Ile Gln Met Thr Gln Ser Pro Ser
        130                 135                 140

Ser Leu Ser Ala Ser Val Gly Asp Arg Val Thr Ile Thr Cys Arg Ala
```

```
                        145                 150                 155                 160
Ser Thr Asp Ile Asp Asn Asp Met Asn Trp Tyr Gln Gln Lys Pro Gly
                165                 170                 175

Gln Ala Pro Lys Leu Leu Ile Tyr Glu Gly Asn Ser Leu Gln Ser Gly
            180                 185                 190

Val Pro Ser Arg Phe Ser Ser Gly Ser Gly Thr Asp Phe Thr Leu
        195                 200                 205

Thr Ile Ser Ser Leu Gln Pro Glu Asp Phe Ala Thr Tyr Tyr Cys Leu
    210                 215                 220

Gln Ser Trp Asn Val Pro Leu Thr Phe Gly Gln Gly Thr Lys Leu Glu
225                 230                 235                 240

Ile Lys Gly Glu Gly Gly Ser Gly Gly Ser Ser Gly Glu Gly Ser
                245                 250                 255

Ser Ser Glu Gly Gly Ser Gly Gly Gly Ser Glu Gly Gly
            260                 265                 270

Ser Glu Gly Gly Ser Cys Asp Leu Pro Gln Thr His Ser Leu Gly Ser
        275                 280                 285

Arg Arg Thr Leu Met Leu Leu Ala Gln Met Arg Arg Ile Ser Pro Phe
        290                 295                 300

Ser Cys Leu Lys Asp Arg His Asp Phe Gly Phe Pro Gln Glu Glu Phe
305                 310                 315                 320

Asp Gly Asn Gln Phe Gln Lys Ala Gln Ala Ile Ser Val Leu His Glu
                325                 330                 335

Met Ile Gln Gln Ile Phe Asn Leu Phe Ser Thr Lys Asp Ser Ser Ala
            340                 345                 350

Ala Trp Asp Glu Thr Leu Leu Glu Lys Phe Tyr Thr Glu Leu Tyr Gln
        355                 360                 365

Gln Leu Asn Asp Leu Glu Ala Cys Val Thr Gln Glu Val Gly Val Glu
    370                 375                 380

Glu Thr Pro Leu Met Asn Glu Asp Ser Ile Leu Ala Val Lys Lys Tyr
385                 390                 395                 400

Phe Gln Arg Ile Thr Leu Tyr Leu Thr Glu Lys Lys Tyr Ser Pro Cys
                405                 410                 415

Ala Trp Glu Val Val Ala Ala Glu Ile Met Arg Ser Phe Ser Leu Ser
            420                 425                 430

Thr Asn Leu Gln Glu Arg Leu Arg Arg Lys Glu His His His His
        435                 440                 445

His

<210> SEQ ID NO 4
<211> LENGTH: 449
<212> TYPE: PRT
<213> ORGANISM: Artificial Sequence
<220> FEATURE:
<223> OTHER INFORMATION: Synthetic Polypeptide

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Lys Val Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ala Ser Ile Ser Thr Gly Gly Tyr Asn Thr Tyr Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Tyr Ser Pro Tyr Ser Tyr Ala Met Asp Tyr Trp Gly Gln
            100                 105                 110

Gly Thr Thr Val Thr Val Ser Gly Gly Gly Gly Ser Gly Gly Gly
            115                 120                 125

Gly Ser Gly Gly Gly Gly Ser Asp Ile Gln Met Thr Gln Ser Pro Ser
        130                 135                 140

Ser Leu Ser Ala Ser Val Gly Asp Arg Val Thr Ile Thr Cys Arg Ala
145                 150                 155                 160

Ser Thr Asp Ile Asp Asn Asp Met Asn Trp Tyr Gln Gln Lys Pro Gly
                165                 170                 175

Gln Ala Pro Lys Leu Leu Ile Tyr Glu Gly Asn Ser Leu Gln Ser Gly
            180                 185                 190

Val Pro Ser Arg Phe Ser Ser Gly Ser Gly Thr Asp Phe Thr Leu
            195                 200                 205

Thr Ile Ser Ser Leu Gln Pro Glu Asp Phe Ala Thr Tyr Tyr Cys Leu
210                 215                 220

Gln Ser Trp Asn Val Pro Leu Thr Phe Gly Gln Gly Thr Lys Leu Glu
225                 230                 235                 240

Ile Lys Gly Glu Gly Gly Ser Gly Glu Gly Ser Ser Gly Glu Gly Ser
            245                 250                 255

Ser Ser Glu Gly Gly Ser Glu Gly Gly Ser Glu Gly Gly Gly
        260                 265                 270

Ser Glu Gly Gly Ser Cys Asp Leu Pro Gln Thr His Ser Leu Gly Ser
        275                 280                 285

Arg Arg Thr Leu Met Leu Leu Ala Gln Met Arg Arg Ile Ser Pro Phe
        290                 295                 300

Ser Cys Leu Lys Asp Arg His Asp Phe Gly Phe Pro Gln Glu Glu Phe
305                 310                 315                 320

Asp Gly Asn Gln Phe Gln Lys Ala Gln Ala Ile Ser Val Leu His Ala
                325                 330                 335

Met Ile Gln Gln Ile Phe Asn Leu Phe Ser Thr Lys Asp Ser Ser Ala
            340                 345                 350

Ala Trp Asp Glu Thr Leu Leu Glu Lys Phe Tyr Thr Glu Leu Tyr Gln
            355                 360                 365

Gln Leu Asn Asp Leu Glu Ala Cys Val Thr Gln Glu Val Gly Val Glu
            370                 375                 380

Glu Thr Pro Leu Met Asn Glu Asp Ser Ile Leu Ala Val Lys Lys Tyr
385                 390                 395                 400

Phe Gln Arg Ile Thr Leu Tyr Leu Thr Glu Lys Lys Tyr Ser Pro Cys
                405                 410                 415

Ala Trp Glu Val Val Arg Ala Glu Ile Ala Arg Ser Phe Ser Leu Ser
            420                 425                 430

Thr Asn Leu Gln Glu Arg Leu Arg Arg Lys Glu His His His His
        435                 440                 445

His

<210> SEQ ID NO 5
<211> LENGTH: 449
<212> TYPE: PRT
```

<213> ORGANISM: Artificial Sequence
<220> FEATURE:
<223> OTHER INFORMATION: Synthetic Polypeptide

<400> SEQUENCE: 5

```
Glu Val Gln Leu Val Glu Ser Gly Gly Gly Leu Val Gln Pro Gly Gly
1               5                   10                  15

Ser Leu Arg Leu Ser Cys Lys Val Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ala Ser Ile Ser Thr Gly Gly Tyr Asn Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Ser Pro Tyr Ser Tyr Ala Met Asp Tyr Trp Gly Gln
            100                 105                 110

Gly Thr Thr Val Thr Val Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Arg Ala
145                 150                 155                 160

Ser Thr Asp Ile Asp Asn Asp Met Asn Trp Tyr Gln Gln Lys Pro Gly
                165                 170                 175

Gln Ala Pro Lys Leu Leu Ile Tyr Glu Gly Asn Ser Leu Gln Ser Gly
            180                 185                 190

Val Pro Ser Arg Phe Ser Ser Gly Ser Gly Thr Asp Phe Thr Leu
        195                 200                 205

Thr Ile Ser Ser Leu Gln Pro Glu Asp Phe Ala Thr Tyr Tyr Cys Leu
    210                 215                 220

Gln Ser Trp Asn Val Pro Leu Thr Phe Gly Gln Gly Thr Lys Leu Glu
225                 230                 235                 240

Ile Lys Gly Glu Gly Gly Ser Gly Glu Gly Ser Ser Gly Glu Gly Ser
                245                 250                 255

Ser Ser Glu Gly Gly Ser Glu Gly Gly Ser Glu Gly Gly
            260                 265                 270

Ser Glu Gly Gly Ser Cys Asp Leu Pro Gln Thr His Ser Leu Gly Ser
        275                 280                 285

Arg Arg Thr Leu Met Leu Leu Ala Gln Met Arg Arg Ile Ser Pro Phe
    290                 295                 300

Ser Cys Leu Lys Asp Arg His Asp Phe Gly Phe Pro Gln Glu Glu Phe
305                 310                 315                 320

Asp Gly Asn Gln Phe Gln Lys Ala Gln Ala Ile Ser Val Leu Ala Glu
                325                 330                 335

Met Ile Gln Gln Ile Phe Asn Leu Phe Ser Thr Lys Asp Ser Ser Ala
            340                 345                 350

Ala Trp Asp Glu Thr Leu Leu Glu Lys Phe Tyr Thr Glu Leu Tyr Gln
        355                 360                 365

Gln Leu Asn Asp Leu Glu Ala Cys Val Thr Gln Glu Val Gly Val Glu
    370                 375                 380

Glu Thr Pro Leu Met Asn Glu Asp Ser Ile Leu Ala Val Lys Lys Tyr
```

385 390 395 400

Phe Gln Arg Ile Thr Leu Tyr Leu Thr Glu Lys Lys Tyr Ser Pro Cys
            405                 410                 415

Ala Trp Glu Val Val Arg Ala Glu Ile Met Ala Ser Phe Ser Leu Ser
            420                 425                 430

Thr Asn Leu Gln Glu Arg Leu Arg Arg Lys Glu His His His His
            435                 440                 445

His

<210> SEQ ID NO 6
<211> LENGTH: 1350
<212> TYPE: DNA
<213> ORGANISM: Artificial Sequence
<220> FEATURE:
<223> OTHER INFORMATION: Synthetic Polynucleotide

<400> SEQUENCE: 6

| | | | | |
|---|---|---|---|---|
| gaagttcaat tggttgagtc tggtggaggt ttggttcaac caggaggttc cttgagattg | | | | 60 |
| tcatgtaaag tttctggttt tactttctct tcctatggaa tgtcttgggt tagacaagct | | | | 120 |
| cctggaaagg gtttggaatg ggttgcttcc atctcaaccg gtggttacaa cacatattac | | | | 180 |
| gctgattccg ttaaaggtag attcactatc tccagagata actctaagaa cactttgtat | | | | 240 |
| ttgcaaatga actctttgag agctgaagat actgctgttt actattgtgc gcgcggttac | | | | 300 |
| tctccatatt cttacgctat ggattattgg ggtcaaggta ctactgttac tgtttctggt | | | | 360 |
| ggaggtggag gttcaggagg tggaggaagt ggaggaggtg gatcagacat ccagatgaca | | | | 420 |
| caatcaccat cttccttgtc agcttctgtt ggagatagag ttactattac atgtagagct | | | | 480 |
| tccactgaca tcgataacga catgaattgg tatcagcaaa aacctggaca ggcgccaaag | | | | 540 |
| ttgttgatct acgagggtaa ctcattgcaa tctggagttc cttccagatt ttcatcttcc | | | | 600 |
| ggttccggaa cagatttcac tttgacaatc tcttccttgc agccagaaga ctttgctact | | | | 660 |
| tattactgtt tgcaatcatg gaatgttcct ttgacattcg gtcaaggaac taaattggag | | | | 720 |
| attaagggtg aaggagggtc aggtgaaggt tcctccggtg agggttcctc atccgaaggg | | | | 780 |
| ggaggatctg aaggcggtgg ctctgagggt ggaggttcag agggagggtc atgtgacttg | | | | 840 |
| cctcaaactc attctttggg ttctagaaga actttgatgt tgttggctca aatgagaaga | | | | 900 |
| atctctcctt tctcttgttt gaaggacaga catgacttcg gtttccctca agaggagttc | | | | 960 |
| gacggtaacc aattccaaaa ggctcaagct atctctgtct tgcatgagat gatccaacaa | | | | 1020 |
| atcttcaact tgttctctac taaggactct tctgctgctt gggacgagac tttgttggag | | | | 1080 |
| aagttctaca ctgagttgta ccaacaattg aacgacttgg aggcttgtgt cactcaagag | | | | 1140 |
| gtcggtgtcg aggagactcc tttgatgaac gaggactcta tcttggctgt caagaagtac | | | | 1200 |
| ttccaaagaa tcactttgta cttgactgag aagaagtact ctccttgtgc ttgggaggtc | | | | 1260 |
| gtcagagctg agatcatgag atctttctct ttgtctacta acttgcaaga gagattgaga | | | | 1320 |
| agaaaggagc atcaccatca ccatcactaa | | | | 1350 |

<210> SEQ ID NO 7
<211> LENGTH: 1350
<212> TYPE: DNA
<213> ORGANISM: Artificial Sequence
<220> FEATURE:
<223> OTHER INFORMATION: Synthetic Polynucleotide

<400> SEQUENCE: 7

```
gaagttcaat tggttgagtc tggtggaggt ttggttcaac caggaggttc cttgagattg      60
tcatgtaaag tttctggttt tactttctct tcctatggaa tgtcttgggt tagacaagct     120
cctggaaagg gtttggaatg ggttgcttcc atctcaaccg gtggttacaa cacatattac     180
gctgattccg ttaaaggtag attcactatc tccagagata actctaagaa cactttgtat     240
ttgcaaatga actctttgag agctgaagat actgctgttt actattgtgc gcgcggttac     300
tctccatatt cttacgctat ggattattgg ggtcaaggta ctactgttac tgtttctggt     360
ggaggtggag gttcaggagg tggaggaagt ggaggaggtg gatcagacat ccagatgaca     420
caatcaccat cttccttgtc agcttctgtt ggagatagag ttactattac atgtagagct     480
tccactgaca tcgataacga catgaattgg tatcagcaaa aacctggaca ggcgccaaag     540
ttgttgatct acgagggtaa ctcattgcaa tctggagttc cttccagatt ttcatcttcc     600
ggttccggaa cagatttcac tttgacaatc tcttccttgc agccagaaga ctttgctact     660
tattactgtt tgcaatcatg gaatgttcct ttgacattcg gtcaaggaac taaattggag     720
attaagggtg aaggagggtc aggtgaaggt tcctccggtg agggttcctc atccgaaggg     780
ggaggatctg aaggcggtgg ctctgagggt ggaggttcag agggagggtc atgtgacttg     840
cctcaaactc attctttggg ttctagaaga actttgatgt tgttggctca aatgagaaga     900
atctctcctt tctcttgtgc taaggacaga catgacttcg gttccctca agaggagttc     960 gacggtaacc aattccaaaa ggctcaagct atctctgtct tgcatgagat gatccaacaa    1020
atcttcaact tgttctctac taaggactct tctgctgctt gggacgagac tttgttggag    1080
aagttctaca ctgagttgta ccaacaattg aacgacttgg aggcttgtgt cactcaagag    1140
gtcggtgtcg aggagactcc tttgatgaac gaggactcta tcttggctgt caagaagtac    1200
ttccaaagaa tcactttgta cttgactgag aagaagtact ctccttgtgc ttgggaggtc    1260
gtcagagctg agatcatgag atctttctct ttgtctacta acttgcaaga gagattgaga    1320
agaaaggagc atcaccatca ccatcactaa                                      1350

<210> SEQ ID NO 8
<211> LENGTH: 1350
<212> TYPE: DNA
<213> ORGANISM: Artificial Sequence
<220> FEATURE:
<223> OTHER INFORMATION: Synthetic Polynucleotide

<400> SEQUENCE: 8
gaagttcaat tggttgagtc tggtggaggt ttggttcaac caggaggttc cttgagattg      60
tcatgtaaag tttctggttt tactttctct tcctatggaa tgtcttgggt tagacaagct     120
cctggaaagg gtttggaatg ggttgcttcc atctcaaccg gtggttacaa cacatattac     180
gctgattccg ttaaaggtag attcactatc tccagagata actctaagaa cactttgtat     240
ttgcaaatga actctttgag agctgaagat actgctgttt actattgtgc gcgcggttac     300
tctccatatt cttacgctat ggattattgg ggtcaaggta ctactgttac tgtttctggt     360
ggaggtggag gttcaggagg tggaggaagt ggaggaggtg gatcagacat ccagatgaca     420
caatcaccat cttccttgtc agcttctgtt ggagatagag ttactattac atgtagagct     480
tccactgaca tcgataacga catgaattgg tatcagcaaa aacctggaca ggcgccaaag     540
ttgttgatct acgagggtaa ctcattgcaa tctggagttc cttccagatt ttcatcttcc     600
ggttccggaa cagatttcac tttgacaatc tcttccttgc agccagaaga ctttgctact     660
tattactgtt tgcaatcatg gaatgttcct ttgacattcg gtcaaggaac taaattggag     720
```

```
attaagggtg aaggagggtc aggtgaaggt tcctccggtg agggttcctc atccgaaggg      780
ggaggatctg aaggcggtgg ctctgagggt ggaggttcag agggagggtc atgtgacttg      840
cctcaaactc attctttggg ttctagaaga actttgatgt tgttggctca aatgagaaga      900
atctctcctt tctcttgttt gaaggacaga catgacttcg gtttccctca agaggagttc      960
gacggtaacc aattccaaaa ggctcaagct atctctgtct tgcatgagat gatccaacaa     1020
atcttcaact tgttctctac taaggactct tctgctgctt gggacgagac tttgttggag     1080
aagttctaca ctgagttgta ccaacaattg aacgacttgg aggcttgtgt cactcaagag     1140
gtcggtgtcg aggagactcc tttgatgaac gaggactcta tcttggctgt caagaagtac     1200
ttccaaagaa tcactttgta cttgactgag aagaagtact ctccttgtgc ttgggaggtc     1260
gtcgctgctg agatcatgag atctttctct ttgtctacta acttgcaaga gagattgaga     1320
agaaaggagc atcaccatca ccatcactaa                                      1350
```

<210> SEQ ID NO 9
<211> LENGTH: 1350
<212> TYPE: DNA
<213> ORGANISM: Artificial Sequence
<220> FEATURE:
<223> OTHER INFORMATION: Synthetic Polynucleotide

<400> SEQUENCE: 9

```
gaagttcaat tggttgagtc tggtggaggt ttggttcaac caggaggttc cttgagattg       60
tcatgtaaag tttctggttt tactttctct tcctatggaa tgtcttgggt tagacaagct      120
cctggaaagg gtttggaatg ggttgcttcc atctcaaccg gtggttacaa cacatattac      180
gctgattccg ttaaaggtag attcactatc tccagagata actctaagaa cactttgtat      240
ttgcaaatga actctttgag agctgaagat actgctgttt actattgtgc gcgcggttac      300
tctccatatt cttacgctat ggattattgg ggtcaaggta ctactgttac tgtttctggt      360
ggaggtggag gttcaggagg tggaggaagt ggaggaggtg gatcagacat ccagatgaca      420
caatcaccat cttccttgtc agcttctgtt ggagatagag ttactattac atgtagagct      480
tccactgaca tcgataacga catgaattgg tatcagcaaa aacctggaca ggcgccaaag      540
ttgttgatct acgagggtaa ctcattgcaa tctggagttc cttccagatt ttcatcttcc      600
ggttccggaa cagatttcac tttgacaatc tcttccttgc agccagaaga ctttgctact      660
tattactgtt tgcaatcatg gaatgttcct ttgacattcg gtcaaggaac taaattggag      720
attaagggtg aaggagggtc aggtgaaggt tcctccggtg agggttcctc atccgaaggg      780
ggaggatctg aaggcggtgg ctctgagggt ggaggttcag agggagggtc atgtgacttg      840
cctcaaactc attctttggg ttctagaaga actttgatgt tgttggctca aatgagaaga      900
atctctcctt tctcttgttt gaaggacaga catgacttcg gtttccctca agaggagttc      960
gacggtaacc aattccaaaa ggctcaagct atctctgtct tgcatgcgat gatccaacaa     1020
atcttcaact tgttctctac taaggactct tctgctgctt gggacgagac tttgttggag     1080
aagttctaca ctgagttgta ccaacaattg aacgacttgg aggcttgtgt cactcaagag     1140
gtcggtgtcg aggagactcc tttgatgaac gaggactcta tcttggctgt caagaagtac     1200
ttccaaagaa tcactttgta cttgactgag aagaagtact ctccttgtgc ttgggaggtc     1260
gtcagagctg agatcgcgag atctttctct ttgtctacta acttgcaaga gagattgaga     1320
agaaaggagc atcaccatca ccatcactaa                                      1350
```

<210> SEQ ID NO 10
<211> LENGTH: 1350
<212> TYPE: DNA
<213> ORGANISM: Artificial Sequence
<220> FEATURE:
<223> OTHER INFORMATION: Synthetic Polynucleotide

<400> SEQUENCE: 10

| | | | | | |
|---|---|---|---|---|---|
| gaagttcaat | tggttgagtc | tggtggaggt | ttggttcaac | caggaggttc | cttgagattg | 60 |
| tcatgtaaag | tttctggttt | tactttctct | tcctatggaa | tgtcttgggt | tagacaagct | 120 |
| cctggaaagg | gtttggaatg | ggttgcttcc | atctcaaccg | gtggttacaa | cacatattac | 180 |
| gctgattccg | ttaaaggtag | attcactatc | tccagagata | actctaagaa | cactttgtat | 240 |
| ttgcaaatga | actcttttgag | agctgaagat | actgctgttt | actattgtgc | gcgcggttac | 300 |
| tctccatatt | cttacgctat | ggattattgg | ggtcaaggta | ctactgttac | tgtttctggt | 360 |
| ggaggtggag | gttcaggagg | tggaggaagt | ggaggaggtg | gatcagacat | ccagatgaca | 420 |
| caatcaccat | cttccttgtc | agcttctgtt | ggagatagag | ttactattac | atgtagagct | 480 |
| tccactgaca | tcgataacga | catgaattgg | tatcagcaaa | aacctggaca | ggcgccaaag | 540 |
| ttgttgatct | acgagggtaa | ctcattgcaa | tctggagttc | cttccagatt | tcatcttcc | 600 |
| ggttccggaa | cagatttcac | tttgacaatc | tcttccttgc | agccagaaga | ctttgctact | 660 |
| tattactgtt | tgcaatcatg | gaatgttcct | ttgacattcg | gtcaaggaac | taaattggag | 720 |
| attaagggtg | aaggagggtc | aggtgaaggt | tcctccggtg | agggttcctc | atccgaaggg | 780 |
| ggaggatctg | aaggcggtgg | ctctgagggt | ggaggttcag | agggagggtc | atgtgacttg | 840 |
| cctcaaactc | attctttggg | ttctagaaga | actttgatgt | tgttggctca | aatgagaaga | 900 |
| atctctcctt | tctcttgttt | gaaggacaga | catgacttcg | gtttccctca | agaggagttc | 960 |
| gacggtaacc | aattccaaaa | ggctcaagct | atctctgtct | tggctgagat | gatccaacaa | 1020 |
| atcttcaact | tgttctctac | taaggactct | tctgctgctt | gggacgagac | tttgttggag | 1080 |
| aagttctaca | ctgagttgta | ccaacaattg | aacgacttgg | aggcttgtgt | cactcaagag | 1140 |
| gtcggtgtcg | aggagactcc | tttgatgaac | gaggactcta | tcttggctgt | caagaagtac | 1200 |
| ttccaaagaa | tcactttgta | cttgactgag | aagaagtact | ctccttgtgc | ttgggaggtc | 1260 |
| gtcagagctg | agatcatggc | atctttctct | ttgtctacta | acttgcaaga | gagattgaga | 1320 |
| agaaaggagc | atcaccatca | ccatcactaa | | | | 1350 |

<210> SEQ ID NO 11
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 11

Gly Gly Gly Ser Glu
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 12

```
Gly Ser Glu Ser Gly
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 13

Gly Ser Glu Gly Ser
1               5

<210> SEQ ID NO 14
<211> LENGTH: 35
<212> TYPE: PRT
<213> ORGANISM: Artificial Sequence
<220> FEATURE:
<223> OTHER INFORMATION: Synthetic Polypeptide

<400> SEQUENCE: 14

Gly Glu Gly Gly Ser Gly Glu Gly Ser Ser Gly Glu Gly Ser Ser
1               5                   10                  15

Glu Gly Gly Gly Ser Glu Gly Gly Gly Ser Glu Gly Gly Gly Ser Glu
            20                  25                  30

Gly Gly Ser
        35

<210> SEQ ID NO 15
<211> LENGTH: 119
<212> TYPE: PRT
<213> ORGANISM: Artificial Sequence
<220> FEATURE:
<223> OTHER INFORMATION: Synthetic Polypeptide

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Lys Val Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ala Ser Ile Ser Thr Gly Gly Tyr Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Ser Pro Tyr Ser Tyr Ala Met Asp Tyr Trp Gly Gln
            100                 105                 110

Gly Thr Thr Val Thr Val Ser
        115

<210> SEQ ID NO 16
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 16
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Thr Asp Ile Asp Asn Asp
            20                  25                  30

Met Asn Trp Tyr Gln Gln Lys Pro Gly Gln Ala Pro Lys Leu Leu Ile
        35                  40                  45

Tyr Glu Gly Asn Ser Leu Gln Ser Gly Val Pro Ser Arg Phe Ser Ser
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Ser Trp Asn Val Pro Leu
                85                  90                  95

Thr Phe Gly Gln Gly Thr Lys Leu Glu Ile Lys
            100                 105
```

<210> SEQ ID NO 17
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 17

```
Lys Gly Asn Tyr Val Val Thr Asp His
1               5
```

<210> SEQ ID NO 18
<211> LENGTH: 166
<212> TYPE: PRT
<213> ORGANISM: Artificial Sequence
<220> FEATURE:
<223> OTHER INFORMATION: Synthetic Polypeptide

<400> SEQUENCE: 18

```
Cys Asp Leu Pro Gln Thr His Ser Leu Gly Ser Arg Arg Thr Leu Met
1               5                   10                  15

Leu Leu Ala Gln Met Arg Arg Ile Ser Pro Phe Ser Cys Leu Lys Asp
            20                  25                  30

Arg His Asp Phe Gly Phe Pro Gln Glu Glu Phe Asp Gly Asn Gln Phe
        35                  40                  45

Gln Lys Ala Gln Ala Ile Ser Val Leu His Glu Met Ile Gln Gln Ile
50                  55                  60

Phe Asn Leu Phe Ser Thr Lys Asp Ser Ser Ala Ala Trp Asp Glu Thr
65                  70                  75                  80

Leu Leu Glu Lys Phe Tyr Thr Glu Leu Tyr Gln Gln Leu Asn Asp Leu
                85                  90                  95

Glu Ala Cys Val Thr Gln Glu Val Gly Val Glu Thr Pro Leu Met
            100                 105                 110

Asn Glu Asp Ser Ile Leu Ala Val Lys Lys Tyr Phe Gln Arg Ile Thr
        115                 120                 125

Leu Tyr Leu Thr Glu Lys Lys Tyr Ser Pro Cys Ala Trp Glu Val Val
130                 135                 140

Arg Ala Glu Ile Met Arg Ser Phe Ser Leu Ser Thr Asn Leu Gln Glu
145                 150                 155                 160

Arg Leu Arg Arg Lys Glu
            165
```

<210> SEQ ID NO 19

```
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 19
agagaggctg aagct                                                    15

<210> SEQ ID NO 20
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 20

Arg Glu Ala Glu Ala
1               5

<210> SEQ ID NO 21
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 21
catcaccatc accatcacta a                                             21

<210> SEQ ID NO 22
<211> LENGTH: 10
<212> TYPE: DNA
<213> ORGANISM: Artificial Sequence
<220> FEATURE:
<223> OTHER INFORMATION: Synthetic Polynucleotide

<400> SEQUENCE: 22
gtttgtagcc                                                          10

<210> SEQ ID NO 23
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 23

Glu Glu Phe Gly Asn Gln
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 24

Glu Glu Phe Asp Gly Asn Gln
1               5

<210> SEQ ID NO 25
<211> LENGTH: 5
<212> TYPE: PRT
<213> ORGANISM: Artificial Sequence
<220> FEATURE:
```

<223> OTHER INFORMATION: Synthetic Polypeptide

<400> SEQUENCE: 25

Gly Glu Gly Gly Ser
1               5

<210> SEQ ID NO 26
<211> LENGTH: 105
<212> TYPE: DNA
<213> ORGANISM: Artificial Sequence
<220> FEATURE:
<223> OTHER INFORMATION: Synthetic Polynucleotide

<400> SEQUENCE: 26
ggtgaaggag ggtcaggtga aggttcctcc ggtgagggtt cctcatccga aggggagga        60 tctgaaggcg gtggctctga gggtggaggt tcagaggag ggtca                      105

<210> SEQ ID NO 27
<211> LENGTH: 35
<212> TYPE: PRT
<213> ORGANISM: Artificial Sequence
<220> FEATURE:
<223> OTHER INFORMATION: Synthetic Polypeptide

<400> SEQUENCE: 27

Gly Glu Gly Gly Ser Glu Gly Gly Ser Glu Gly Ser Gly Glu Ser Ser
1               5                   10                  15

Gly Glu Gly Gly Ser Glu Gly Ser Glu Gly Ser Gly Glu Ser Gly
                20                  25                  30

Gly Glu Ser
        35

<210> SEQ ID NO 28
<211> LENGTH: 105
<212> TYPE: DNA
<213> ORGANISM: Artificial Sequence
<220> FEATURE:
<223> OTHER INFORMATION: Synthetic Polynucleotide

<400> SEQUENCE: 28
ggtgaaggag ggtcagaagg aggttccgag ggttctggtg aatcatccgg agaaggagga        60
tctgaaggct caggcgagtc tggtggagag tcaggggag agtca                       105

<210> SEQ ID NO 29
<211> LENGTH: 166
<212> TYPE: PRT
<213> ORGANISM: Artificial Sequence
<220> FEATURE:
<223> OTHER INFORMATION: Synthetic Polypeptide

<400> SEQUENCE: 29

Cys Asp Leu Pro Gln Thr His Ser Leu Gly Asn Arg Arg Ala Leu Ile
1               5                   10                  15

Leu Leu Ala Gln Met Arg Arg Ile Ser Pro Phe Ser Cys Leu Lys Asp
                20                  25                  30

Arg His Asp Phe Glu Phe Pro Gln Glu Glu Phe Asp Asp Lys Gln Phe
                35                  40                  45

Gln Lys Ala Gln Ala Ile Ser Val Leu His Glu Met Ile Gln Gln Thr
        50                  55                  60

Phe Asn Leu Phe Ser Thr Lys Asp Ser Ser Ala Ala Leu Asp Glu Thr
65                  70                  75                  80

```
Leu Leu Asp Glu Phe Tyr Ile Glu Leu Asp Gln Gln Leu Asn Asp Leu
                 85                  90                  95

Glu Ser Cys Val Met Gln Glu Val Gly Val Ile Glu Ser Pro Leu Met
            100                 105                 110

Tyr Glu Asp Ser Ile Leu Ala Val Arg Lys Tyr Phe Gln Arg Ile Thr
        115                 120                 125

Leu Tyr Leu Thr Glu Lys Lys Tyr Ser Ser Cys Ala Trp Glu Val Val
    130                 135                 140

Arg Ala Glu Ile Met Arg Ser Phe Ser Leu Ser Ile Asn Leu Gln Lys
145                 150                 155                 160

Arg Leu Lys Ser Lys Glu
                165

<210> SEQ ID NO 30
<211> LENGTH: 165
<212> TYPE: PRT
<213> ORGANISM: Homo sapiens

<400> SEQUENCE: 30

Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 31
<211> LENGTH: 166
<212> TYPE: PRT
<213> ORGANISM: Homo sapiens

<400> SEQUENCE: 31

Cys Asp Leu Pro Glu Thr His Ser Leu Asp Asn Arg Arg Thr Leu Met
1               5                   10                  15

Leu Leu Ala Gln Met Ser Arg Ile Ser Pro Ser Ser Cys Leu Met Asp
            20                  25                  30

Arg His Asp Phe Gly Phe Pro Gln Glu Glu Phe Asp Gly Asn Gln Phe
        35                  40                  45

Gln Lys Ala Pro Ala Ile Ser Val Leu His Glu Leu Ile Gln Gln Ile
    50                  55                  60
```

Phe Asn Leu Phe Thr Thr Lys Asp Ser Ser Ala Ala Trp Asp Glu Asp
65                  70                  75                  80

Leu Leu Asp Lys Phe Cys Thr Glu Leu Tyr Gln Gln Leu Asn Asp Leu
                85                  90                  95

Glu Ala Cys Val Met Gln Glu Glu Arg Val Gly Glu Thr Pro Leu Met
            100                 105                 110

Asn Ala Asp Ser Ile Leu Ala Val Lys Lys Tyr Phe Arg Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Leu Ser Leu Ser Thr Asn Leu Gln Glu
145                 150                 155                 160

Arg Leu Arg Arg Lys Glu
                165

<210> SEQ ID NO 32
<211> LENGTH: 166
<212> TYPE: PRT
<213> ORGANISM: Homo sapiens

<400> SEQUENCE: 32

Cys Asp Leu Pro Gln Thr His Ser Leu Ser Asn Arg Arg Thr Leu Met
1               5                   10                  15

Ile Met Ala Gln Met Gly Arg Ile Ser Pro Phe Ser Cys Leu Lys Asp
            20                  25                  30

Arg His Asp Phe Gly Phe Pro Gln Glu Glu Phe Asp Gly Asn Gln Phe
        35                  40                  45

Gln Lys Ala Gln Ala Ile Ser Val Leu His Glu Met Ile Gln Gln Thr
    50                  55                  60

Phe Asn Leu Phe Ser Thr Lys Asp Ser Ser Ala Thr Trp Asp Glu Thr
65                  70                  75                  80

Leu Leu Asp Lys Phe Tyr Thr Glu Leu Tyr Gln Gln Leu Asn Asp Leu
                85                  90                  95

Glu Ala Cys Met Met Gln Glu Val Gly Val Glu Asp Thr Pro Leu Met
            100                 105                 110

Asn Val Asp Ser Ile Leu Thr Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Leu Ser Ala Asn Leu Gln Glu
145                 150                 155                 160

Arg Leu Arg Arg Lys Glu
                165

<210> SEQ ID NO 33
<211> LENGTH: 166
<212> TYPE: PRT
<213> ORGANISM: Homo sapiens

<400> SEQUENCE: 33

Cys Asp Leu Pro Gln Thr His Ser Leu Gly Asn Arg Arg Ala Leu Ile
1               5                   10                  15

Leu Leu Ala Gln Met Gly Arg Ile Ser Pro Phe Ser Cys Leu Lys Asp
            20                  25                  30

Arg His Asp Phe Gly Phe Pro Gln Glu Glu Phe Asp Gly Asn Gln Phe
        35                  40                  45

```
Gln Lys Ala Gln Ala Ile Ser Val Leu His Glu Met Ile Gln Gln Thr
         50                  55                  60

Phe Asn Leu Phe Ser Thr Lys Asp Ser Ser Ala Thr Trp Glu Gln Ser
 65                  70                  75                  80

Leu Leu Glu Lys Phe Ser Thr Glu Leu Asn Gln Gln Leu Asn Asp Leu
                 85                  90                  95

Glu Ala Cys Val Ile Gln Val Gly Val Glu Glu Thr Pro Leu Met
            100                 105                 110

Asn Val Asp Ser Ile Leu Ala Val Lys Lys Tyr Phe Gln Arg Ile Thr
            115                 120                 125

Leu Tyr Leu Thr Glu Lys Lys Tyr Ser Pro Cys Ala Trp Glu Val Val
        130                 135                 140

Arg Ala Glu Ile Met Arg Ser Phe Ser Leu Ser Lys Ile Phe Gln Glu
145                 150                 155                 160

Arg Leu Arg Arg Lys Glu
                165

<210> SEQ ID NO 34
<211> LENGTH: 166
<212> TYPE: PRT
<213> ORGANISM: Homo sapiens

<400> SEQUENCE: 34

Cys Asp Leu Pro Gln Thr His Ser Leu Gly Asn Arg Arg Ala Leu Ile
 1               5                  10                  15

Leu Leu Ala Gln Met Gly Arg Ile Ser His Phe Ser Cys Leu Lys Asp
                20                  25                  30

Arg His Asp Phe Gly Phe Pro Glu Glu Glu Phe Asp Gly His Gln Phe
            35                  40                  45

Gln Lys Ala Gln Ala Ile Ser Val Leu His Glu Met Ile Gln Gln Thr
         50                  55                  60

Phe Asn Leu Phe Ser Thr Glu Asp Ser Ser Ala Ala Trp Glu Gln Ser
 65                  70                  75                  80

Leu Leu Glu Lys Phe Ser Thr Glu Leu Tyr Gln Gln Leu Asn Asp Leu
                 85                  90                  95

Glu Ala Cys Val Ile Gln Val Gly Val Glu Glu Thr Pro Leu Met
            100                 105                 110

Asn Glu Asp Ser Ile Leu Ala Val Arg Lys Tyr Phe Gln Arg Ile Thr
            115                 120                 125

Leu Tyr Leu Thr Glu Lys Lys Tyr Ser Pro Cys Ala Trp Glu Val Val
        130                 135                 140

Arg Ala Glu Ile Met Arg Ser Leu Ser Phe Ser Thr Asn Leu Gln Lys
145                 150                 155                 160

Arg Leu Arg Arg Lys Asp
                165

<210> SEQ ID NO 35
<211> LENGTH: 166
<212> TYPE: PRT
<213> ORGANISM: Homo sapiens

<400> SEQUENCE: 35

Cys Asp Leu Pro Gln Thr His Ser Leu Gly Asn Arg Arg Ala Leu Ile
 1               5                  10                  15

Leu Leu Ala Gln Met Gly Arg Ile Ser Pro Phe Ser Cys Leu Lys Asp
                20                  25                  30
```

```
Arg His Asp Phe Gly Leu Pro Gln Glu Glu Phe Asp Gly Asn Gln Phe
            35                  40                  45

Gln Lys Thr Gln Ala Ile Ser Val Leu His Glu Met Ile Gln Gln Thr
 50                      55                  60

Phe Asn Leu Phe Ser Thr Glu Asp Ser Ser Ala Ala Trp Glu Gln Ser
65                   70                  75                  80

Leu Leu Glu Lys Phe Ser Thr Glu Leu Tyr Gln Gln Leu Asn Asn Leu
                85                  90                  95

Glu Ala Cys Val Ile Gln Glu Val Gly Met Glu Thr Pro Leu Met
            100                 105                 110

Asn Glu Asp Ser Ile Leu Ala Val Arg Lys Tyr Phe Gln Arg Ile Thr
            115                 120                 125

Leu Tyr Leu Thr Glu Lys Lys Tyr Ser Pro Cys Ala Trp Glu Val Val
            130                 135                 140

Arg Ala Glu Ile Met Arg Ser Leu Ser Phe Ser Thr Asn Leu Gln Lys
145                 150                 155                 160

Arg Leu Arg Arg Lys Asp
                165

<210> SEQ ID NO 36
<211> LENGTH: 166
<212> TYPE: PRT
<213> ORGANISM: Homo sapiens

<400> SEQUENCE: 36

Cys Asp Leu Pro Gln Thr His Ser Leu Gly His Arg Arg Thr Met Met
 1               5                  10                  15

Leu Leu Ala Gln Met Arg Arg Ile Ser Leu Phe Ser Cys Leu Lys Asp
                20                  25                  30

Arg His Asp Phe Arg Phe Pro Gln Glu Glu Phe Asp Gly Asn Gln Phe
            35                  40                  45

Gln Lys Ala Glu Ala Ile Ser Val Leu His Glu Val Ile Gln Gln Thr
 50                      55                  60

Phe Asn Leu Phe Ser Thr Lys Asp Ser Ser Val Ala Trp Asp Glu Arg
65                   70                  75                  80

Leu Leu Asp Lys Leu Tyr Thr Glu Leu Tyr Gln Gln Leu Asn Asp Leu
                85                  90                  95

Glu Ala Cys Val Met Gln Glu Val Trp Val Gly Gly Thr Pro Leu Met
            100                 105                 110

Asn Glu Asp Ser Ile Leu Ala Val Arg Lys Tyr Phe Gln Arg Ile Thr
            115                 120                 125

Leu Tyr Leu Thr Glu Lys Lys Tyr Ser Pro Cys Ala Trp Glu Val Val
            130                 135                 140

Arg Ala Glu Ile Met Arg Ser Phe Ser Ser Arg Asn Leu Gln Glu
145                 150                 155                 160

Arg Leu Arg Arg Lys Glu
                165

<210> SEQ ID NO 37
<211> LENGTH: 166
<212> TYPE: PRT
<213> ORGANISM: Homo sapiens

<400> SEQUENCE: 37

Cys Asn Leu Ser Gln Thr His Ser Leu Asn Asn Arg Arg Thr Leu Met
 1               5                  10                  15
```

Leu Met Ala Gln Met Arg Arg Ile Ser Pro Phe Ser Cys Leu Lys Asp
                20                  25                  30

Arg His Asp Phe Glu Phe Pro Gln Glu Glu Phe Asp Gly Asn Gln Phe
            35                  40                  45

Gln Lys Ala Gln Ala Ile Ser Val Leu His Glu Met Met Gln Gln Thr
    50                  55                  60

Phe Asn Leu Phe Ser Thr Lys Asn Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Ile Gln Glu Val Gly Val Glu Glu Thr Pro Leu Met
            100                 105                 110

Asn Glu Asp Ser Ile Leu Ala Val Lys Lys Tyr Phe Gln Arg Ile Thr
        115                 120                 125

Leu Tyr Leu Met Glu Lys Lys Tyr Ser Pro Cys Ala Trp Glu Val Val
    130                 135                 140

Arg Ala Glu Ile Met Arg Ser Leu Ser Phe Ser Thr Asn Leu Gln Lys
145                 150                 155                 160

Arg Leu Arg Arg Lys Asp
                165

<210> SEQ ID NO 38
<211> LENGTH: 166
<212> TYPE: PRT
<213> ORGANISM: Homo sapiens

<400> SEQUENCE: 38

Cys Asp Leu Pro Gln Thr His Ser Leu Gly Asn Arg Arg Ala Leu Ile
1               5                   10                  15

Leu Leu Gly Gln Met Gly Arg Ile Ser Pro Phe Ser Cys Leu Lys Asp
                20                  25                  30

Arg His Asp Phe Arg Ile Pro Gln Glu Glu Phe Asp Gly Asn Gln Phe
            35                  40                  45

Gln Lys Ala Gln Ala Ile Ser Val Leu His Glu Met Ile Gln Gln Thr
    50                  55                  60

Phe Asn Leu Phe Ser Thr Glu Asp Ser Ser Ala Ala Trp Glu Gln Ser
65                  70                  75                  80

Leu Leu Glu Lys Phe Ser Thr Glu Leu Tyr Gln Gln Leu Asn Asp Leu
                85                  90                  95

Glu Ala Cys Val Ile Gln Glu Val Gly Val Glu Glu Thr Pro Leu Met
            100                 105                 110

Asn Glu Asp Ser Ile Leu Ala Val Arg Lys Tyr Phe Gln Arg Ile Thr
        115                 120                 125

Leu Tyr Leu Ile Glu Arg Lys Tyr Ser Pro Cys Ala Trp Glu Val Val
    130                 135                 140

Arg Ala Glu Ile Met Arg Ser Leu Ser Phe Ser Thr Asn Leu Gln Lys
145                 150                 155                 160

Arg Leu Arg Arg Lys Asp
                165

<210> SEQ ID NO 39
<211> LENGTH: 165
<212> TYPE: PRT
<213> ORGANISM: Homo sapiens

<400> SEQUENCE: 39

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
            35                  40                  45

Lys Ala Glu Thr Ile Pro Val Leu His Glu Met Ile Gln Gln Ile Phe
50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
            85                  90                  95

Ala Cys Val Ile Gln Gly Val Gly Val Thr Glu Thr Pro Leu Met Asn
            100                 105                 110

Glu Asp Ser Ile Leu Ala Val Arg Lys Tyr Phe Gln Arg Ile Thr Leu
            115                 120                 125

Tyr Leu Lys Glu Lys Lys Tyr Ser Pro Cys Ala Trp Glu Val Val Arg
130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 40
<211> LENGTH: 166
<212> TYPE: PRT
<213> ORGANISM: Homo sapiens

<400> SEQUENCE: 40

Cys Asp Leu Pro Gln Thr His Ser Leu Gly Asn Arg Arg Ala Leu Ile
1               5                   10                  15

Leu Leu Ala Gln Met Gly Arg Ile Ser His Phe Ser Cys Leu Lys Asp
            20                  25                  30

Arg Tyr Asp Phe Gly Phe Pro Gln Glu Val Phe Asp Gly Asn Gln Phe
            35                  40                  45

Gln Lys Ala Gln Ala Ile Ser Ala Phe His Glu Met Ile Gln Gln Thr
50                  55                  60

Phe Asn Leu Phe Ser Thr Lys Asp Ser Ser Ala Ala Trp Asp Glu Thr
65                  70                  75                  80

Leu Leu Asp Lys Phe Tyr Ile Glu Leu Phe Gln Gln Leu Asn Asp Leu
            85                  90                  95

Glu Ala Cys Val Thr Gln Glu Val Gly Val Glu Glu Ile Ala Leu Met
            100                 105                 110

Asn Glu Asp Ser Ile Leu Ala Val Arg Lys Tyr Phe Gln Arg Ile Thr
            115                 120                 125

Leu Tyr Leu Met Gly Lys Lys Tyr Ser Pro Cys Ala Trp Glu Val Val
130                 135                 140

Arg Ala Glu Ile Met Arg Ser Phe Ser Phe Ser Thr Asn Leu Gln Lys
145                 150                 155                 160

Gly Leu Arg Arg Lys Asp
                165

FUSION PROTEINS FOR TREATING CANCER AND RELATED METHODS

CROSS-REFERENCE TO RELATED APPLICATIONS

This application is a continuation under 35 U.S.C. § 120 of co-pending U.S. application Ser. No. 15/307,646 filed Oct. 28, 2016, which is a national stage filing under 35 U.S.C. § 371 of international application PCT/US2015/028653 filed Apr. 30, 2015 which designates the U.S. and claims benefit under 35 U.S.C. § 119(e) of U.S. Provisional Application No. 61/986,866, filed Apr. 30, 2014, which are incorporated by reference herein in their entireties.

SEQUENCE LISTING

The instant application contains a Sequence Listing which has been submitted electronically in ASCII format and is hereby incorporated by reference in its entirety. Said ASCII copy, created on Apr. 5, 2019, is named 2019-04-05-Sequence-Listing-002806-089103USC1.txt and is 54,595 bytes in size.

BACKGROUND OF INVENTION

Previous work indicated the value of combining a targeting element having a high affinity for a cell surface receptor and an activity element having a lower affinity for a second cell surface receptor through which signaling occurs (for example by fusion of protein domains via a linker). A mutation may be introduced into the activity element to reduce its receptor binding so that its binding affinity is below that of the targeting element for its receptor. This approach has been shown to enhance the specificity of an activity element for target cells relative to side effect cells by as much as 20-fold, with some specificity enhancement attributable to the attached targeting element and the activity-reducing mutation.

However, in some therapeutic settings, the desired target cell is much less accessible than cells through which adverse side effects are mediated. For example, solid tumors often lack lymph node drainage, therefore therapeutic proteins that enter from the circulation only perfuse the tumor by diffusion. This results in the concentration of the therapeutic fusion protein being many times greater in the vicinity of side-effect cells, such as normal tissue, compared to target cells, such as tumor cells. In addition to tumors, targeting of proteins to the brain also results in limited access by therapeutic proteins due to the blood-brain barrier. Therefore, there is a need in the art for improved approaches to targeting of therapeutic protein activities, as well as for therapeutic proteins with enhanced specificity for their target cells.

SUMMARY

This disclosure relates to protein engineering and construction of fusion proteins. Some aspects of the present disclosure focus on improving the properties of a class of engineered fusion proteins termed "chimeric activators." These proteins include a targeting element that binds to a cell surface receptor, an activity element that binds to a distinct receptor on the same cell, and a linker connecting the two protein domains. In some embodiments, the activity element has reduced activity due to the presence of one or more amino acid substitutions. In some embodiments, decreasing the binding affinity of the activity element in an effort to reduce undesired side effects (e.g., anti-proliferative or cytotoxic effects on non-target cells) can render the chimeric molecules ineffective due to weak receptor binding, such that the targeting receptor-bound chimeric activator may be internalized and degraded through normal membrane clearance phenomena before signaling has a chance to occur. Aspects of the present disclosure are based in part on the recognition that many signaling molecules bind to more than one receptor or receptor subunit, the interactions with these receptors vary in strength by several orders of magnitude, and that these differences can be taken into account when designing or producing a chimeric activator as described herein.

In some embodiments, aspects of the disclosure relate to fusion proteins comprising a first protein domain that binds to a multisubunit signaling receptor (e.g., a cell surface multi subunit signaling receptor), a second protein domain (e.g., an antibody variable region element, a ligand, or other peptide) that binds to a cell surface antigen, and a linker that connects the first protein domain and the second protein domain, wherein the first protein domain that binds to the multimeric signaling receptor includes a first amino acid substitution and a second amino acid substitution such that the binding affinity of the first protein domain to a first subunit of the multisubunit signaling receptor is altered by the first amino acid substitution and the binding affinity of the first protein domain to a second subunit of the multisubunit signaling receptor is altered by the second amino acid substitution.

In some embodiments, the fusion protein comprises one polypeptide chain. In some embodiments, the multisubunit signaling receptor and the cell surface antigen are expressed on at least one cell type in a human. In some embodiments, the first mutation decreases the binding affinity of the first protein domain for the first receptor subunit and the second mutation increases the affinity of the first protein domain for the second receptor subunit. In some embodiments, the multisubunit signaling receptor is a Type 1 interferon receptor. In some embodiments, the protein domain that binds to a multisubunit signaling receptor is a cytokine or hormone. In some embodiments, this protein domain comprises a Type 1 interferon. In some embodiments, the Type 1 interferon comprises one or more amino acid substitutions selected from the group consisting of L30A, R145A, M149A, E59A, H58A, and R150A.

In some embodiments, an antibody variable region element comprises an antibody variable region or regions or a derivative or fragment thereof that is capable of binding a peptide provided by the amino acid sequence Lys-Gly-Asn-Tyr-Val-Val-Thr-Asp-His (SEQ ID NO: 17). In some embodiments, the protein domain that binds to the multisubunit signaling receptor comprises the amino acid sequence provided by SEQ ID NO: 18.

In some embodiments, the linker connects the C-terminal end of second protein domain (e.g., the antibody or antibody variable region element) to the N-terminal end of the first protein domain. In some embodiments, the linker connects the C-terminal end of the first protein domain to the N-terminal end of the second protein domain (e.g., the antibody or antibody variable region element). In some embodiments, the first protein domain inhibits cellular proliferation. In some embodiments, the antibody variable region element comprises a heavy chain variable region comprising the amino acid sequence provided by SEQ ID NO: 15 and a light chain variable region comprising the amino acid sequence provided by SEQ ID NO: 16. In some embodiments, the Type 1 interferon comprises mutations H58A and R150A.

In some embodiments, the Type 1 interferon comprises mutations E59A and M149A.

In some embodiments, aspects of the disclosure relate to a fusion protein (e.g., a chimeric activator) comprising a polypeptide that binds to a heteromultimeric receptor comprising at least a first subunit and a second subunit, a second protein domain (e.g., an antibody variable region element, a ligand, or other peptide) that binds to a target cell surface receptor (e.g., EGFRvIII), and a linker that connects the polypeptide and the antibody variable region element. In some embodiments, the polypeptide that binds to the heteromultimeric receptor includes one or more amino acid substitutions such that the binding affinity of the polypeptide to a first subunit of the heteromultimeric receptor is increased and/or the binding affinity of the polypeptide to a second subunit of the heteromultimeric receptor is decreased (e.g., such that the relative binding affinities of the polypeptide to each receptor is less than 10 fold, 5 fold, 2 fold, or 1.5 fold, or 1.1 fold of each other). In some embodiments, a fusion protein includes a polypeptide (e.g., a first protein domain) having at least one amino acid substitution such that the binding affinity of the polypeptide to at least one subunit of the heteromultimeric receptor is increased relative to binding affinity of the unsubstituted polypeptide.

In the case of Type 1 interferons, the interaction with the Type 1 interferon receptor subunit 2 (IFNAR2) is much stronger than with the Type 1 interferon receptor subunit 1 (IFNAR1). In a binding model contemplated by the present disclosure, a polypeptide such as an interferon (IFN) initially bind to IFNAR2, and then the IFN/IFNAR2 complex diffuses in two dimensions in the cell membrane until it finds IFNAR1. A stable signaling complex is formed after formation of the IFNAR1/IFNAR2/IFN trimeric complex, and subsequent intracellular events occur such as binding of downstream signaling proteins and phosphorylation. According to this model, the IFNAR1/IFNAR2/IFN trimeric complex may dissociate before intracellular events occur.

In some embodiments, the polypeptide that binds to the Type 1 interferon receptor comprises a Type 1 interferon-a region having one or more substitution mutations in a portion of the polypeptide that interacts with the receptor. For example, in some embodiments one or more substitution mutations are selected from the group consisting of L30A, R145A, M149A, E59A, H58A, and R150A (e.g., both M149A and E59A and/or both H58A and R150A).

In some embodiments, the heteromultimeric receptor is a Type 1 interferon receptor. In some embodiments, the amino acid sequence of the polypeptide that binds to the heteromultimeric receptor is an interferon and comprises one or more amino acid substitutions that improve expression, stability (e.g., structural stability and/or resistance to intracellular degradation for example associated with cellular internalization), or signaling of the polypeptide. In some embodiments, such substitutions in the polypeptide backbone result in the presence of one or more of Arg at residue 23, Pro at residue 26, Asp at residue 44, Gln at residue 52, Ala at residue 53, Ser at residue 55, Glu at residue 83, Thr at residue 101, Val at residue 104, Gly at residue 105, Glu at residue 107, and/or Glu at residue 125 as described herein. In some embodiments, one or more of these backbone substitutions may enhance binding of the polypeptide to the first and second subunit of the heteromultimeric receptor and increase stability of the trimeric signaling complex. In some embodiments, one or more of these substitutions increase resistance of the trimeric complex to internalization and degradation.

In some embodiments, the antibody variable region element that binds to EGFRvIII comprises MR1-1 or a derivative or fragment thereof In some embodiments, the linker has a net charge.

In some embodiments, aspects of the disclosure relate to fusion proteins comprising a protein domain that binds to a multisubunit signaling receptor, a second protein domain (e.g., an antibody variable region element) that binds to a cell surface antigen, and a linker that connects the protein domain and the second protein domain (e.g., the antibody variable region element), wherein the linker is a peptide linker and has a net charge. In some embodiments, the net charge of the linker is negative. In some embodiments, the linker comprises amino acids selected from the group consisting of glycine, serine, glutamate, and aspartate. In some embodiments, the net charge of the linker is positive. In some embodiments, the linker comprises amino acids selected from the group consisting of lysine, arginine, and histidine.

In some embodiments, the linker comprises 10 to 200 amino acids in length. In some embodiments, the linker comprises a repeat of GGGSE (SEQ ID NO:11), GSESG (SEQ ID NO:12), or GSEGS (SEQ ID NO:13). In some embodiments, the linker comprises the sequence of GEGGS-GEGSSGEGSSSEGGGSEGGGSEGGGSEGGS (SEQ ID NO:14).

In some embodiments, the linker comprises an amino acid sequence comprising regularly spaced negatively charged amino acids and non-regularly spaced non-charged amino acids. In some embodiments, the non-charged amino acids are selected from the group consisting of glycine, serine, alanine, proline, and threonine. In some embodiments, the non-charged amino acids are selected from the group consisting of glycine and serine.

In some embodiments, the protein domain that binds to the multisubunit signaling receptor is a cytokine or hormone. In some embodiments, the protein domain that binds to the multi-subunit signaling receptor is a Type 1 interferon. In some embodiments, the protein domain that binds to the multisubunit signaling receptor comprises the amino acid sequence provided by SEQ ID NO: 18. In some embodiments, the linker connects the C-terminal end of the antibody variable region element to the N-terminal end of the protein domain. In some embodiments, the linker connects the C-terminal end of the protein domain to the N-terminal end of the antibody or antibody variable region element. In some embodiments, the protein domain inhibits cellular proliferation.

In some embodiments, the antibody variable region element comprises a heavy chain variable region comprising the amino acid sequence provided by SEQ ID NO: 15 and a light chain variable region comprising the amino acid sequence provided by SEQ ID NO: 16. In some embodiments, the Type 1 interferon comprises mutations H58A and R150A. In some embodiments, the Type 1 interferon comprises mutations E59A and M149A.

In some embodiments, the fusion protein selectively binds to cancer cells relative to non-cancer cells. In some embodiments, the fusion protein selectively binds to cancer cells that express EGFRvIII relative to cells that do not express EGFRvIII. Accordingly, some aspects of the disclosure relate to a chimeric activator comprising a polypeptide that binds to a Type 1 interferon receptor, an antibody that binds to EGFRvIII, and a linker that connects the polypeptide and the antibody. In some embodiments, the linker is a peptide linker and has a net charge. In some embodiments, the polypeptide that binds to the Type 1 interferon receptor comprises one or more amino acid substitutions that improve expression, stability, or signaling of the polypeptide. In some embodiments, the polypeptide that binds to the Type 1 interferon receptor comprises a Type 1 interferon-a (IFN-a) region having one or more substitution mutations selected from the group consisting of L30A, R145A, M149A, E59A, H58A, and R150A (e.g., both M149A and E59A and/or both H58A and R150A). In some embodiments, the antibody that binds to EGFRvIII comprises MR1-1 or a derivative or fragment thereof.

In some embodiments, the Type 1 interferon-a comprises one or more amino acid substitutions in the polypeptide that result in Arg at residue 23, Pro at residue 26, Asp at residue 44, Gln at residue 52, Ala at residue 53, Ser at residue 55, Glu at residue 83, Thr at residue 101, Val at residue 104, Gly at residue 105, Glu at residue 107, and/or Glu at residue 125, or any combination thereof.

In some embodiments, the linker connects the C-terminal end of the antibody or antibody variable region element to the N-terminal end of the polypeptide. In other embodiments, the linker connects the C-terminal end of the polypeptide to the N-terminal end of the antibody or antibody variable region element.

In some embodiments, the antibody or antibody variable region element that binds to EGFRvIII comprises a svFc, sdAb, Fab, Fab2, or a full length immunoglobulin (e.g., a full length immunoglobulin chain, for example a heavy chain and/or a light chain). In some embodiments, the antibody or antibody variable region element comprises a heavy chain variable region of SEQ ID NO: 15 and a light chain variable region of SEQ ID NO: 16.

In some embodiments, the Type 1 interferon comprises mutations H58A and R150A

In other embodiments, the Type 1 interferon comprises mutations E59A and M149A.

In some embodiments, the linker comprises 10 to 200 amino acids in length. In some embodiments, the net charge of the linker is negative. In some embodiments, the linker comprises amino acids selected from the group consisting of glycine, serine, glutamate, and aspartate. In some embodiments, the linker comprises a repeat of GGGSE (SEQ ID NO:11), GSESG (SEQ ID NO:12), or GSEGS (SEQ ID NO:13). In some embodiments, the linker comprises the sequence GEGGSGEGSSGEGSSSEGGGSEGGGSEGGGSEGGS (SEQ ID NO:14).

In other embodiments, the net charge of the linker is positive. In other embodiments, the linker comprises amino acids selected from the group consisting of lysine, argininc, and histidine.

In some embodiments, the chimeric activator selectively binds to cancer cells relative to non-cancer cells. In some embodiments, the chimeric activator protein selectively binds to cancer cells that express EGFRvIII relative to cells that do not express EGFRvIII.

Aspects of the disclosure relate to isolated proteins comprising SEQ ID NO: 18. Accordingly, in some embodiments aspects of the disclosure relate to an isolated chimeric activator protein comprising an amino acid sequence selected from the group consisting of SEQ ID NO: 1 [MR1-1 IFNa 2-1b WT], SEQ ID NO: 2 [MR1-1 IFNa 2-1B L30A], SEQ ID NO: 3 [MR1-1 IFNa 2-1B R145A], SEQ ID NO: 4 [MR1-1 IFNa 2-1b E59A M149A], and SEQ ID NO: 5[MR1-1 IFNa 2-1b H58A R150A].

Aspects of the disclosure relate to isolated nucleic acids that encode any of the fusion proteins described above and elsewhere here. In some embodiments, the isolated nucleic acid comprises in frame a first sequence encoding a protein domain that binds to a multisubunit signaling receptor, a second sequence encoding an antibody variable region element that binds a cell surface antigen, and a third sequence encoding a linker that connects the protein domain and the antibody variable region element, wherein the linker is a peptide linker and has a net charge.

Other aspects of the disclosure relate to an isolated nucleic acid that encodes a chimeric activator protein as described above or elsewhere herein.

In some embodiments, aspects of the disclosure relate to an isolated nucleic acid encoding a chimeric activator comprising in frame a first sequence encoding a polypeptide that binds to a Type 1 interferon receptor, a second sequence encoding an antibody that binds to EGFRvIll, and a third sequence encoding a linker that connects the polypeptide and the antibody. In some embodiments, the linker is a peptide linker and has a net charge. In some embodiments, the polypeptide that binds to the Type 1 interferon receptor comprises a Type 1 interferon-a (IFN-a) region having one or more substitution mutation selected from the group consisting of L30A, R145A, M149A, E59A (e.g., both M149A and E59A), H58A, and R150A (e.g., both H58A and R150A). In some embodiments, the antibody that binds EGFRvIII comprises MR1-1 or a derivative or fragment thereof.

Aspects of the disclosure relate to methods for manufacturing a fusion protein comprising a protein domain that binds to a multisubunit signaling receptor, an antibody variable region element that binds to a cell surface antigen, and a linker that connects the protein domain and the antibody variable region element, comprising mutating the protein domain such that the binding affinity of the protein domain to a first subunit of the multisubunit signaling receptor is increased and the binding affinity of the protein domain to a second subunit of the multisubunit signaling receptor is decreased relative to an unmutated protein domain; selecting a linker length and an amino acid composition that enhances the specificity of the fusion protein for cells bearing the cell surface antigen; and preparing the fusion protein. In some embodiments, the first subunit is IFNAR1 and the second subunit is IFNAR2.

Other aspects of the disclosure relate to methods for manufacturing a chimeric activator comprising a polypeptide that binds to the Type 1 interferon receptor, an antibody fragment that binds to EGFRvIII, and a linker that connects the polypeptide and the antibody fragment. In some embodiments, the method involves mutating the polypeptide such that the binding affinity of the polypeptide to a first subunit of the Type 1 interferon receptor is increased and the binding affinity of the polypeptide to a second subunit of the Type 1 interferon receptor is decreased. In some embodiments, the method involves selecting a linker length and/or an amino acid composition that stabilizes and/or increases the activity of the chimeric activator (e.g., after internalization). In some embodiments, the method involves preparing a chimeric activator. In some embodiments, the chimeric activator binds to two subunits of a Type 1 interferon receptor. In some embodiments, the first subunit is IFNAR1 and the second subunit is IFNAR2.

Aspects of the disclosure relate to methods for targeted inhibition of cellular proliferation comprising contacting a cell with an effective amount of any of the fusion proteins described above and elsewhere herein. In some embodiments, the cell is characterized by expression of EGFRvIIl. In some embodiments, the cell is in a human. In some embodiments, the cell is obtained from a human.

Some aspects of the disclosure relate to methods for targeted inhibition of cellular proliferation. In some embodiments, the method involves contacting a cell with an effective amount of a fusion protein (e.g., a chimeric activator). In some embodiments, the method involves assessing cellular proliferation after contacting the cell with the fusion protein (e.g., chimeric activator). In some embodiments, the cell is characterized by expression of EGFRvIII. In some embodiments, the cell is in an individual (e.g., in situ, in vivo). In other embodiments, the cell is obtained from an individual (e.g., ex vivo).

Aspects of the disclosure relate to methods for treating cancer comprising administering to an individual having cancer an effective amount of any of the fusion proteins described above or elsewhere herein. In some embodiments, the cancer is characterized by EGFRvIII expression. In some embodiments, the cancer is glioblastoma. In some embodiments, the individual has received at least one cancer treatment selected from the group consisting of surgery, chemotherapy, and radiation therapy. In some embodiments, the individual is concurrently administered the fusion protein and at least one cancer treatment selected from the group consisting of surgery, chemotherapy, and radiation therapy.

Some aspects of the disclosure relate to methods for treating cancer. In some embodiments, the method involves administering to an individual having cancer an effective amount of a fusion protein (e.g., a chimeric activator). In some embodiments, the cancer is characterized by EGFRvIII expression. In some embodiments, the cancer is glioblastoma. Other aspects of the disclosure relate to methods for treating an individual having cancer. In some embodiments, the method involves detecting whether the cancer expresses EGFRvIII, and if EGFRvIII expression is detected, administering to the individual an effective amount of a chimeric activator.

Yet other aspects of the disclosure relate to compositions comprising any of the fusion proteins described above or elsewhere herein. In some embodiments, the composition also comprises a pharmaceutically acceptable carrier, wherein the pharmaceutically acceptable carrier comprises a phosphate-buffered saline or a buffer comprising a sugar, arginine, citrate, and/or a Tween compound.

Other aspects of the disclosure provide compositions comprising a chimeric activator as described herein. In some embodiments, the composition further comprises a pharmaceutically acceptable carrier. In some embodiments, the pharmaceutically acceptable carrier comprises a phosphate-buffered saline or a buffer comprising a sugar, arginine, citrate, and/or a Tween compound.

BRIEF DESCRIPTION OF DRAWINGS

The following drawings form part of the present specification and are included to further demonstrate certain aspects of the present disclosure, which can be better understood by reference to one of more of these drawings in combination with the detailed description of the specific embodiments presented herein.

FIG. 1A presents the general structure of a fusion protein comprising an activity element, a negatively charged linker, and a targeting element. FIG. 1B presents an example of a fusion protein comprising an activity element, a negatively charged linker, and an activity element consisting of a single-chain Fv (scFv) that includes a linker between the VH and VL domains. FIG. 1C presents an example of a fusion protein comprising an activity element with a mutation (indicated by an "X") that reduces its binding to a receptor, a negatively charged linker, and an activity element consisting of an (scFv) that includes a linker between the VH and VL domains. FIG. 1D presents an example of a fusion protein comprising an activity element fused to a "SNAP" protein domain, a negatively charged linker consisting of a nucleic acid attached at one end to the SNAP domain, and an activity element consisting of a second SNAP domain fused to a single-chain Fv (scFv) with a linker between the VH and VL domains such that the second SNAP domain is also attached to the other end of the nucleic acid. FIG. 1E is a schematic demonstrating the repulsive electrostatic interaction between the surface of a cell, which is negatively charged, and negative charges on a linker in a fusion protein that includes an activity element and a targeting element.

FIGS. 2A-2C presents example sequences of a negatively charged peptide linker, consisting of glycine, serine, and glutamic acid residues. FIG. 2A shows a fusion protein with the negatively charged linker highlighted by a bracket. FIG. 2B presents an exemplary 35-amino acid linker sequence (SEQ ID NO. 14) with randomly placed glycine and serine residues and glutamic acid residues at regular five amino acid intervals. The DNA sequence corresponds to SEQ ID NO: 26. FIG. 2C presents an exemplary 35-amino acid linker sequence with randomly placed glycinc and serine residues and glutamic acid residues at regular four-amino acid intervals (SEQ ID NO: 27). The DNA sequence corresponds to SEQ ID NO: 28. The coding sequences of the linkers are also shown and indicate how non-repetitive encoding is accomplished.

FIGS. 3A-3F present example fusion proteins with an activity element (A), a linker (indicated by a line), and a targeting element (T), in which the activity element binds to at least two different receptor subunits on a cell surface to achieve signaling; and the binding is through two different faces whose receptor subunit binding can be independently modulated. FIG. 3A presents an example fusion protein that is simultaneously bound to a targeting receptor ($Rec_T$) and an activity element receptor with two subunits ($R1_A$ and $R2_A$). FIG. 3B presents the general structure of a fusion protein with an activity element, a linker, and a targeting element, in which the activity element contains one or more mutations (indicated by an "X") on each protein face that interacts with one of the receptor subunits (and thus contains at least two mutations). FIG. 3C presents an example fusion protein in which the mutation(s) on one face of the activity element have the net effect of increasing binding to a receptor subunit (indicated by an "X+"), and mutations on another face also have the effect of increasing binding but to a distinct receptor subunit (also indicated by an "X+"). FIG. 3D presents an example fusion protein in which the mutation (s) on one face of the activity element have the net effect of increasing binding to a receptor subunit (indicated by an "X+"), and mutations on another face have the effect of decreasing binding to a distinct receptor subunit (indicated by an "X−"). FIG. 3E presents such an example fusion protein in which the mutation(s) on one face of the activity element have the net effect of decreasing binding to a receptor subunit (indicated by an "X"), and mutations on another face also have the effect of decreasing binding but to a distinct receptor subunit (indicated by an "X"). FIG. 3F shows a table of the binding dissociation constants for wild-type and mutant forms of IFN-a used in fusion proteins described in the Examples and FIG. 5, with respect to IFNAR1 ("R1") and IFNAR2 ("R2"). In fusion proteins that contain double mutations (e.g., His57Ala (H57A) Arg149Ala (R149A) and Glu58Ala (E58A) Met148Ala (M148A)), one mutation decreases binding while the other increases binding, such that the binding affinity of each face of IFNa with its receptor subunit is substantially the same.

FIG. 4 shows an alignment of human IFNa sequences, with the sequence of IFNa2-1b at the top in bold. The sequences, from top to bottom, correspond to SEQ ID NOs: 18, 30, 31, 32, 33, 34, 35, 36, 37, 38, 39, 40, and 29.

FIGS. 5A-5F present exemplary viability curves of wild-type U87 cells (diamonds) or U87 cells that express EGFR-vIII (U87 EGFRvIll; squares) following treatment for 72 hours with the indicated fusion proteins produced in *Pichia pastoris* supernatants. FIG. 5A shows viability following treatment with wild-type IFNa. FIG. 5B shows viability following treatment with MR1-1 IFNa 2-1b wt. FIG. 5C shows viability following treatment with MR1-1 IFNa 2-1b L30A. FIG. 5D shows viability following treatment with MR1-1 IFNa 2-1b R145A. FIG. 5E shows viability following treatment with MR1-1 IFNa 2-1b H58A R150A. FIG. 5F shows viability following treatment with MR1-1 IFNa 2-1b E59A M149A.

DETAILED DESCRIPTION OF INVENTION

Figure 1A:
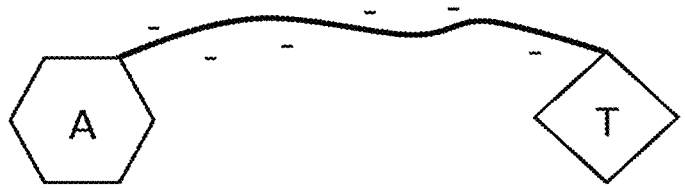
FIGS. 1A-1E present a set of example fusion proteins comprising a targeting element (T) and an activity element (A) connected by a negatively charged linker (indicated by a line).
Figure 1B:
Figure 1C:
Figure 1D:
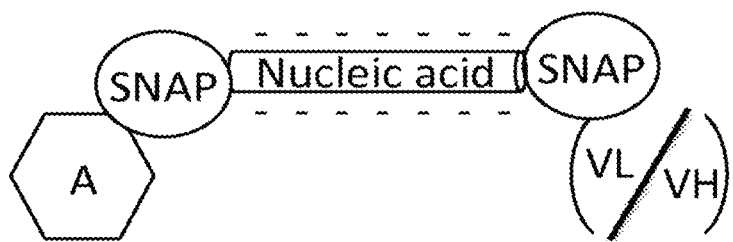
Figure 1E:
Figure 6:
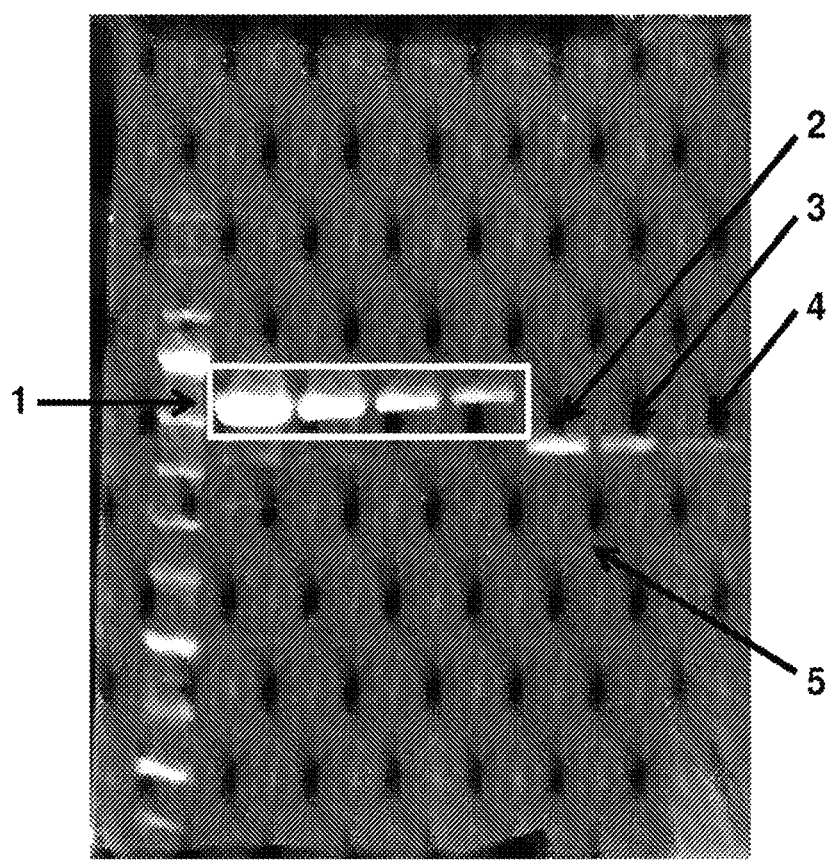
FIG. 6 shows an SDS-PAGE gel quantifying MR1-1-IFNa2-1b(R145A) production. Lane 1 contains a size standard. In lanes 2-5, 5, 2.5, 1.25 and 0.75 micrograms of bovineserum albumin (BSA) was run; the BSA is indicated by "1" and the white box. Bands in lanes 6 and 7 are samples of MR1-1-IFNa2-1b(R145A) diluted by 5-fold and 10-fold, respectively, following purified by cobalt affinity via the His6 tag and then by fast protein liquid chromatography (FPLC). Protein bands of the predicted size are indicated by "2" and "3". Lane 8 is the undiluted supernatant from the initial *Pichia pastoris* culture; and "4" represents the protein band at the predicted size. "5" indicates contaminating protein bands that constitute less than 10% of the total protein in the sample. The results indicate that the MR1-1-IFNa2-1b (R145A) protein can be purified from *Pichia pastoris* cultures using conventional methods.
Figure 7:
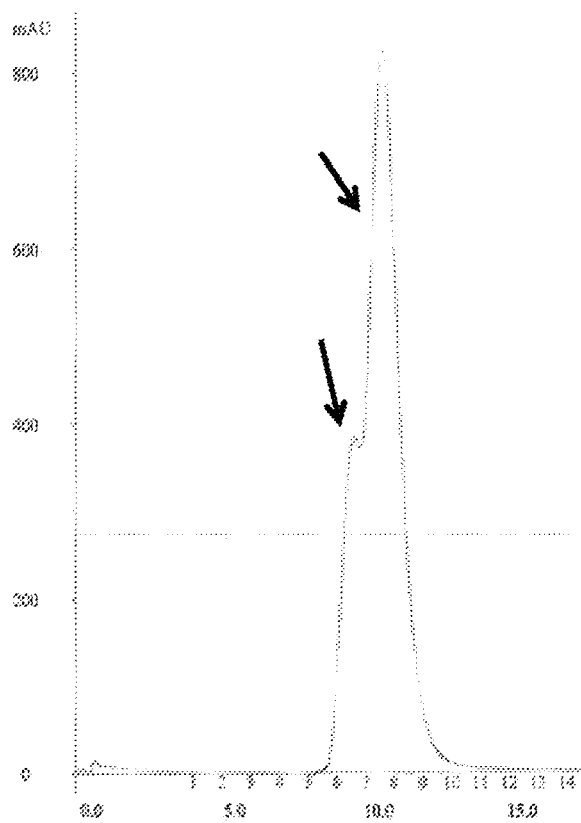
FIG. 7 shows an FPLC profile of MR1-1 IFNa2-1b (R145A). The arrows indicate the main peak and a shoulder peak representing MR1-1 IFNa2-1b (R145A). When fractions corresponding to the peak and the shoulder peak were examined by SDS-PAGE gel, both showed an identical pattern consisting of >90% MR1-1-IFNa2-1b (R145A) similar to that of FIG. 6. This result suggests that because the loaded sample was in a highly concentrated state, the scFv portion of MR1-1 IFNa2-1b (R145A) was in a monomer-dimer equilibrium and that the shoulder represents non-covalent dimeric MR1-1 IFNa2-1b (R145A).
Figure 8:
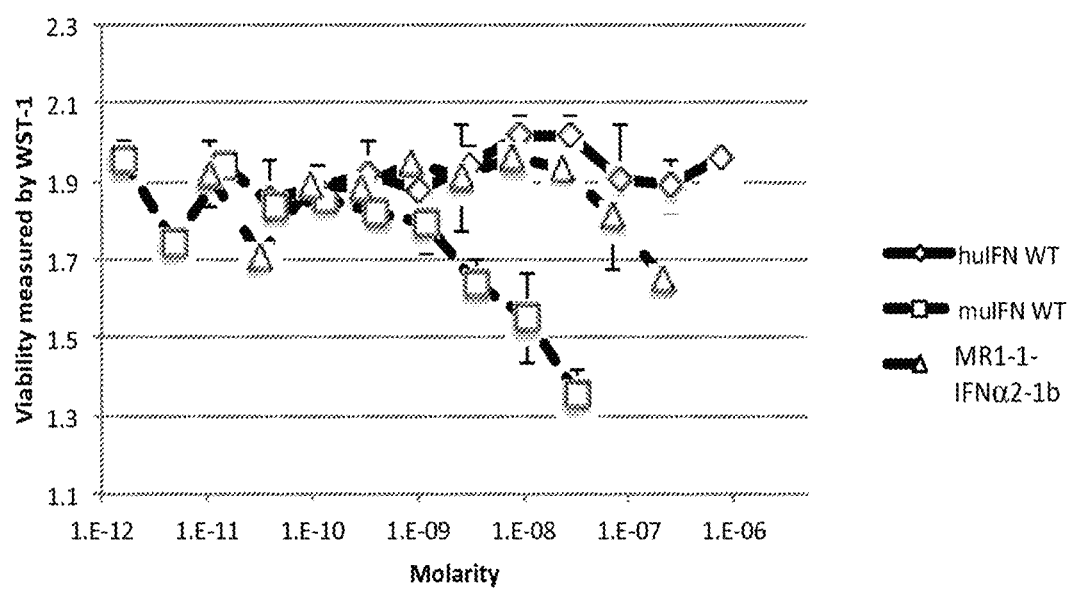
FIG. 8 shows results of a growth inhibition assay in which murine Neuro-2a cells (N2a cells) were treated with between approximately 1 picomolar to 1 micromolar murine IFN-a2 (muIFN WT), human IFN-a2a (huIFN WT), or MR1-1 IFNa-1b. The results indicate that the murine protein was most active in growth inhibition of the murine N2a cells, MR1-1 IFNa-1b was detectably active but less so than the murine IFNa, and that the human IFNa2a protein was not detectably active.
Figure 9:
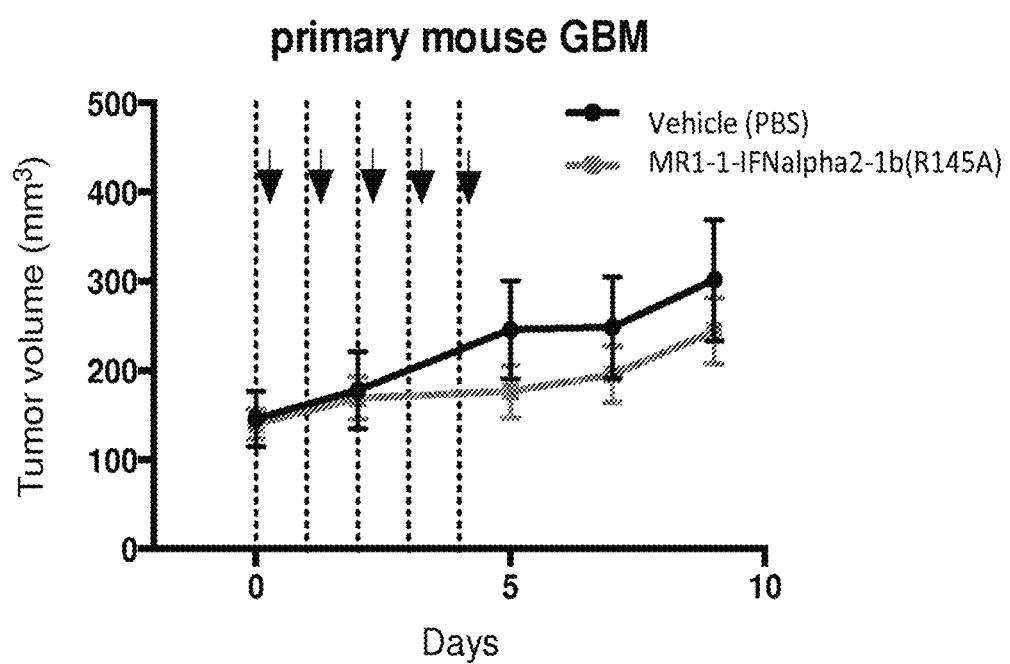
FIG. 9 shows tumor volume in mice at the indicated time points. The arrows indicate administration of the fusion protein (MR1-1-IFNa2-1b (R145a) at 135 meg/mouse/day or vehicle control (PBS). Tumors volumes were calculated by the formula (length×width)/2. Squares are mice treated with the fusion protein; and circles mice that received the control.

Aspects of the disclosure are based on the recognition that coupling a molecule with a desired activity to a targeting molecule can be an effective method for targeting the activity to cells expressing a targeted feature. However, in some therapeutic settings, the targeted cell is less accessible than cells not expressing the targeted feature. Such cells are referred to herein as "side effect cells." The desired activity performed on a side effect or non-targeted cell mediates many of the side effects of such therapeutic molecules. For example, solid tumors often lack lymph node drainage and therapeutic molecules only perfuse the tumor by diffusion. This results in a local concentration of the therapeutic molecule that is many times greater in the vicinity of side effect cells compared to target cells, such as tumor cells. In another example, therapeutic molecules that target molecules expressed by cells of the brain must cross the blood-brain barrier. A relatively low proportion of the therapeutic molecule succeeds in accessing this limited site, resulting in a much lower concentration of the therapeutic molecule contacting the targeted cells compared to the side effect cells. Accordingly, there is a need for improved and novel approaches to enhance the specificity and the desired activity of therapeutic molecules to targeted cells while minimizing any activity towards side effect cells.

Described herein are novel fusion proteins that are capable of binding two distinct targets on a cell, wherein one of the targets is a multimeric target or multi-subunit signaling protein (e.g., a heteromultimeric target). In some embodiments, the fusion proteins are also targeted to cells expressing a cell surface antigen, such as an EGFR variant, e.g., EGFRvIII, that is associated with diseases mediated by constitutive EGFR signaling, such as cancer. For example, upon targeting to EGFRvIII-expressing cells, fusion proteins can also bind to a mutisubunit signaling receptor, such as a heteromultimeric receptor, e.g., a Type 1 interferon receptor (IFNAR). Other examples of heteromultimeric receptors that can be bound by fusion proteins include, without limitation, the IL-2 receptor, IL-4 receptor, and LIF receptor.

Binding of fusion protein to a multisubunit signaling receptor can induce a desired activity in the targeted cell. For example, some fusion proteins described herein induce an anti-proliferative effect on the targeted cell and reduce undesired activity on side effect cells, providing an improved therapeutic approach to cancer treatment. In some embodiments, described herein are fusion proteins comprising an antibody region that binds EGFRv7111, a protein domain that binds to the Type 1 interferon receptor, and a linker that connects the antibody region and the protein domain, and uses thereof for inducing anti-proliferative effects in cells expressing EGFRvIII and treating disease associated with constitutive EGFR signaling due to expression of EGFRvIII. The fusion proteins described herein exhibit enhanced specificity and therapeutic activity in target cells and reduce undesired targeting of side effect cells (e.g., normal, non-cancer cells).

In some embodiments, the fusion proteins described herein are chimeric activators As used herein, a "chimeric activator" refers to an engineered protein that binds to one or more receptors or antigens on the surface of a cell. A chimeric activator includes an "activity element," a "targeting element," and a polypeptide linker that connects the activity element and the targeting element. The activity element of the chimeric activator binds to a receptor on a target cell surface and has a biological activity, such as initiation of a signal transduction pathway that may result in a desired effect. The targeting element binds to a targeting receptor on the surface of the same cell, such as a cell surface antigen. The polypeptide linker connects the activity element and the targeting element such that both the activity and targeting elements can simultaneously bind to their receptors/antigens on the surface of the same cell. In some embodiments, the chimeric activators described herein also comprise at least one mutation in the activity element that reduces its biological activity relative to the natural protein or protein domain from which it was derived.

As used herein, a "protein domain" or "domain" refers to a distinct globular unit that can be identified as such by a structure determination method such as X-ray crystallography or NMR, by other biophysical methods such as scanning calorimetry according to which a protein domain melts as a distinct unit (see for example Pabo et al. *Proc Natl Acad Sci USA.* (1979) 76(4):1608-12), or by sequence similarity to protein domains whose structure has been determined. The SCOP database (Murzin et al. *J Mol Biol.* (1995) 247(4): 536-40) provides the identification of protein domains so that the domain organization of a new protein can be identified by sequence comparison. Protein domains comprise an amino acid sequence that is sufficient to drive folding of such a polypeptide into a discrete structure, in which essentially all of the rotatable bonds along the main chain of the polypeptide are constrained to within about 10 degrees. In contrast, linkers, short peptides, molten globules, and unstructured segments are examples of polypeptides that are not domains and do not have these characteristics.

Fusion Proteins

The present disclosure provides novel fusion proteins for treating cancer. As used herein, the term "fusion protein" refers to any protein or polypeptide that is comprised of peptides, polypeptides, or protein domains from at least two different sources (e.g. two different proteins). The term fusion protein also encompasses "chimeric activators." The fusion proteins are capable of simultaneously binding to multiple unrelated receptors on the same target cell and induce a desired activity. As described herein, the fusion proteins comprise a first protein domain that binds to a multi-subunit signaling receptor, referred to as an activity element; a second protein domain (e.g., an antibody variable region element, a ligand, or other peptide) that binds to a cell surface receptor, referred to as a targeting element; and a linker that connects the activity element and the targeting element. In some embodiments, the activity element is mutated or altered so it has modified (e.g., increased or decreased) activity relative to its naturally occurring counterpart. One portion of the fusion protein functions as a targeting element and another portion of the fusion protein functions as the activity element. In some embodiments, the fusion protein is a chimeric activator comprising a protein domain that binds to Type 1 interferon receptor (IFNAR), an antibody that binds to EGFRvIII, and a linker that connects the protein domain and the antibody.

Type 1 interferons (IFN) are a subset of interferon proteins that bind to the Type 1 interferon receptor (IFNAR) complex. The IFNAR consists of two subunits IFNAR1 and IFNAR2, that upon ligand binding activate the Janus kinase (Jak) and signal transduction and activator of transcription (STAT) signaling pathway to induce expression of more than 400 IFN-regulated genes. In mammals, IFNs are further subdivided into groups IFN-a, IFN-13, IFN-K, IFN-6, IFN-E, IFN-T, IFN-w, and IFN-; IFN-a is produced by leukocytes and has at least 13 subtypes including IFN-a1, IFN-a2, IFN-a4, IFN-a5, IFN-a6, IFN-a7, IFN-a8, a10, IFN-a13, IFN-a14, IFN-a16, IFN-a17, and IFN-a21. IFN-I3 is predominantly produced by fibroblasts has two subtypes: IFN-I31 and IFN-I33. Both IFN-a and IFN-I3 are involved in the innate immune response, and upon binding to the IFNAR complex induce anti-proliferative effects and the canonical anti-viral response. Accordingly, in some embodiments, a chimeric activator can comprise any one of Type 1 interferons such that it binds to the IFNAR1 subunit and IFNAR2 subunit.

Epidermal growth factor receptor (EGFR) is cell surface receptor that belongs to the ErbB family of receptors. EGFR binds ligands including epidermal growth factor (EGF) and transforming growth factor-a (TGF-a). Upon ligand binding, EGFR dimerizes and autophosphorylates tyrosine residues in the intracellular C-terminal portion of the receptor, which triggers a signaling cascade that results in expression of genes involved in modulating cell migration, adhesion, and proliferation. As used herein, "EGFRvIII" refers to EGFR variant type III that is produced due to an in-frame deletion of exons 2-7, which also generates a novel glycine residue at the new junction between exons 1 and 8. The deletion corresponds to removal of 267 amino acids of the extracellular domain of EGFR and an inability of EGFRvIII to bind its ligands. Despite the loss of ligand binding capability, EGFRvIII has been found to be phosphorylated and constitutively active, leading to sustained activation of anti-apoptotic and pro-invasive signaling pathways. Further enhancing the oncogenic and tumorigenic potential of cells expressing the EGFR variant, EGFRvIII has impaired internalization and degradation. In some embodiments, chimeric molecules described herein specifically bind to EGFRvIII. In some embodiments, chimeric molecules described herein include an antibody region that specifically binds to EGFRvIII. However, it should be appreciated that in some embodiments a chimeric molecule described herein can include a peptide (e.g., a ligand) that specifically binds to EGFRvIII instead of an antibody region.

As used herein, a "target cell" refers to a cell that expresses a target protein of interest (e.g., EGFRvII1). In some embodiments, the cell has one or more additional characteristics of a tumorigenic or cancer cell. As also used herein, a "targeting molecule" refers to a molecule on the cell surface that identifies the cell as a target for a desired activity. The targeting molecule can be detected (e.g., bound) by a portion of the chimeric activator. In some embodiments, expression and cell surface localization of EGFRvIII is the targeting molecule that is bound by the chimeric activator.

Protein Domains that Bind a Multisubunit Signaling Receptor

In some aspects of the disclosure, the fusion protein comprises a protein domain that binds to one or more subunits of a multisubunit signaling receptor. The protein domain that binds to one or more subunits of a multisubunit signaling receptor may also be referred to as an activity element. As used herein, the terms "multisubunit signaling receptor," "multimeric receptor," and "multimeric target" may be used interchangeably and refer to a receptor on the surface of a cell that is comprised of two or more subunits.

In some embodiments, the multisubunit signaling receptor is a homomultimeric receptor. In other embodiments, the multisubunit signaling receptor is a heteromultimeric receptor. In some embodiments, the protein domain of the fusion protein binds to at least two subunits of the multimeric receptor. In some embodiments, the multisubunit receptor is a metazoan signaling receptor.

As used herein, a "face" of a protein or protein domain refers to a surface of a protein. A protein or protein domain that binds to another molecule, such as a multisubunit receptor, by different faces of the protein domain means different amino acid residues of the protein domain interact with the other molecule. In some embodiments, the protein domain of the fusion protein binds to the multisubunit receptor by different faces of the protein domain. In some embodiments, one face of the protein domain of the fusion protein binds to one subunit of the multisubunit receptor and another face of the protein domain binds to another subunit of the multisubunit receptor.

In some embodiments, the protein domain that binds to the multisubunit signaling receptor is a cytokine or a hormone. In some embodiments, the multisubunit signaling receptor is the Type 1 interferon receptor. In some embodiments, the fusion protein comprises a protein domain that binds to the Type 1 interferon receptor (IFNAR). Preferably, the protein domain that binds to IFNAR activates the IFN signaling pathway and induces anti-proliferative effects. In some embodiments, the polypeptide binds to IFNAR and induces death of the target cell (e.g., cytotoxic effects). The anti-proliferative effects of the fusion protein or the chimeric activator can be evaluated by methods described herein or routine in the art.

As used herein, "IFNAR" or "IFNAR complex" refers to the combination of the IFNAR1 and IFNAR2 subunits that together comprise a functional Type 1 interferon receptor. In some embodiments, a protein domain that binds to the IFNAR complex binds first to the IFNAR1 subunit and then the IFNAR2 subunit. In some embodiments, the protein domain that binds to the IFNAR complex binds first the IFNAR2 subunit and then to the IFNAR1 subunit. It is known in the art that a polypeptide will bind first to a receptor or receptor subunit to which the polypeptide has the highest binding affinity. In some embodiments, the protein domain has a higher binding affinity to IFNAR2 compared to IFNAR1. Without wishing to be bound by any particular theory, the polypeptide portion of chimeric activator binds first to IFNAR2. The polypeptide/IFNAR2 complex can diffuse in two dimensions in the cell membrane until it contacts a IFNAR1 subunit. The IFNAR1/IFNAR2/polypeptide trimeric complex is a signaling complex.

Other examples of multimeric signaling receptors include, without limitation. IL-2 receptor, IL-4 receptor, and LIF receptor. In some embodiments, the protein domain that binds to the multimeric signaling receptor is a cytokine or a hormone.

Any polypeptide or protein domain that binds to IFNAR can be used in the chimeric activators described herein. In preferred embodiments, the protein domain that binds IFNAR is a Type 1 interferon (IFN). In some embodiments, the IFN is an IFN-a selected from IFN-a1, IFN-a2, IFN-a4, IFN-a5, IFN-a6, IFN-a7, IFN-a8, IFN-a10, IFN-a13, IFN-a14, IFN-a16, IFN-a17, or IFN-a21. In some embodiments, the IFN is IFN-a2. In some embodiments, the IFN is an IFN-13 selected from IFN-131 or IFN-133.

In some embodiments, the protein domain that binds to the IFNAR complex is a synthetic IFN. The amino acid sequence of a synthetic IFN may be generated by comparing the amino acid sequence of multiple (e.g., two or more) IFN and identifying a preferred amino acid sequence. In some embodiments, the amino acid sequence of a synthetic IFN may be generated by including one or more amino acid substitutions that stabilize and/or increase the intracellular activity of the chimeric activator. In some embodiments, the protein domain that binds to the IFNAR complex is IFNa2-1 and is provided by SEQ ID NO: 18.

As used herein, the "backbone amino acid sequence" of the IFN refers to any portion of the IFN protein or fragment excluding the portions of the IFN that binds to the IFNAR1 or 1FNAR2 subunits of the Type 1 interferon receptor. In some embodiments, the backbone sequence of the IFN comprises one or more substitution mutations. In some embodiments, one or more substitution mutations are made in the backbone sequence of the IFN such that residue 23 is A, residue 26 is P, residue 44 is D, residue 52 is Q, residue 53 is A, residue 55 is S, residue 83 is E, residue 101 is T, residue 104 is V, residue 105 is G, residue 107 is E, or residue 125 is E.

In some embodiments, the one or more substitution mutations are selected to enhance one or more properties (e.g., folding, expression, and/or intracellular stability) of the polypeptide or of the fusion protein and/or the protein domain. In some embodiments the substitution mutations are selected to enhance the stability of the trimeric complex formed between the IFN (or protein domain of IFN) and the IFNAR1 and IFNAR2 subunits. Increasing the stability of said trimeric complex may result in a trimeric complex with features such as increased resistance to internalization, decreased trafficking to the lysosome, and/or resistance to degradation. Any of the foregoing features may increase the signaling (e.g., strength or duration) through the IFNAR signaling pathway and enhance the anti-proliferative effects of the chimeric activator.

As used herein, a "mutation" refers to a change in a nucleotide sequence relative to a wild-type form of a gene. A change in the nucleotide sequence may or may not lead to a change in the amino acid sequence, the three-dimensional structure of the protein, and/or the activity of the protein, relative to the wild-type form of the protein. In some embodiments a mutation may be a naturally occurring variant of the gene. In some embodiments a mutation results in a single amino acid substitution, two or more amino acid substitutions, one or more deletions, one or more insertions, or any combination of two or more thereof, in the protein sequence of any portion of the fusion proteins or chimeric activators described herein.

In some embodiments, the amino acid sequence of the polypeptide of the chimeric activator is at least 80% (e.g., 85%, 90%, 95%, 98%, 99%) identical to IFN-a2. In some embodiments, the amino acid sequence of a chimeric activator is at least 80% (e.g., 85%, 90%, 95%, 98%, 99%) identical to the sequence of one or more chimeric activators described herein. The "percent identity" of two amino acid sequences is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, wordlength=3 to obtain amino acid sequences homologous to the protein molecules of interest. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used.

In some embodiments, aspects of the present disclosure are based on the recognition that modulating the binding affinity of a protein domain of the fusion protein to each of the receptor subunits of a multimeric (e.g., heterodimeric) receptor (e.g., the IFNAR1 and IFNAR2 subunits of IFNAR) results in enhanced signaling through the receptor (e.g., Type 1 interferon receptor). Such modulation can also result in enhanced specificity of the desired activity of the chimeric activator to the target cell and reduced activity on side effect cells. Aspects of the disclosure relate to protein domains that bind a multimeric target receptor (e.g., IFNAR) and comprise one or more mutations to modulate the binding affinity of the polypeptide to the receptor subunits (e.g., IFNAR1 and IFNAR2 subunits of IFNAR). Binding or interaction between the protein domain of the fusion protein and the subunits of the multisubunit signaling receptor may induce a signaling transduction pathway in the cell that results in a desired activity in the cell (e.g., inhibit or prevent proliferation, induce cytotoxicity, induce or repress gene expression). In some embodiments, binding of the polypeptide portion of the chimeric activator to IFNAR results in a desired effect on the cell expressing IFNAR. In some embodiments, the desired effect is an anti-proliferative effect. The anti-proliferative effect can be measured directly by quantifying cellular proliferation by flow cytometry, cell counting, monitoring cellular metabolism or gene expression, or other methods known in the art. Binding of the polypeptide to IFNAR can be assessed by any method known in the art, including, without limitation, internal reflection fluorescence microscopy, reflectance interference detection, assessing IFNAR subunit conformational change, assessing Jak/Stat signaling pathway activation, assaying production of one or more cytokine induced by IFN or expression of any one or more genes regulated by IFN.

Aspects of the disclosure relate to mutations that effect the binding affinity of a polypeptide or protein domain to a receptor or antigen. As used herein, "binding affinity" refers to the apparent association constant or $K_A$. The $K_A$ is the reciprocal of the dissociation constant ($K_D$). The protein domain of a fusion protein described herein may have a binding affinity ($K_D$) of at least $10^5$, $10^6$, $10^7$, $10^8$, $10^9$, $10^{19}$ M, or lower to one or more subunits of the multimeric signaling receptor. An increased binding affinity corresponds to a decreased $K_D$. Higher affinity binding of protein domain for a first molecule relative to a second molecule can be indicated by a higher $K_A$ (or a smaller numerical value $K_D$) for binding the first molecule than the $K_A$ (or numerical value $K_D$) for binding the second molecule. In some embodiments, mutations in the protein domain may result in altering (increasing or decreasing) the binding affinity of the protein domain to one or more subunits of the multimeric signaling receptor. In some embodiments, the binding affinity of the protein domain to one subunit of the multimeric receptor is substantially the same as the binding affinity of the protein domain to another subunit of the multimeric receptor.

In some embodiments, without the one or more amino acid substitutions, a protein domain binds to a first subunit (e.g., the IFNAR2 subunit) with a higher binding affinity relative to the binding affinity of the protein domain to the a second subunit (e.g., the IFNAR1 subunit). Mutations, such as substitutions, can be made to increase or decrease the binding affinity of the polypeptide to the first subunit (e.g., the IFNAR2 subunit). In some embodiments, the binding affinity of the protein domain to the first subunit (e.g., the IFNAR2 subunit) is reduced by at least 1.5-, 2-, 3-, 4-, 5-, 6-, 7-, 8-, 9, 10-, 20-, 50-, 100-fold or more relative to the protein domain that does not contain the mutation(s). In some embodiments, the binding affinity of the polypeptide to the first subunit (e.g., the IFNAR2 subunit) is increased by at least 1.5-, 2-, 3-, 4-, 5-, 6-, 7-, 8-, 9, 10-, 20-, 50-, 100-fold or more relative to the protein domain that does not contain the mutation(s). Mutations can be made to increase or decrease the binding affinity of the protein domain to the second subunit (e.g., the IFNAR1 subunit). In some embodiments, the binding affinity of the protein domain to the second subunit (e.g., the IFNARI subunit) is increased by at least 2-, 3-, 4-, 5-, 6-, 7-, 8-, 9, 10-, 20-, 50-, 100-fold or more relative to the protein domain that does not contain the mutation(s). In some embodiments, the binding affinity of the polypeptide to the second subunit (e.g., the IFNAR1 subunit) is reduced by at least 2-, 3-, 4-, 5-, 6-, 7-, 8-, 9, 10-, 20-, 50-, 100-fold or more relative to the protein domain that does not contain the mutation(s). In some embodiments, mutations are made to decrease the binding affinity of the polypeptide to the first subunit (e.g., the IFNAR2 subunit) and to increase the binding affinity of the polypeptide to the second subunit (e.g., the IFNAR1 subunit). In some embodiments, the binding affinity of the mutant polypeptide to the first subunit (e.g., the IFNAR2 subunit) is substantially equal to the binding affinity of the mutant polypeptide to the second subunit (e.g., the IFNAR1 subunit). In some embodiments, the binding affinity of the mutant polypeptide to the first subunit (e.g., the IFNAR2 subunit) is within a range of between 10:1 and 1:10 (e.g., between 5:1 and 1:5, between 2:1 and 1:2, or within a range of +/−50%) of the binding affinity of the mutant polypeptide to the second subunit (e.g., the IFNAR1 subunit). FIG. 3 illustrates examples of fusion proteins in which two mutations are introduced into a protein domain (IFNa), with one mutation increasing binding affinity for one subunit, such as IFNAR1, and a second mutation decreasing binding affinity for the other receptor subunit, such as IFNAR2. The binding affinity of the resulting IFNa for each receptor subunit is approximately equal.

In some embodiments, one or more substitution mutations may be made in the amino acid sequence of the protein domain that binds to IFNAR in order to modulate the binding affinity to IFNAR1 or IFNAR2. Substitution mutations can be selected from residues L30, R145, M149, E59, H58, and R150. In some embodiments, the one or more substitution mutations are selected from L30A, R145A, M149A, E59A, H58A, and R150A. In some embodiments, the IFN-a comprises mutations H58A and R150A. In some embodiments, the IFN-a comprises mutations E59A and M149A.

In some embodiments, the binding affinity of the protein domain of the fusion protein to the multimeric receptor is lower than the binding affinity of the antibody variable region element to the cell surface antigen. In some embodiments, the binding affinity of the protein domain of the fusion protein to IFNAR is lower than the binding affinity of the anti-EGFRvIII antibody element to EGFRvIII. In some embodiments, the binding affinity of the protein domain to the multimeric receptor (e.g., IFNAR) is at least 2-, 3-, 4-, 5-, 6-, 7-, 8-, 9, 10-, 20-, 50-, 100-fold or more lower than the binding affinity of the antibody variable region element to the cell surface antigen (e.g., anti-EGFRvIII antibody element to EGFRvIII). In some embodiments, the binding affinity of the protein domain to IFNAR1 subunit, IFNAR2 subunit or both IFNAR1 and IFNAR2 subunits may be modulated (increased or decreased) to reduce undesired activity on side effect cells. In some embodiments, modulating the binding affinity of the polypeptide results in enhanced specificity of the activity of a chimeric activator to a target cell (e.g., a cell expressing EGFRvIII).

Binding affinity (or binding specificity) can be determined by a variety of methods including equilibrium dialysis, equilibrium binding, gel filtration, ELISA, surface plasmon resonance, or spectroscopy (e.g., using a fluorescence assay).

Antibody Variable Region Elements that Bind Cell Surface Antigens

Aspects of the disclosure provide fusion proteins comprising an antibody variable region element that binds to a cell surface antigen. The antibody variable region element may also be referred to as a targeting element. As used herein, a "cell surface antigen" refers to a molecule that is present on the surface of a cell and may identify the cell as a target cell. Any protein or fragment thereof that is present on the surface of the cell may be used as a cell surface antigen and bound by an antibody variable region element. In some embodiments, the cell surface antigen is a protein that indicates the cell is a cancer cell (i.e., is a cancer cell marker). In some embodiments, the cell surface antigen is EGFRvIII. In other embodiments, the cell surface antigen may be the tumor specific glycolipid GD2 or the B cell marker CD20, or any other cell surface molecule characteristic of a tumor cell.

The term antibody variable region element encompasses any antibody or fragment thereof, such as a full length immunoglobulin molecule, or an antigen-binding fragment thereof (such as Fab, Fab', F(ab')2, Fv), single chain (scFv), mutant thereof, fusion protein comprising an antibody portion, humanized antibody, chimeric antibody, diabody, linear antibody, single chain antibody, multispecific antibody (e.g., bispecific antibodies) and/or any other modified configuration of the immunoglobulin molecule that comprises an antigen recognition site of the required specificity. An antibody is capable of binding to a cell surface antigen, such as a cell surface receptor, through at least one antigen recognition site located at the variable region of the immunoglobulin molecule. In some embodiments, the antibody of the fusion proteins described herein is a scFv that binds to EGFRvIII (e.g., MR1-1). In some embodiments, the antibody of the fusion protein described herein is a full length immunoglobulin or fragment thereof that binds to EGFRvIII. In some embodiments, the antibody binding to EGFRvIII targets the chimeric activator to the desired target cell. In some embodiments, the target cell is a cancer cell.

Also within the scope of the present disclosure are antibodies that are derived from a parent antibody that is capable of binding to a cell surface antigen (e.g., EGFRvIII). The parent antibodies may specifically bind a desired epitope of EGFRvIII, for example, an epitope that is present on EGFRvIII. In some embodiments, the epitope to which the antibody binds is present on EGFRvIII but absent on full length EGFR. In some embodiments, the antibody is the MR1-1 scFv antibody. In some embodiments, the epitope comprises a novel glycine residue that is formed by the deletion of exons 2-7 in producing EGFRvIII.

One or more parent antibodies that may be used for constructing fusion proteins described herein can be naturally occurring antibodies (e.g., an antibody derived from a human, mouse, rat, rabbit, horse, or sheep), genetically engineered antibodies (e.g., humanized antibodies, chimeric antibodies), or antibodies derived from a natural or synthetic antibody library. In some embodiments, the antibody is a full length monoclonal antibody. In some embodiments, the antibody is a single chain antibody (svFc). In some embodiments, the svFc is MR1-1.

In some examples, the antibody can be an affinity matured antibody, which refers to an antibody having one or more modifications in one or more CDRs or framework regions (FRs) as compared to the unmodified parent antibody, leading to an improvement in the affinity of the antibody for the target antigen. Preferred affinity matured antibodies may have nanomolar or even picomolar affinities for the target antigen. Affinity maturation of an antibody can be performed by various methods known in the art, including by variable domain shuffling (see, e.g., Marks et al. 1992, Bio/Technology 10:779-783), random mutagenesis of CDR and/or FR residues (see, e.g., Barbas et al., 1994, Proc Nat. Acad. Sci, USA 91:3809-3813; Schier et al., 1995, Gene 169:147-155; Yelton et al., 1995, J. Immunol. 155:1994-2004; Jackson et al., 1995, J. Immunol. 154(7):3310-9; and Hawkins et al, 1992, J. Mol. Biol. 226:889-896). The parent antibodies can be of any class, such as IgD, IgE, IgG, IgA, or IgM, or a sub-class thereof, or a single chain antibody, such as a scFv.

In some embodiments, the antibody variable region element of the fusion protein specifically or selectively binds to the cell surface antigen. In some embodiments, the anti-EGFRvIII antibody of the fusion protein specifically or selectively binds to EGFRvIII. An antibody with "specific binding" reacts or associates more frequently, more rapidly, with greater duration and/or with greater affinity with the cell surface antigen than it does with a different molecule. The antibody variable region element may "specifically bind" to the cell surface antigen with greater affinity, avidity, more readily, and/or with greater duration than it binds to other substances. "Specific binding" does not necessarily require (although it can include) exclusive binding. Generally, but not necessarily, reference to binding means preferential binding. In some examples, an antibody that "specifically binds" to a target antigen or an epitope thereof may not bind to other antigens or other epitopes in the same antigen. In some embodiments, the fusion proteins described herein specifically bind to EGFRvIII. In some embodiments, the fusion proteins do not bind to full length EGFR.

Other antibodies that specifically bind to EGFRvIII are compatible for use in the fusion proteins described herein and are known in the art, for example in Modjtahedi et al. 2003 Int. J. of Cancer 105(2) and PCT Application No. WO 2001/062931.

In some embodiments, a fusion protein as described herein has a binding affinity for EGFRvIII or epitopes thereof such that the fusion protein is targeted to a cell with EGFRvIII present on the cell surface. In some embodiments, the binding affinity of the fusion protein to EGFRvIII is higher than the binding affinity of the fusion protein to full length EGFR. In some embodiments, the binding affinity of the fusion protein to EGFRvIII is at least 1.5, 2, 3, 4, 5, 10, 15, 20, 37.5, 50, 70, 80, 91, 100, 500, 1000, 10,000 or $10^5$ fold higher than the binding affinity of the chimeric activator to full length EGFR.

In other embodiments, the anti EGFRvIII antibody is the monoclonal antibody 806 or a fragment or variant therefor (see, for example, Johns et al. J. Biol. Chem. (2004) 279(29): 30375-84).

These may be linked by a suitable linker as illustrated herein. As is well known in the art, within the antigen-binding portion of an antibody there are complementarity determining regions (CDRs), which directly interact with the epitope of the antigen, and framework regions (FRs), which maintain the tertiary structure of the antigen-binding portion (see, in general, Clark, 1986; Roitt, 1991). In both the heavy chain and the light chain of IgG immunoglobulins, there are four framework regions (FR1-FR4) separated respectively by three complementarity determining regions (CDR1-CDR3). The CDRs, and in particular the CDR3 regions, and more particularly the heavy chain CDR3, are largely responsible for antibody specificity.

In some examples, the anti-EGFRvIII antibody is a functional variant of MR1-1, which comprises up to 5 (e.g., 4, 3, 2, or 1) amino acid residue variations in one or more of the CDR regions of MR1-1 and binds EGFRvIII with substantially similar affinity as MR1-1 (e.g., having a KD value in the same order). In one example, the amino acid residue variations are conservative amino acid residue substitutions. As used herein, a "conservative amino acid substitution" refers to an amino acid substitution that does not alter the relative charge or size characteristics of the protein in which the amino acid substitution is made.

Variants can be prepared according to methods for altering polypeptide sequence known to one of ordinary skill in the art such as are found in references which compile such methods, e.g., Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

In some embodiments, the anti-EGFRvIII comprises heavy chain CDRs that are at least 80% (e.g., 85%, 90%, 95%, 96%, 97%, 98%, or 99%) identical to the corresponding heavy chain CDRs of MR1-1 and/or light chain CDRs that are at least 80% (e.g., 85%, 90%, 95%, 96%, 97%, 98%, or 99%) identical to the corresponding light chain CDRs of MR1-1. In some embodiments, the anti-EGFRvIII antibody comprises a heavy chain variable region that is at least 80% (e.g., 85%, 90%, 95%, or 98%) identical to the heavy chain variable region of MR1-1 and/or light chain variable region that is at least 80% (e.g., 85%, 90%, 95%, 96%, 97%, 98%, or 99%) identical to the light chain variable region of MR1-1.

In one example, the anti-EGFRvIII of the chimeric activator comprises the same heavy chain variable region (SEQ ID NO:15) and light chain variable region (SEQ ID NO:16) as MR1-1.

In another example, the heavy chain variable region and light chain variable region of MR1-1 can be combined with the constant regions of an immunoglobulin to produce a full length immunoglobulin or fragment thereof that specifically binds to EGFRvIII. In some embodiments, the heavy chain CDR sequences and light chain CDR sequences of MR1-1 are combined with the variable regions and constant regions of an immunoglobulin to produce a full length immunoglobulin or fragment thereof that specifically binds to EGFRvIII. The constant regions can be from any antibody isotype including IgG, IgA, IgM, IgE, IgD.

Also within the scope of the disclosure are antibody variable region elements that bind any other cell surface antigens. In other embodiments, the cell surface antigen may be the tumor specific glycolipid GD2 or the B cell marker CD20, or any other tumor or disease-associated cell surface antigen. In some embodiments, the cell surface antigen is GD2 and the antibody variable region element is the 14.18 antibody or fragment or variant thereof (Ch14.18; see, for example Barker et al. Cancer Res. (1991) 51(1): 144-149). In some embodiments, the cell surface antigen is CD20 and the antibody variable region element is rituximab, or a fragment or variant thereof.

Linker

As used herein a "linker" refers to a polypeptide or a nucleic acid that functions to attach two portions of a chimeric activator. The linker of the fusion proteins described herein connects the protein domain and the antibody variable region element. In some embodiments, the linker connects the C-terminal end of the antibody variable region element to the N-terminal end of the protein domain. In other embodiments, the linker connects the N-terminal end of the antibody variable region element to the C-terminal end of the protein domain.

A linker can comprise, for example 10 to 200 or more amino acids. In some embodiments, the linker comprises 15-100, or 30-50 amino acids. In other embodiments, the linker comprises, for example, 10 to 1000 nucleotides or more. In some embodiments, the linker comprises 100-900, 200-800, 300-700, 500-1000, or 700-1000 nucleotides.

The amino acid sequence and/or length of the linker can be optimized for one or more desired properties (e.g., separation of the polypeptide and the antibody portions, prevention of self-binding of the portions of the chimeric activator). In some embodiments, the length of the linker allows for binding of the protein domain to the multisubunit signaling receptor and binding of the antibody variable region element to the cell surface antigen on the same cell. In some embodiments, the length of the linker allows for binding of the protein domain to the multisubunit signaling receptor and binding of the antibody variable region element to the cell surface antigen at the same time.

In some embodiments, the linker has a net charge. In some embodiments, the linker has a negative net charge. In such embodiments, the amino acid residues of the linker are selected from the group consisting of glycine, serine, glutamate, and aspartate. In some embodiments, the linker comprises repeats (e.g., 1, 2, 3, 4, 5, 6, 7, 8, 9, 10, or 20 more repeats) of GGGSE (SEQ ID NO:11), GSESG (SEQ ID NO:12), or GSEGS (SEQ ID NO:13). In some embodiments the linker comprises the sequence or SEQ ID NO:14: GEGGSGEGSSGEGSSSEGGGSEGGGSEGGGSEGG.

In some embodiments, the linker consists of a sequence with uncharged amino acids that promote flexibility and mitigate against formation of a folded structure, with glutamic acid or aspartic acid present at regularly spaced intervals. In some embodiments, the uncharged amino acids are selected from glycine, serine, alanine, proline and threonine. In some embodiments, the uncharged amino acids are present in a non-repetitive pattern.

Without wishing to be bound by any theory, the interspersing uncharged amino acids in a non-repetitive pattern provides that the nucleic acid encoding an expression construct for such a linker is also non-repetitive and therefore may be less likely to undergo internal recombination events that lead to deletion. FIG. 2 illustrates examples of linkers in which a charged amino acid is present with a regular spacing and the uncharged amino acids are present in a non-repeating pattern. In some embodiments, the linker comprises negatively charged amino acids with regular spacing interspersed with non-charged amino acids, for example in non-regular spacing.

In other embodiments, the linker has a positive net charge. In such embodiments, the amino acid residues of the linker are selected from the group consisting of lysine, histidine, and arginine.

Anti-EGFR/Anti-Type 1 IFN Receptor Fusion Proteins

In some embodiments, the fusion proteins described herein may comprise a protein domain that binds to IFNAR, an antibody that binds to EGFRvIII, and a linker that connects the protein domain and the antibody. In some embodiments, the polypeptide comprises an interferon (IFN). In some embodiments, the antibody that binds EGFRvIII comprises a single chain antibody (scFv). In some embodiments, the scFv is MR1-1. In some embodiments, the C-terminus of the heavy chain variable region of MR1-1 (SEQ ID NO:15) or the C-terminus of the light chain variable region of MR1-1 (SEQ ID NO: 16) is fused to the linker. In some embodiments, the linker is connected to N-terminus of the heavy chain variable region of MR1-1 (SEQ ID NO:15) or the N-terminus of the light chain variable region of MR1-1 (SEQ ID NO: 16). In some embodiments, the antibody that binds to EGFRvIII is the antibody 806. In some embodiments, the C-terminus of the antibody 806 is fused to the linker.

In some embodiments, the linker is connected to the N-terminus of the protein domain. Alternatively, in other embodiments, the C-terminus of the protein domain is fused to the linker. Non-limiting examples of linker sequences compatible for use in generating chimeric activators are described herein.

The heavy chain variable region of a svFc can be connected to the light chain variable region of a svFc with a peptide linker, such as a peptide that is rich in Gly and/or Ser residues, which are known in the art. The peptide linker can comprise, for example, 1, 2, 3, 4, 5, 6, 7, 8, 9, 10 or more amino acid residues (e.g., up to 50 amino acid residues). In some embodiments, the peptide linker can comprise 2-50, 5-25, or 5-20 amino acids. In some embodiments, the peptide linker is a peptide rich in glycine residues. In some embodiments, the peptide linker is rich in both G and S. Amino acid sequences for examples of fusion proteins are provided below.

MR1-1 IFNa 2-1b wt (SEQ ID NO: 1) consists of the heavy chain variable sequence of MR1-1, a glycine-serine linker (underlined), light chain variable sequence of MR1-1, charged linker (underlined), and IFNa2-1b (bold)

```
                                                              (SEQ ID NO: 1)
EVQLVESGGGLVQPGGSLRLSCKVSGFTFS SYGMSWVRQAPGKGLEWVAS I STGGYNTYY AD

SVKGRFT I SRDNSKNTLYLQMNSLRAEDTAVYYCARGYS

PYSYAMDYWGQGTTVTVSGGGGG S GGGGSGGGGS DI QMTQ S PS

SLSASVGDRVT I T CRAS T DI DNDMNWYQQKPGQAPKLL I YEG NS LQSGVP SRFS

S SGSGTDFTLT I SSLQPEDFATYY CLQSWNVPLTFGQGTKLE IKGEGGSG EGS

SGEGS S SEGGGSEGGGSEGGGS

EGGSCDLPQTHSLGSRRTLMLLAQMRRISPFSCLKDR

HDFGFPQEEFDGNQFQKAQAISVLHEMIQQIFNLFSTKDSSAAWDETLLEK

FYTELYQQLND

LEACVTQEVGVEETPLMNEDSILAVKKYFQRITLYLTEKKYSPCAWEVVRAEIMRSFSLST

NLQERLRRKEHHHHHH
```

MR1-1 IFNa 2-1b L30A (SEQ ID NO: 2) consists of the heavy chain variable sequence of MR1-1, a glycine-serine linker (underlined), light chain variable sequence of MR1-1, charged linker (underlined), and IFNa2-b with L30A substitution (bold)

```
                                                              (SEQ ID NO: 2)
EVQLVESGGGLVQPGGSLRLSCKVSGFIFSSYGMSWVRQAPGKGLEWVAS I S TGGYNTYYAD

SVKGRFTISRDNSKNTLYLQMNSLRAEDTAVYYCARGYSPYSYAMDYWGQGTTVTVSGGGG

GSGGGGSGGGGSDIQMTQSPSSLSASVGDRVTITCRASTDIDNDMNWYQQKPGQAPKLLIYEG

NSLQSGVPSRFSSSGSGTDFTLTISSLQPEDFATYYCLQSWNVPLTFGQGTKLEIKGEGGSG

EGSSGEGSS

SEGGGSEGGGSEGGGSEGGSCDLPQTHSLGSRRTLMLLAQMRRISPFSCAKDR

HDFGFPQEEFDGNQFQKAQAISVLHEMIQQIFNLFSTKDSSAAWDETLLEKFYTELYQQL

ND

LEACVTQEVGVEETPLMNEDSILAVKKYFQRITLYLTEKKYSPCAWEVVRAEIMRSFSLST

NLQERLRRKEHHHHHH
```

MR1-1 IFNa 2-1b R145A (SEQ ID NO: 3) consists of the heavy chain variable sequence of MR1-1, a glycine-serine linker (underlined), light chain variable sequence of MR1-1, charged linker (underlined), and IFNa2-b with R145A substitution (bold)

(Seq ID NO: 3)
EVQLVESGGGLVQPGGSLRLSCKVSGFTFSSYGMSWVRQAPGKGLEWVASISTGGYNTY

YAD

SVKGRFTISRDNSKNTLYLQMNSLRAEDTAVYYCARGYSPYSYAMDYWGQGTTVTVSGGGG

GSGGGGSGGGGSDIQMTQSPSSLSASVGDRVTITCRASTDIDNDMNWYQQKPGQAPKLLIYEG

NSLQSGVPSRFSSSGSGTDFTLTISSLQPEDFATYYCLQSWNVPLTFGQGTKLEIKGEGGSG

EGSSGEGSSSEGGGSEGGGSEGGGSEGGSCDLPQTHSLGSRRTLMLLAQMRRISPFSCLKD

R

HDFGFPQEEFDGNQFQKAQAISVLHEMIQQIFNLFSTKDSSAAWDETLLEKFYTELYQQL

ND

LEACVTQEVGVEETPLMNEDSILAVKKYFQRITLYLTEKKYSPCAWEVVAAEIMRSFSLST

NLQERLRRKEHHHHHH

MR1-1 IFNa 2-1b E59A M149A (SEQ ID NO: 4) consists of the heavy chain variable sequence of MR1-1, a glycine-serine linker (underlined), light chain variable sequence of MR1-1, charged linker (underlined), and IFNa2-b with E59A M149 substitutions (bold)

(SEQ ID NO: 4)
EVQLVESGGGLVQPGGSLRLSCKVSGFTFSSYGMSWVRQAPGKGLEWVASISTGGYNTYYAD

SVKGRFTISRDNSKNTLYLQMNSLRAEDTAVYYCARGYSPYSYAMDYWGQGTTVTVSGGGG

GSGGGGSGGGGSDIQMTQSPSSLSASVGDRVTITCRASTDIDNDMNWYQQKPGQAPKLLIYEG

NSLQSGVPSRFSSSGSGTDFTLTISSLQPEDFATYYCLQSWNVPLTFGQGTKLEIKGEGGSG

EGSSGEGSSSEGGGSEGGGSEGGGSEGGSCDLPQTHSLGSRRTLMLLAQMRRISPFSCLKD

R

HDFGFPQEEFDGNQFQKAQAISVLHAMIQQIFNLFSTKDSSAAWDETLLEKFYTELYQQL

ND

LEACVTQEVGVEETPLMNEDSILAVKKYFQRITLYLTEKKYSPCAWEVVRAEIARSFSLST

NLQERLRRKEHHHHHH

MR1-1 IFNa 2-1b H58A R150A (SEQ ID NO: 5) consists of the heavy chain variable sequence of MR1-1, a glycine-serine linker (underlined), light chain variable sequence of MR1-1, charged linker (underlined), and IFNa2-b with H58A R150A substitutions (bold)

(SEQ ID NO: 5)
EVQLVESGGGLVQPGGSLRLSCKVSGFTFSSYGMSWVRQAPGKGLEWVASISTGGYNTYYAD

SVKGRFTISRDNSKNTLYLQMNSLRAEDTAVYYCARGYSPYSYAMDYWGQGTTVTVSGGGG S

GGGGS GGGGS DIQMTQ S PS SLSASVGDRVTITCRAS T DI DNDMNWYQQKPGQAPKLLI YEG NS LQ S

GVP SRFS S S GS GT DFILT I S SLQPEDFATYYCLQSWNVPLTFGQGTKLEIKGEGGS G

EGS SGEGS S

SEGGGSEGGGSEGGGSEGGSCDLPQTHSLGSRRTLMLLAQMRRISPFSCLKDR

-continued

HDFGFPQEEFDGNQFQKAQAISVLAEMIQQIFNLFSTKDSSAAWDETLLEKFYTELYQQLN

D

LEACVTQEVGVEETPLMNEDSILAVKKYFQRITLYLTEKKYSPCAWEVVRAEIMASFSLST

NLQERLRRKEHHHHHH

In the preceding sequences, the protein domain (IFN element) is based on the following sequence, which is particularly useful as a domain with Type 1 IFN activity:

SEQ ID NO: 18
CDLPQTHSLGSRRILMLLAQMRRI S PFSCLKDRHDFGFPQEEFDGNQFQKAQAI

SVLHEMIQ

Q I FNLFS TKDS SAAWDEILLEKFYIELYQQLNDLEACVIQEVGVEETPLMNEDS I

LAVKKYF

QRI TLYLTEKKYS PCAWEVVRAE IMRSFSLS TNLQERLRRKE.

This polypeptide sequence may be fused to scFvs or other targeting moieties such as whole antibodies, Fab fragments, minibodies, diabodies, camelid-based single-domain V regions, or non-antibody-based binding units such as short peptide aptamers or naturally occurring ligands. Targeting elements (antibody variable region elements) that bind to tumor cells, tumor-associated cells such as stroma or endothelia, or virus-infected cells may be useful as in fusion proteins with the protein domain provided by SEQ ID NO: 18.

Preparation of Fusion Proteins

Methods known in the art, e.g., using standard recombinant technology, can be used for preparing the chimeric activators based on the present disclosure.

Antibody variable region elements can be obtained via a routine technology from suitable sources, e.g., PCR amplification from a suitable source. Similarly, protein domains may be obtained from any suitable source. In one example, the DNA encoding an antibody variable region element that binds to a cell surface antigen and/or a protein domain that binds to a multisubunit signaling receptor can be readily isolated and sequenced using conventional procedures (e.g., by using oligonucleotide probes that are capable of binding specifically to genes encoding the antibody and/or protein domain.

Nucleotide sequences encoding one or more of portion of the fusion proteins as described herein can be cloned into one or more expression vector, each nucleotide sequence being operably linked to a suitable promoter. Alternatively, the nucleotides sequences can be operably linked with a single promoter, such that each of the sequences is expressed from the same promoter as a single protein. In some embodiments, the antibody variable region element is a full length immunoglobulin, or fragment or derivative thereof, comprising two chains. In such examples, the two chains of the antibody portion of the fusion protein may be expressed separately (as two polypeptides) and can be controlled by a common promoter. In other examples, the expression of each of the two chains of the fusion protein is under the control of a distinct promoter. In some embodiments, the nucleotide sequences encoding the two chains of the fusion protein are cloned into two vectors, which can be introduced into the same or different cells. When the two chains are expressed in different cells, each of them can be isolated from the host cells expressing such and the two isolated chains can be mixed and incubated under suitable conditions allowing for the formation of the chimeric activator. Generally, a nucleic acid sequence encoding one or all chains of a chimeric activator can be cloned into a suitable expression vector in operable linkage with a suitable promoter using methods known in the art. The selection of expression vectors/promoter would depend on the type of host cells for use in producing the antibodies.

A variety of promoters can be used for expression of the fusion proteins (e.g., chimeric activators) described herein. In some embodiments, the fusion proteins are expressed in *Pichia pastoris* and the promoter is the U6 promoter or the AOX promoter (see, for example, Daly et al. *J. Mol. Recognoit.* (2005) 18(2) p 119-38. Other examples of promoters include, without limitation, including, but not limited to, cytomegalovirus (CMV) intermediate early promoter, a viral LTR such as the Rous sarcoma virus LTR, HIV-LTR, HTLV-1 LTR, the simian virus 40 (SV40) early promoter, *E. coli* lac UV5 promoter, and the herpes simplex tk virus promoter.

Regulatable promoters can also be used, such as regulatable promoters that include a repressor with the operon can be used. In one embodiment, the lac repressor from *E. coli* can function as a transcriptional modulator to regulate transcription from lac operator-bearing mammalian cell promoters [M. Brown et al., Cell, 49:603-612 (1987)]; Gossen and Bujard (1992); [M. Gossen et al., Natl. Acad. Sci. USA, 89:5547-5551 (1992)] combined the tetracycline repressor (tetR) with the transcription activator (VP 16) to create a tetR-mammalian cell transcription activator fusion protein, tTa (tetR-VP 16), with the tet0-bearing minimal promoter derived from the human cytomegalovirus (hCMV) major immediate-early promoter to create a tetR-tet operator system to control gene expression in mammalian cells. In one embodiment, a tetracycline inducible switch is used. The tetracycline repressor (tetR) alone, rather than the tetR-mammalian cell transcription factor fusion derivatives can function as potent trans-modulator to regulate gene expression in mammalian cells when the tetracycline operator is properly positioned downstream for the TATA element of the CMVIE promoter (Yao et al., Human Gene Therapy). One particular advantage of this tetracycline inducible switch is that it does not require the use of a tetracycline repressor-mammalian cells transactivator or repressor fusion protein, which in some instances can be toxic to cells (Gossen et al., Natl. Acad. Sci. USA, 89:5547-5551 (1992); Shockett et al., Proc. Natl. Acad. Sci. USA, 92:6522-6526 (1995)), to achieve its regulatable effects.

Additionally, the vector can contain, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; internal ribosome binding sites (IRESes), versatile multiple cloning sites; and T7 and SP6 RNA promoters for in vitro transcription of RNA. Suitable vectors and methods for producing vectors containing transgenes are well known and available in the art.

Examples of polyadenylation signals useful to practice the methods described herein include, but are not limited to, human collagen I polyadenylation signal, human collagen II polyadenylation signal, and SV40 polyadenylation signal.

One or more vectors (e.g., expression vectors) comprising nucleic acids encoding any of the fusion proteins may be introduced into suitable host cells for producing the chimeric activator. The host cells can be cultured under suitable conditions for expression of the fusion protein or any polypeptide chain thereof Such fusion proteins or polypeptide chains thereof can be recovered by the cultured cells (e.g., from the cells or the culture supernatant) via a conventional method, e.g., affinity purification. If necessary, polypeptide chains of the fusion protein can be incubated under suitable conditions for a suitable period of time allowing for production of the chimeric activator.

Suitable host cells for use in preparing the fusion proteins described herein can be any host cells known in the art that can be used for protein production, including, but not limited to, bacterial cells, yeast cells, fungal cells, insect cells, plant cells, or mammalian cells.

The fusion proteins described herein can be produced in bacterial cells, e.g., *E. coli* cells. Alternatively, the chimeric activators can be produced in eukaryotic cells. In one embodiment, the antibodies are expressed in a yeast cell such as *Pichia pastoris* (see, e.g., Powers et al., 2001, J. Immunol. Methods. 251:123-35), *Hanseula*, or *Saccharomyces*. In another embodiment, the chimeric activators can be produced in mammalian cells. Mammalian host cells for expressing the molecules include, but are not limited to, 293 cells (see, e.g., ATCC CRL-1573, American Type Culture Collection®, and Expi293FTM cells, Life Technologies™), Chinese Hamster Ovary (CHO cells) (including dhfr– CHO cells, described in Urlaub and Chasin, 1980, Proc. Natl. Acad. Sci. USA 77:4216-4220, used with a DHFR selectable marker, e.g., as described in Kaufman and Sharp, 1982, Mol. Biol. 159:601 621), lymphocytic cell lines, e.g., NSO myeloma cells and SP2 cells, COS cells, and a cell from a transgenic animal, e.g., a transgenic mammal. For example, the cell is a mammary epithelial cell.

In some embodiments, methods for preparing a chimeric activator described herein involve a recombinant expression vector that encodes both the heavy chain and the light chain of an anti-EGFRvIII antibody, wherein the heavy chain and the light chain can be fused (e.g., at the C-terminus) to a linker that is fused to a polypeptide that binds to IFNAR, as also described herein. In some embodiments, the methods for preparing a chimeric activator described herein involve a recombinant expression vector that encodes a single chain antibody (scFv) comprising the heavy chain variable region and the light chain variable region of MR1-1, in which case the heavy chain variable region or the light chain variable region is fused to a to a linker that is fused to a polypeptide that binds to IFNAR, as also described herein. The recombinant expression vector can be introduced into a suitable host cell (e.g., a *P. pastoris* cell) by a conventional method. Positive host cells that express the fusion proteins can be selected and cultured under suitable conditions allowing for the expression of the one or more chains that form the chimeric activator, which can be recovered from the cells or from the culture medium, as described in the Examples.

In other embodiments, the components of the fusion proteins are expressed and/or produced independently and subsequently combined. In some embodiments, the protein domain and the antibody variable region element are expressed each comprising a tag that allows covalent attachment of the components with a linker. Examples of such tags include a SNAP tag or a CLIP tag (see, e.g., Keppler et al. Nat. Biotech. (2002) 21: 86-9).

Standard molecular biology techniques are used to prepare the recombinant expression vector, transfect the host cells, select for transformants, culture the host cells and recovery of the fusion proteins from the culture medium. For example, the fusion proteins can be isolated by affinity chromatography with a Protein A or Protein G coupled matrix.

Pharmaceutical Compositions

The fusion proteins (the encoding isolated nucleic acid, vectors comprising such, or host cells comprising the vectors) as described herein can be mixed with a pharmaceutically acceptable carrier (excipient) to form a pharmaceutical composition for use in treating a target disease. A "pharmaceutically acceptable carrier" or "pharmaceutically acceptable excipient" refer to a carrier that must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover.

The pharmaceutical compositions to be used in the present methods can comprise pharmaceutically acceptable carriers, excipients, or stabilizers in the form of lyophilized formulations or aqueous solutions. (Remington: The Science and Practice of Pharmacy 20th Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

In some examples, the pharmaceutical composition described herein comprises liposomes containing the fusion protein (or the encoding isolated nucleic acid) which can be prepared by methods known in the art, such as described in Epstein, et al., Proc. Natl. Acad. Sci. USA 82:3688 (1985); Hwang, et al., Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

In other examples, the pharmaceutical composition described herein can be formulated in sustained-release format. Suitable examples of sustained-release preparations include semipermeable matrices of solid hydrophobic polymers containing the fusion protein, which matrices are in the form of shaped articles, e.g., films, or microcapsules. Examples of sustained-release matrices include polyesters, hydrogels (for example, poly(2-hydroxyethyl-methacrylate), or poly(v nylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The pharmaceutical compositions to be used for in vivo administration must be sterile. This is readily accomplished by, for example, filtration through sterile filtration membranes. Therapeutic compositions are generally placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient can be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present disclosure, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present disclosure. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g., Tween™ 20, 40, 60, 80 or 85) and other sorbitans (e.g., Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid'™, Liposyn$^{lm}$, Infonutrol'™, Lipofundin$^{im}$ and Lipiphysan'™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 .im, particularly 0.1 and 0.5 .im, and have a pH in the range of 5.5 to 8.0.

The emulsion compositions can be those prepared by mixing a chimeric activator with Intralipid™ or the components thereof (soybean oil, egg phospholipids, glycerol and water). Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect.

Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Methods of Treatment

In some embodiments, the fusion proteins, the encoding isolated nucleic acid, vectors comprising such, or host cells comprising the vectors, described herein are useful for treating cancer associated with expression of a target molecule (e.g., EGFRvIII, e.g., characterized by constitutive EGFR signaling, unregulated cellular growth and proliferation, survival, invasive capacity, and/or angiogenesis).

To practice the method disclosed herein, an effective amount of a pharmaceutical composition described herein can be administered to an individual (e.g., a human) in need of the treatment via a suitable route, such as intravenous administration, e.g., by intramuscular, intraperitoneal, intracerebrospinal, subcutaneous, intra-articular, intrasynovial, intrathecal, oral, inhalation or topical routes. The individual to be treated by the methods described herein can be a mammal, for example a human. Mammals include, but are not limited to, farm animals, sport animals, pets, primates, horses, dogs, cats, mice and rats. A human who needs the treatment may be a human patient having, at risk for, or suspected of having a cancer, such as a glioblastoma, a squamous cell carcinoma, a solid tumor, or other cancer or condition associated with a target molecule of interest. A subject having a cancer can be identified by routine medical examination, e.g., laboratory tests, organ functional tests, CT scans, or ultrasounds. A subject suspected of having a cancer might show one or more symptoms of the disease/disorder. A subject at risk for the disease/disorder can be a subject having one or more of the risk factors for that cancer.

In some embodiments, the method for treating the individual with cancer comprises detecting whether the cancer expresses EGFRvIII. If expression of EGFRvIII is detected, the individual may be administered an effective amount of the fusion protein described herein.

Detection of whether a cancer expresses EGFRvIII may be performed by any method known in the art or described herein. For example, a sample can be obtained from the individual and the expression of EGFRvIII can be detected using methods including, without limitation immunofluorescence, Western blotting, fluorescence in situ hybridization using a probe the binds to the EGFRvIII RNA, PCR amplification of the EGFR gene using oligonucleotide that flank exons 2 and 7, sequencing of the EGFR genomic locus, or evaluating activity of EGFRvIII (e.g., constitutive signaling).

Cancer is a disease characterized by uncontrolled or aberrantly controlled cell proliferation and other malignant cellular properties (for example resulting from constitutive EGFR signaling). As used herein, the term cancer includes, but is not limited to, the following types of cancer: breast cancer; biliary tract cancer; bladder cancer; brain cancer including glioblastomas and medulloblastomas; cervical cancer; choriocarcinoma; colon cancer; endometrial cancer; esophageal cancer; gastric cancer; hematological neoplasms including acute lymphocytic and myelogenous leukemia; T-cell acute lymphoblastic leukemia/lymphoma; hairy cell leukemia; chronic myelogenous leukemia, multiple myeloma; AIDS-associated leukemias and adult T-cell leukemia/lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Merkel cell carcinoma, Kaposi's sarcoma, basal cell carcinoma, and squamous cell cancer; testicular cancer including germinal tumors such as seminoma, non-seminoma (tcratomas, choriocarcinomas), stromal tumors, and germ cell tumors; thyroid cancer including thyroid adenocarcinoma and medullar carcinoma; and renal cancer including adenocarcinoma and Wilms tumor.

In certain embodiments, cancer is a colon carcinoma, a pancreatic cancer, a breast cancer, an ovarian cancer, a prostate cancer, a squamous cell carcinoma, a cervical cancer, a lung carcinoma, a small cell lung carcinoma, a bladder carcinoma, a squamous cell carcinoma, a basal cell carcinoma, an adenocarcinoma, a sweat gland carcinoma, a sebaceous gland carcinoma, a papillary carcinoma, a papillary adenocarcinoma, a cystadenocarcinoma, a medullary carcinoma, a bronchogenic carcinoma, a renal cell carcinoma, a hepatocellular carcinoma, a bile duct carcinoma, a choriocarcinoma, a seminoma, a embryonal carcinoma, a Wilms' tumor, or a testicular tumor. In some embodiments, cancer is a glioblastoma. In some embodiments, cancer is a squamous cell carcinoma. Other cancers, for example carcinomas, will be known to one of ordinary skill in the art.

"An effective amount" as used herein refers to the amount of the fusion protein required to confer therapeutic effect on the subject, either alone or in combination with one or more other active agents. In some embodiments, the therapeutic effect is reduced cellular proliferation or cell viability of cells expressing EGFRvIII. Determination of whether an amount of the chimeric activator achieved the therapeutic effect would be evident to one of skill in the art. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. For administration of any of the fusion proteins described herein, an individual may be administered between 5 mcg-3 mg, 25 mcg-625 mcg, or approximately 125 mcg of any of the fusion proteins described herein per week. For repeated administrations over several days or longer, depending on the condition, the treatment is sustained until a desired suppression of symptoms occurs or until sufficient therapeutic levels are achieved to alleviate a target disease or disorder, or a symptom thereof. In some embodiments, dosing frequency is once a week, twice a week, three times per week, four times per week, five times per week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the antibody used) can vary over time.

Typically a clinician will administer a fusion protein, until a dosage is reached that achieves the desired result. In some embodiments, the desired result is a reduction of cellular proliferation, cell viability, invasive capability, angiogenesis, or tumorigencity of a cell that expresses EGFRvIII. Methods of determining whether a dosage resulted in the desired result would be evident to one of skill in the art. Administration of one or more chimeric activator can be continuous or intermittent, depending, for example, upon the recipient's physiological condition, whether the purpose of the administration is therapeutic or prophylactic, and other factors known to skilled practitioners. The administration of a chimeric activator may be essentially continuous over a preselected period of time or may be in a series of spaced dose, e.g., either before, during, or after developing a target disease or disorder.

As used herein, the term "treating" refers to the administration of a composition including a fusion protein as described herein to an individual, who has a cancer, a symptom of cancer, or a risk of developing cancer, with the purpose to cure, heal, alleviate, relieve, alter, remedy, ameliorate, improve, or affect the disease, a symptom, or the risk of developing cancer.

Alleviating a disease/disorder, such as cancer, includes delaying the development or progression of the disease, or reducing disease severity. Alleviating the disease does not necessarily require curative results. As used therein, "delaying" the development of a target disease or disorder means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a target disease or disorder includes initial onset and/or recurrence.

In some embodiments, the fusion protein described herein is administered to a subject in need of the treatment at an amount sufficient to inhibit the activity of one or both of the target antigens by at least 20% (e.g., 30%, 40%, 50%, 60%, 70%, 80%, 90% or greater) in vivo. In other embodiments, the fusion protein is administered in an amount effective in reducing the level of one or both target antigens by at least 20% (e.g., 30%, 40%, 50%, 60%, 70%, 80%, 90% or greater).

The fusion proteins or nucleic acids encoding the fusion proteins may be delivered using gene delivery vehicles. The gene delivery vehicle can be of viral or non-viral origin (see generally, Jolly, Cancer Gene Therapy (1994) 1:51; Kimura, Human Gene Therapy (1994) 5:845; Connelly, Human Gene Therapy (1995) 1:185; and Kaplitt, Nature Genetics (1994) 6:148). Expression of such coding sequences can be induced using endogenous mammalian or heterologous promoters and/or enhancers. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther. (1992) 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther. (1992) 3:147); ligand-linked DNA (see, e.g., Wu, J. Biol. Chem. (1989) 264: 16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP Patent No. 0524968. Additional approaches are described in Philip, Mol. Cell. Biol. (1994) 14:2411, and in Woffendin, Proc. Natl. Acad. Sci. (1994) 91:1581.

The particular dosage regimen, i.e., dose, timing and repetition, used in the method described herein will depend on the particular subject and that subject's medical history.

In some embodiments, more than one chimeric activator, or a combination of a chimeric activator and another suitable therapeutic agent, may be administered to a subject in need of the treatment. The chimeric activator can also be used in conjunction with other agents that serve to enhance and/or complement the effectiveness of the agents.

Treatment efficacy for a target disease/disorder can be assessed by methods well-known in the art.

Without further elaboration, it is believed that one of skill in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1: Design of Genetic Elements Encoding Fusion Proteins and Insertion Into Expression Vectors The following sequences were generated and inserted into the expression vector pPICZalpha A (Invitrogen/Life Technologies) by a combination of commercial DNA_synthesis (Genscript, Inc.) and standard DNA cloning and assembly techniques. Specifically, the sequences below were placed directly after the sequence . . . AGA GAG GCT GAA GCT (SEQ ID NO: 19), which encodes the amino acids Arg Glu Ala Glu Ala (SEQ ID NO: 20) that are part of the signal sequence that is removed by processing. At the 3' end of the SEQ ID NOs: 2, 6, 8, 9, and 10, the terminal sequence . . . "CAT CAC CAT CAC CAT CAC TAA" (SEQ ID NO: 21) was joined to the sequence "GTTTGTAGCC" (SEQ ID NO: 22) in the vector. Constructions were performed using "Gibson assembly" (Gibson, D. G. "Enzymatic assembly of overlapping DNA fragments" Methods in Enzymology 498: 349362).

The fusion protein MR1-1 IFNa2-1b served as a "wild-type" and was used as a point of comparison for derivatives or variants that had mutations designed to decrease or increase binding to either IFNa receptor 1 (IFNAR1) or IFNa receptor 2 (IFNAR2). The interferon moiety of MR1-1 IFNa2-1b was based on IFNa2a, but was significantly altered to improve its properties. The resulting interferon is distinct in sequence from IFNa2a and from the other human interferons, as well as from interferons from other organisms.

The interferon-a moiety of the MR1-1 IFNa2-1b protein had no mutations for the purpose of reducing IFNa activity, but was re-engineered relative to natural human interferons in the following ways. The mature IFNa moiety consisted of human IFNa2a, but with an insertion of Asp at approximately position 41 in the sequence Glu-Glu-Phe-Gly-Asn-Gln (SEQ ID NO: 23) . . . to yield Glu-Glu-Phe-Gly-Asp-Gly-Asn-Gln (SEQ ID NO: 24). This resulted in a renumbering of the sequence relative to IFNa2a sequence. The sequence of the IFN moiety of MR1-1 IFNa2-1b also contained mutations of Arg23Lys, Leu26Pro, Glu53Gln, Thr54Ala, Pro56Ser, Asp86Glu, Ile104Thr, Gly106Glu, Thr110Glu, Lys117Asn, Arg125Lys, and Lys136Thr. This set of mutations had the effect of enhancing productivity of the fusion protein in *Pichia pastoris*. Production of MR1-1 IFNa2-1b was at least 3-fold greater than production of MR1-1-IFNa2a from *Pichia pastoris*. In addition, a significant fraction of the MR1-1-IFNa2a underwent a cleavage near the C-terminus of the protein that was not observed with the MR1-1 IFNa2-1b protein.

About five independent *P. pastoris* Zeocin-resistant transformants containing plasmids designed to express MR1-1 IFNa2-1b or MR1-1 IFNa2a were tested for their ability to express full-length proteins in small-scale (5 ml) cultures induced with methanol (BMMY medium).

After the transformation and plating on Zeocin plates, colonies were incubated for three days then picked from the plate and re-plated on a raster plate. The same colonies were labeled and grown in YPD Zeocin 200 mcg/mL (30° C.) to make glycerol stocks by adding 500 microliters of 50% glycerol to 1 mL *Pichia* culture and freezing the stocks at −80° C. Each colony was also used to inoculate a 24-well plate to start protein production screening. Typically, 4-6 transformants per construct were analyzed.

Transformants were grown in 1 mL BMGY media overnight at 30° C. at 140 rpm in a 24-well plate sealed with air-pore tape. This allowed sufficient oxygen uptake by the cells. After overnight growth, the plate(s) were centrifuged at 1700 g for 5 minutes. The supernatant was aspirated and replaced by 1 mL BMM+methanol media; cells were resuspended in media. This initiated protein expression, and plates were placed back into the incubator (30° C. with 140 rpm). After 12-16 hours, the plates were centrifuged again at 3000 g for 5-10 minutes. Supernatants were stored and analyzed by SDS-PAGE gel to assess protein expression.

Supernatants were loaded directly into SDS-PAGE gels, and generally, 10 microliters supernatant were mixed with 20 microliters 2× Novex buffer (Invitrogen). Samples were heated to 95° C. for 6 minutes, then loaded onto SDS-PAGE gels with 4-20% acrylamide gradient and run for 55 minutes at a constant current. Gels were stained in Coomassie Fluor Orange™ (Life Technologies) for about 40 minutes and analyzed. The best-expressing colony per construct was selected for further evaluation. However, demonstrable variation in expression levels between colonies was not generally observed, so the improvement in expression of MR1-1 IFNa2-1b relative to MR1-1 IFNa2a was ascribed to changes in the IFNa protein sequence, as the expression plasmids were otherwise identical.

Expression plasmids for mutated derivatives/variants of MR1-1 IFNa2-1b were constructed by standard techniques to introduce the following mutations in the interferon moiety: Leu30Ala, Arg145Ala, His58Ala plus Arg150Ala, and Glu59Ala Met149Ala. The following coding sequences were used to express the corresponding fusion proteins.

```
MR1-1 IFNa 2-1b wt
                                                        (SEQ ID NO: 6)
GAAGTTCAATTGGTTGAGTCTGGTGGAGGTTTGGTTCAACCAGGAGGTTCCTTGAGATTGTC

ATGTAAAGTTTCTGGTTTTACTTTCTCTTCCTATGGAATGTCTTGGGTTAGACAAGCTCCTG

GAAAGGGTTTGGAATGGGTTGCTTCCATCTCAACCGGTGGTTACAACACATATTACGCTGAT

TCCGTTAAAGGTAGATTCACTATCTCCAGAGATAACTCTAAGAACACTTTGTATTTGCAAAT

GAACTCTTTGAGAGCTGAAGATACTGCTGTTTACTATTGTGCGCGCGGTTACTCTCCATATT

CTTACGCTATGGATTATTGGGGTCAAGGTACTACTGTTACTGTTTCTGGTGGAGGTGGAGGT

TCAGGAGGTGGAGGAAGTGGAGGAGGTGGATCAGACATCCAGATGACACAATCACCATCTTC

CTTGTCAGCTTCTGTTGGAGATAGAGTTACTATTACATGTAGAGCTTCCACTGACATCGATA

ACGACATGAATTGGTATCAGCAAAAACCTGGACAGGCGCCAAAGTTGTTGATCTACGAGGGT

AACTCATTGCAATCTGGAGTTCCTTCCAGATTTTCATCTTCCGGTTCCGGAACAGATTTCAC

TTTGACAATCTCTTCCTTGCAGCCAGAAGACTTTGCTACTTATTACTGTTTGCAATCATGGA

ATGTTCCTTTGACATTCGGTCAAGGAACTAAATTGGAGATTAAGGGTGAAGGAGGGTCAGGT

GAAGGTTCCTCCGGTGAGGGTTCCTCATCCGAAGGGGGAGGATCTGAAGGCGGTGGCTCTGA

GGGTGGAGGTTCAGAGGGAGGGTCATGTGACTTGCCTCAAACTCATTCTTTGGGTTCTAGAA

GAACTTTGATGTTGTTGGCTCAAATGAGAAGAATCTCTCCTTTCTCTTGTTTGAAGGACAGA

CATGACTTCGGTTTCCCTCAAGAGGAGTTCGACGGTAACCAATTCCAAAAGGCTCAAGCTAT

CTCTGTCTTGCATGAGATGATCCAACAAATCTTCAACTTGTTCTCTACTAAGGACTCTTCTG

CTGCTTGGGACGAGACTTTGTTGGAGAAGTTCTACACTGAGTTGTACCAACAATTGAACGAC

TTGGAGGCTTGTGTCACTCAAGAGGTCGGTGTCGAGGAGACTCCTTTGATGAACGAGGACTC

TATCTTGGCTGTCAAGAAGTACTTCCAAAGAATCACTTTGTACTTGACTGAGAAGAAGTACT
```

-continued

CTCCTTGTGCTTGGGAGGTCGTCAGAGCTGAGATCATGAGATCTTTCTCTTTGTCTACTAAC
TTGCAAGAGAGATTGAGAAGAAAGGAGCATCACCATCACCATCACTAA

MR1-1 IFNa2-1b L30A
(SEQ ID NO: 7)
GAAGTTCAATTGGTTGAGTCTGGTGGAGGTTTGGTTCAACCAGGAGGTTCCTTGAGATTGTC
ATGTAAAGTTTCTGGTTTTACTTTCTCTTCCTATGGAATGTCTTGGGTTAGACAAGCTCCTG
GAAAGGGTTTGGAATGGGTTGCTTCCATCTCAACCGGTGGTTACAACACATATTACGCTGAT
TCCGTTAAAGGTAGATTCACTATCTCCAGAGATAACTCTAAGAACACTTTGTATTTGCAAAT
GAACTCTTTGAGAGCTGAAGATACTGCTGTTTACTATTGTGCGCGCGGTTACTCTCCATATT
CTTACGCTATGGATTATTGGGGTCAAGGTACTACTGTTACTGTTTCTGGTGGAGGTGGAGGT
TCAGGAGGTGGAGGAAGTGGAGGAGGTGGATCAGACATCCAGATGACACAATCACCATCTTC
CTTGTCAGCTTCTGTTGGAGATAGAGTTACTATTACATGTAGAGCTTCCACTGACATCGATA
ACGACATGAATTGGTATCAGCAAAAACCTGGACAGGCGCCAAAGTTGTTGATCTACGAGGGT
AACTCATTGCAATCTGGAGTTCCTTCCAGATTTTCATCTTCCGGTTCCGGAACAGATTTCAC
TTTGACAATCTCTTCCTTGCAGCCAGAAGACTTTGCTACTTATTACTGTTTGCAATCATGGA
ATGTTCCTTTGACATTCGGTCAAGGAACTAAATTGGAGATTAAGGGTGAAGGAGGGTCAGGT
GAAGGTTCCTCCGGTGAGGGTTCCTCATCCGAAGGGGAGGATCTGAAGGCGGTGGCTCTGA
GGGTGGAGGTTCAGAGGGAGGGTCATGTGACTTGCCTCAAACTCATTCTTTGGGTTCTAGAA
GAACTTTGATGTTGTTGGCTCAAATGAGAAGAATCTCTCCTTTCTCTTGTGCTAAGGACAGA
CATGACTTCGGTTTCCCTCAAGAGGAGTTCGACGGTAACCAATTCCAAAAGGCTCAAGCTAT
CTCTGTCTTGCATGAGATGATCCAACAAATCTTCAACTTGTTCTCTACTAAGGACTCTTCTG
CTGCTTGGGACGAGACTTTGTTGGAGAAGTTCTACACTGAGTTGTACCAACAATTGAACGAC
TTGGAGGCTTGTGTCACTCAAGAGGTCGGTGTCGAGGAGACTCCTTTGATGAACGAGGACTC
TATCTTGGCTGTCAAGAAGTACTTCCAAAGAATCACTTTGTACTTGACTGAGAAGAAGTACT
CTCCTTGTGCTTGGGAGGTCGTCAGAGCTGAGATCATGAGATCTTTCTCTTTGTCTACTAAC
TTGCAAGAGAGAT T GAGAAGAAAGGAGCATCACCATCACCATCACTAA

MR1-1 IFNa 2-1b R145A
(SEQ ID NO: 8)
GAAGTTCAATTGGTTGAGTCTGGTGGAGGTTTGGTTCAACCAGGAGGTTCCTTGAGATTGTC
ATGTAAAGTTTCTGGTTTTACTTTCTCTTCCTATGGAATGTCTTGGGTTAGACAAGCTCCTG
GAAAGGGTTTGGAATGGGTTGCTTCCATCTCAACCGGTGGTTACAACACATATTACGCTGAT
TCCGTTAAAGGTAGATTCACTATCTCCAGAGATAACTCTAAGAACACTTTGTATTTGCAAAT
GAACTCTTTGAGAGCTGAAGATACTGCTGTTTACTATTGTGCGCGCGGTTACTCTCCATATT
CTTACGCTATGGATTATTGGGGTCAAGGTACTACTGTTACTGTTTCTGGTGGAGGTGGAGGT
TCAGGAGGTGGAGGAAGTGGAGGAGGTGGATCAGACATCCAGATGACACAATCACCATCTTC
CTTGTCAGCTTCTGTTGGAGATAGAGTTACTATTACATGTAGAGCTTCCACTGACATCGATA
ACGACATGAATTGGTATCAGCAAAAACCTGGACAGGCGCCAAAGTTGTTGATCTACGAGGGT
AACTCATTGCAATCTGGAGTTCCTTCCAGATTTTCATCTTCCGGTTCCGGAACAGATTTCAC
TTTGACAATCTCTTCCTTGCAGCCAGAAGACTTTGCTACTTATTACTGTTTGCAATCATGGA
ATGTTCCTTTGACATTCGGTCAAGGAACTAAATTGGAGATTAAGGGTGAAGGAGGGTCAGGT
GAAGGTTCCTCCGGTGAGGGTTCCTCATCCGAAGGGGAGGATCTGAAGGCGGTGGCTCTGA
GGGTGGAGGTTCAGAGGGAGGGTCATGTGACTTGCCTCAAACTCATTCTTTGGGTTCTAGAA

-continued

GAACTTTGATGTTGTTGGCTCAAATGAGAAGAATCTCTCCTTTCTCTTGTTTGAAGGACAGA

CATGACTTCGGTTTCCCTCAAGAGGAGTTCGACGGTAACCAATTCCAAAAGGCTCAAGCTAT

CTCTGTCTTGCATGAGATGATCCAACAAATCTTCAACTTGTTCTCTACTAAGGACTCTTCTG

CTGCTTGGGACGAGACTTTGTTGGAGAAGTTCTACACTGAGTTGTACCAACAATTGAACGAC

TTGGAGGCTTGTGTCACTCAAGAGGTCGGTGTCGAGGAGACTCCTTTGATGAACGAGGACTC

TATCTTGGCTGTCAAGAAGTACTTCCAAAGAATCACTTTGTACTTGACTGAGAAGAAGTACT

CTCCTTGTGCTTGGGAGGTCGTCGCTGCTGAGATCATGAGATCTTTCTCTTTGTCTACTAAC

TTGCAAGAGAGATTGAGAAGAAAGGAGCATCACCATCACCATCACTAA

MR1-1 IFNa 2-1b E59A M149A (SEQ ID NO: 9)
GAAGTTCAATTGGTTGAGTCTGGTGGAGGTTTGGTTCAACCAGGAGGTTCCTTGAGATTGTC

ATGTAAAGTTTCTGGTTTTACTTTCTCTTCCTATGGAATGTCTTGGGTTAGACAAGCTCCTG

GAAAGGGTTTGGAATGGGTTGCTTCCATCTCAACCGGTGGTTACAACACATATTACGCTGAT

TCCGTTAAAGGTAGATTCACTATCTCCAGAGATAACTCTAAGAACACTTTGTATTTGCAAAT

GAACTCTTTGAGAGCTGAAGATACTGCTGTTTACTATTGTGCGCGCGGTTACTCTCCATATT

CTTACGCTATGGATTATTGGGGTCAAGGTACTACTGTTACTGTTTCTGGTGGAGGTGGAGGT

TCAGGAGGTGGAGGAAGTGGAGGAGGTGGATCAGACATCCAGATGACACAATCACCATCTTC

CTTGTCAGCTTCTGTTGGAGATAGAGTTACTATTACATGTAGAGCTTCCACTGACATCGATA

ACGACATGAATTGGTATCAGCAAAAACCTGGACAGGCGCCAAAGTTGTTGATCTACGAGGGT

AACTCATTGCAATCTGGAGTTCCTTCCAGATTTTCATCTTCCGGTTCCGGAACAGATTTCAC

TTTGACAATCTCTTCCTTGCAGCCAGAAGACTTTGCTACTTATTACTGTTTGCAA

TCATGGA ATGTTCCTT TGACATTCGGTCAAGGAACTAAAT TGGAGAT

TAAGGGTGAAGGAGGGTCAGGT

GAAGGTTCCTCCGGTGAGGGTTCCTCATCCGAAGGGGGAGGATCTGAAGGCGGTGGCTCTGA

GGGTGGAGGTTCAGAGGGAGGGTCATGTGACTTGCCTCAAACTCATTCTTTGGGTTCTAGAA

GAACTTTGATGTTGTTGGCTCAAATGAGAAGAATCTCTCCTTTCTCTTGTTTGAAGGACAGA

CATGACTTCGGTTTCCCTCAAGAGGAGTTCGACGGTAACCAATTCCAAAAGGCTCAAGCTAT

CTCTGTCTTGCATGCGATGATCCAACAAATCTTCAACTTGTTCTCTACTAAGGACTCTTCTG

CTGCTTGGGACGAGACT T

TGTTGGAGAAGTTCTACACTGAGTTGTACCAACAATTGAACGAC

TTGGAGGCTTGTGTCACTCAAGAGGTCGGTGTCGAGGAGACTCCTTTGATGAACGAGGACTC

TATCTTGGCTGTCAAGAAGTACTTCCAAAGAATCACTTTGTACTTGACTGAGAAGAAGTACT

CTCCTTGTGCTTGGGAGGTCGTCAGAGCTGAGATCGCGAGATCTTTCTCTTTGTCTACTAAC

TTGCAAGAGAGATTGAGAAGAAAGGAGCATCACCATCACCATCACTAA

MR1-1 IFNa 2-1b H58A R150A (SEQ ID NO: 10)
GAAGTTCAATTGGTTGAGTCTGGTGGAGGTTTGGTTCAACCAGGAGGTTCCTTGAGATTGTC

ATGTAAAGTTTCTGGTTTTACTTTCTCTTCCTATGGAATGTCTTGGGTTAGACAAGCTCCTG

GAAAGGGTTTGGAATGGGTTGCTTCCATCTCAACCGGTGGTTACAACACATATTACGCTGAT

TCCGTTAAAGGTAGATTCACTATCTCCAGAGATAACTCTA

```
-continued
CACCATCTTC CT TGTCAGCT TCTGTTGGAGATAGAGTTACTAT

TACATGTAGAGCTTCCACTGACATCGATA

ACGACATGAATTGGTATCAGCAAAAACCTGGACAGGCGCCAAAGTTGTTGATCTACGAGGGT

AACTCATTGCAATCTGGAGTTCCTTCCAGATTTTCATCTTCCGGTTCCGGAACAGATTTCAC

TTTGACAATCTCTTCCTTGCAGCCAGAAGACTTTGCTACTTATTACTGTTTGCAATCATGGA

ATGTTCCTTTGACATTCGGTCAAGGAACTAAATTGGAGATTAAGGGTGAAGGAGGGTCAGGT

GAAGGTTCCTCCGGTGAGGGTTCCTCATCCGAAGGGGAGGATCTGAAGGCGGTGGCTCTGA

GGGTGGAGGTTCAGAGGGAGGGTCATGTGACTTGCCTCAAACTCATTCTTTGGGTTCTAGAA

GAACTTTGATGTTGTTGGCTCAAATGAGAAGAATCTCTCCTTTCTCTTGTTTGAAGGACAG

A CATGACTTCGGTTTCCCTCAAGAGGAGTTCGACGGTAACCAATTCCAAAAGGCTCAAGCTAT

CTCTGTCTTGGCTGAGATGATCCAACAAATCTTCAACTTGTTCTCTACTAAGGACTCTTCTG

CTGCTTGGGACGAGACTTTGTTGGAGAAGTTCTACACTGAGTTGTACCAACAATTGAACGAC

TTGGAGGCTTGTGTCACTCAAGAGGTCGGTGTCGAGGAGACTCCTTTGATGAACGAGGACTC

TATCTTGGCTGTCAAGAAGTACTTCCAAAGAATCACTTTGTACTTGACTGAGAAGAAGTACT

CTCCTTGTGCTTGGGAGGTCGTCAGAGCTGAGATCATGGCATCTTTCTCTTTGTCTACTAAC

TTGCAAGAGAGAT T GAGAAGAAAGGAGCATCACCATCACCATCACTAA
```

Example 2: Expression and Activity Testing of Unpurified Protein From Culture Supernatants The production and cell-based testing of the fusion proteins were performed as follows. *Pichia pastoris* strains were engineered with expression vectors based on the plasmid pPTCz-alpha, using the various coding sequences presented herein. Standard procedures were used in the plasmid construction and integration into *Pichia*. Proteins were expressed following in *Pichia pastoris* following the instructions in the "EasySelect™ *Pichia* Expression supplied by Invitrogen/Life Technologies. BMMY medium was used for expression, as it was found to reduce proteolysis of the desired products. Production was generally in the range of about 10 micrograms of MR1-1-linker-IFNa per ml of *Pichia* culture supernatant. This fusion protein was the major protein in culture supernatant.

Expression of MR1-1-linker-human IFN-a2 was compared with the MR1-1-linker-human IFN-a2-1b protein to test for the effects of the mutation of several amino acids relative to IFNa2. It was found that the fusion protein containing IFN a2-1b was produced with much less proteolysis than a corresponding fusion protein with IFNa2.

The various proteins were obtained from culture supernatant by centrifugal removal of the cells, filtration of the supernatant through a 0.2 micron filter to remove remaining cells and sterilize the preparation, concentration, and buffer exchange into Dulbecco's modified Eagle's medium. Serial 10-fold dilutions of the protein in this foul' was added to wells containing either U87MG glioblastoma cells or U87MG cells expressing EGFRvIII, from about $10^{-6}$ to $10^{12}$M. Cells were plated at about 10,000 cells per well in a 96-well plate and incubated for 70 hours at 37° C., 5% $CO_2$, in high-glucose DMEM with 10% FBS and PenStrep (100 IU penicillin and 100 "g/ml streptomycin). Cell number was then measured using the WST-1 reagent (Roche).

During the 70-hour incubation, cell number appeared to increase about 2.5-fold. For each series shown in FIGS. 5A-5F, readings were normalized to the readings with no added fusion protein. Maximal readings were therefore about 1, minimal readings were about 0.4, and thus an IC50 could be calculated as the concentration of fusion protein giving a normalized reading of about 0.7. Based on this calculation approach, it can be seen that the various fusion proteins show a significant targeting effect, with much greater activity on U87MG-EGFRvIII cells than on U87MG cells. In particular, MR1-1-IFNa2-1b("wild-type"), MR1-1-IFNa2-1b(Arg145A1a), and MR1-1-IFNa2-1b(Glu59Ala Met149A1a) showed respectively about 200-fold, 1000-fold, and at least 1,000-fold specificity for the EGFRvIII-expressing cells. This level of cell-type specificity is much greater than that observed in previous studies of targeted, mutated IFNa fusion proteins, as described in Cironi et al. (J Biol Chem [2008] 283(13):8469-76), and indicates that the further conceptual advances herein are useful in enhancing cell type-specific action of fusion proteins.

Fusion proteins bearing the IFNa L30A mutation or the IFNa His58Ala+Arg1 50Ala mutations did not show complete inhibition of proliferation even at the highest concentration tested. Use of these mutations is thus less preferred.

It is noteworthy that "wild-type" IFNa2-1b showed a significant targeting effect. This was not expected based on previous work. Without wishing to be bound by theory, it may be that the negatively charged linker attached to IFNa2-1b effectively reduces the binding of IFNa2-1b to its receptor. Comparison of the effect of IFNa2-1b and MR1-1-linker-IFNa2-1b on U87MG cells without EGFRvIII shows an IC50 about $10^{-11}$M and $10^{-1°}$M respectively. It may be that the negatively charged linker interacts with the positively charged receptor-binding surface of IFNa2-1 b, effectively reducing its on-rate in a manner analogous to a mutation on this surface; according to this hypothesis, only a subset of molecules in which the linker is not interacting with IFNa2-1b would be competent to bind. Thus, in some embodiments, the introduction of negative charges into a linker in an <antibody V region>-<linker>-<positively charged signaling moiety> is beneficial.

Example 3: Scaled-Up Purification of a Novel AIR1-1-IFNalpha Fusion Protein

The fusion protein MR1-1-IFNa2-1b(R145A) was purified from engineered *Pichia pastoris* as follows. Many aspects of this procedure followed the protocols given in manual for the EasySelect™ *Pichia* Expression Kit from Invitrogen (Catalogue number K1740-01; Manual part number 25-0172), which defines formulas for the media used. The *P. pastoris* strain was grown to saturation in about 1 liter of BMGY medium, then centrifuged and resuspended in 2.4 liters of BMMY at a final OD of 0.5, distributed into 10 two-liter Erlenmeyer flasks, and incubated for 48 hours at 30° C. with shaking at about 200 rpm and "Airport" air-permeable seals on the top of the flasks. Cultures were then centrifuged at 10,000× gravity for about 15 minutes, the supernatant harvested, filtered using (0.22 um) filters, and transferred to a cold room. About 277 grams of $(NH_4)_2SO_4$ was added per liter and dissolved with agitation. This solution was incubated for 16 hours with gentle agitation, harvested by centrifugation in 400 ml tubes at 20,000× gravity, then resuspended in HisTALON™ equilibration buffer (buffer kit catalog number 635651) in preparation for purification based on cobalt affinity.

About 5 mls of TALON metal affinity resin was used for purification in accordance with the manufacturer's instructions (Manual part number PT1320-1). The protein was eluted in about 15 mls of HisTALON elution buffer, filter-sterilized, and further purified by FPLC. FIG. 2 shows a typical SDS-PAGE in which the purified protein is quantitated by comparison with a bovine serum albumin standard. The final concentration was about 500 mcg/ml by this measurement.

Example 4: Activity of Purified Fusion Proteins on Diverse Mammalian Cells

The purified MR1-1-IFNa2-1b(R145A) protein from Example 3 was tested for growth-inhibitory activity on U87MG glioblastoma cells or U87MG cells expressing EGFRvIII. Cell culture and assay procedures were essentially identical to those described in Example 2. It was found that the ratio of IC5Os for MR1-1-IFNalpha2-1b(R145A)/IFNalpha2 was about 18 on U87MG cells, but was about 0.122 on U87MG-EGFRvIII cells, indicating a net targeting effect of about 148-fold.

A preparation of MR1-1-IFNa2-1b that had been purified by His6-metal affinity was tested for growth-inhibition of mouse Neuro 2a cells (N2a cells). It was found that MR1-1-IFNa2-1b inhibited growth of the mouse cells, although the IC50 for inhibition was about 50-fold greater than for murine IFNa2. Human IFNa2a had no detectable inhibitory activity against the mouse cells. These results are depicted in FIG. 8.

The activity against mouse cells is a valuable feature because human interferons generally do not activate mouse interferon receptors, which precludes biological testing of human interferons in natural mouse experimental systems during the drug-development process.

Example 5. Toxicity and Pharmacokinetic Testing of Purified Fusion Proteins

The protein MR1-1-IFNa2-1b(R145A) was purified as described in Example 3 and tested for potential toxic effects in mice as follows. About 100 micrograms of MR1-1-IFNa2-1b(R145A) protein in the physiologically acceptable carrier phosphate-buffered saline was injected intraperitoneally into C57BL6 mice 5 days in a row (100 mcg/day). Three female mice were injected with the protein and two were injected with the PBS vehicle; all were maintained as littermates. The mice were observed daily during the injection series and three days afterwards for signs of toxicity including death or distress indicators such as decreased activity, lethargy, decreased appetite, weight loss, poor body condition, abnormal or hunched body posture, poor grooming, respiratory distress, eye squinting, nose bulge, ear position and/or whisker changes. All of the mice survived and no signs of toxicity were observed in the animals that received the MR1-1-IFNa2-1b(R145A) protein.

The protein MR1-1-IFNa2-1b(no mutation) and MR1-1-IFNa2-1b with a mutation in the MR1-1 scFv (VH Ser52Arg, designed to block antigen binding) were purified as described in Example 3 and tested for their pharmacokinetic profile in mice as follows. About 12.5 micrograms of each fusion protein in phosphate-buffered saline was injected intravenously into the tail vein of C57BL/6 mice (N=3 per dose group). Blood samples were withdrawn at 0, 1, 3, 7 and 24 hours, and the concentration of MR1-1-IFNa fusion proteins was determined by a standard ELISA-type assay. Based on a comparison of the 7-hour and 24-hour timepoints, the terminal serum half-lives of the MR1-1-IFNa2-1b(no mutation) and MR1-1-IFNa2-1b (mutant V region) fusion proteins were about 3 hours and 4 hours, respectively.

Example 6: Activity of Purified Fusion Proteins in an Immunosuppressed Tumor Model To test the effect of the MR1-1-IFNa2-1b(R145A) protein on tumors in a mouse model, about 1 million oncogenic murine neural stem cells in approximately 30% Matrigel (1:2.5 mixture Matrigel and PBS) were injected into the flanks of Nude C57Bl/6 mice and allowed to foiui small tumors. The cells contained a knockout of the $p16^{INK4a}$ gene and express EGFRvIII from a transgene (Bachoo et al. [2002] Cancer Cell 1:269-277). Six mice per dose group were used. When the average tumor size was about 100 $mm^3$, the mice were divided into two groups with equal average tumor sizes. One group was injected intraperitoneally daily for 5 days with about 100 micrograms of MR1-1-IFNa2-1b(R145A) (135 mcg/mouse/day; 150 microliters× 0.9 mg/mL protein per mouse per day), while the other was injected intraperitoneally with a PBS vehicle control.

The following results were observed. There was a statistically significant difference in the growth rate of the tumors between the two groups of mice, with the treated mice showing a cessation of tumor growth for about 1 week. Specifically, the tumor sizes in the mice that received the fusion proteins were identical to the tumor sizes in mice that received the control on days 1 and 3. On day 5 the tumors in the treated group of mice showed essentially no increase in size while the tumors in the untreated group of mice showed about a 50% increase. On all subsequent days the tumors in the treated mice were, on average, smaller than the tumors in the untreated mice. Between days 7 and 9, tumor growth in the treated mice was observed to resume, possibly because the fusion protein had been cleared from the mouse and no long-term immune response was possible because the mice are Nude mice with a defective immune system. FIG. 9.

To further test the effect of the MR1-1-IFNa2-1b(R145A) protein on tumors in a mouse model, about 1 to 5 million U87MG-EGFRvIII cells in about 30% Matrigel are injected into the flanks of Nude C57Bl/6 mice and allowed to form small tumors. Six mice per dose group are used. When the average tumor size is about 100 mm$^3$, the mice are divided into groups with equal average tumor sizes. One group was injected daily for 5 days with about 100 micrograms of MR1-1-IFNa2-1b(R145A); another group was injected with MR1-1-IFNa2-1b (no mutation); another group wass injected with MR1-1-IFNa2-1b(E59A M149A); and the final group was injected with a PBS vehicle control.

There was a statistically significant difference in the growth rate of the tumors between the control mice and the mice that had been treated with the fusion proteins, with the treated mice showing less dramatic growth and in some cases tumor shrinkage.

Example 7: Activity of Purified Fusion Proteins in a Syngeneic Tumor Model

To test the effect of the fusion protein MR1-1-IFNa2-1b (R145A) on tumors in an immunocompetent mouse model, about 1 million oncogenic murine neural stem cells in 30% Matrigel were injected into the flanks of wild-type C57Bl/6 mice and were allowed to form small tumors. The cells contained a knockout of the $^{p16INK4a}$ gene and expressed EGFRvIII from a transgene (Bachoo et al. [2002] Cancer Cell 1:269-277). About six mice per dose group were used. When the average tumor size was about 100 mm$^3$, the mice were divided into two groups with equal average tumor sizes. One group was injected daily for 5 days with about 100 micrograms of MR1-1-IFNa2-1b (R145A). A second group was injected with MR1-1-IFNa2-1b(no mutation). A third group was injected with a PBS vehicle control.

There was a statistically significant difference in the growth rate of the tumors between the treated groups of mice and the PBS-injected control mice, with the treated mice showing less dramatic growth and in some cases tumor shrinkage.

Example 8: Treatment of Human Patients With a Fusion Protein

A human patient with glioblastoma multiforme is treated with a fusion protein as described herein, such as the MR1-1-IFNa2-1b(R145A) fusion protein.

The patient may be optionally tested to verify that his or her tumor cells express the EGFRvIII protein. Several diagnostic approaches are possible, but two general approaches are based on the presence of the tumor nucleic acid or protein. The EGFRvIII protein is expressed as a result of a deletion of exons 2 through 7 of the EGFR gene, resulting in exon 1 being spliced directly to exon 8. Because of this, the tumor cells express a novel genomic DNA segment that can be detected by PCR of tumor genomic DNA using primers that correspond to segments from exon 1 and exon 8. DNA from normal tissue (that does not encode the EGFRvIII variant) will generally not be amplified because when all the exons are present, the distance between exon 1 and 8 is too large for efficient amplification under standard conditions. Similarly, mRNA from a tumor sample may be isolated and characterized by reverse transcriptase-PCR (RT-PCR) using primers corresponding to exon 1 and exon 8 or a downstream exon. In this case, the PCR products will typically include a signal from an intact EGFR mRNA that is present in normal cells that may derive from tumor heterozygosity, normal adjacent tissue or normal cells that are part of the tumor such as stromal cells, fibroblasts, etc., but presence of EGFRvIII mRNA will generate a distinct product that is smaller by 801 base pairs. The presence of such smaller products is diagnostic of an EGFRvIII-type deletions/variants.

A patient's tumor may also be characterized by detection of the EGFRvIII protein, such as by antibody-based detection. For example, a tumor sample may be fixed and stained with an antibody that recognizes the EGFRvIII protein. For example, the variable regions or CDRs of the scFv MR1-1 V may be configured into a full length antibody with murine IgG constant regions and used as a primary antibody. Probing with a EGFRvIII specific primary antibody can be followed by a secondary antibody directed to the murine IgG constant regions and conjugated to a histochemically detectable enzyme, such as horseradish peroxidase. Alternatively, protein may be extracted from a tumor or tumor cells and analyzed by Western blot or ELISA assay using MR1-1 V regions to detect the EGFRvIII protein. In one treatment paradigm, a patient is first treated with surgery, followed by a combination of radiation therapy and temozolomide. The radiation and temozolomide are administered according to standard practice and the judgement of a physician, with a total dose of roughly 60 Gy (Grays) or more delivered in doses of 1.8 to 2 Gy per day, 5 days a week, and temozolomide delivered intravenously over 90 minutes in doses of 75 mg/m$^2$. The MR1-1-IFNa2-1b(R145A) fusion protein is administered upon cessation of temozolomide treatment due to failure of treatment or unacceptable side effects. Typical profiles for cessation of temozolomide would be a tumor volume of >0.5 cm$^3$ but <1.5 cm$^3$ and a platelet count of <100,000/mm$^3$, and a CTC grade 2 non-hematologic toxicity; or a tumor volume of <0.5 cm$^3$ and a platelet count of <10,000/mm$^3$, and a CTC grade 3 or 4 non-hematologic toxicity.

The fusion protein is administered intravenously in an appropriate solution such as 5% dextrose over 1 to 4 hours. The dose is about 5 mcg to 3 mg or more per week, e.g., 25 mcg to 625 mcg per week; or about 125 mcg/week, with administrations between 3 to 5 times per week. The patient is monitored for fever and other side effects. Without wishing to be bound by theory, the cessation of temozolomide results in enhanced survival of leukocytes that promote the activity of the MR1-1-IFNa2-1b(R145A) fusion protein.

In a second treatment paradigm, a patient is first treated with surgery, followed by a combination of radiation therapy, temozolomide, and MR1-1-IFNa2-1b(R145A) fusion protein. The radiation and temozolomide are administered essentially as described above.

The fusion protein is administered intravenously in an appropriate solution such as 5% dextrose over 1 to 4 hours. The dose is about 5 mcg to 3 mg or more per week, e.g., 25 mcg to 625 mcg per week or about 125 mcg/week, with administrations between 3 to 5 times per week. The patient is monitored for fever and other side effects. Without wishing to be bound by theory, the combination of DNA damage in tumor cells resulting from radiation plus temozolomide and the targeting of IFNa activity on these cells is synergistic, results in enhanced killing of the tumor cells in the patient.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature discloses is only an example of a generic series of equivalent or similar features.

From the above description, one of skill in the art can easily ascertain the essential characteristics of the present disclosure, and without departing from the spirit and scope thereof, can make various changes and modification of the disclosure to adapt it to various usages and conditions. Thus, other embodiments are also within the claims.

What is claimed herein is:

1. A fusion protein comprising
   a Type 1 interferon protein domain comprising the sequence of SEQ ID NO: 18 or a sequence with one or two mutations relative to SEQ ID NO:18, the mutations selected from the group consisting of:
   L30A, R145A, M149A, E59A, H58A, and R150A;
   an antibody variable region element comprising
      a HCDR1 comprising amino acids 31-35 of SEQ ID NO: 15;
      a HCDR2 comprising amino acids 50-65 of SEQ ID NO: 15;
      a HCDR3 comprising amino acids 95-102 of SEQ ID NO: 15;
      a LCDR1 comprising amino acids 24-34 of SEQ ID NO: 16;
      a LCDR2 comprising amino acids 50-56 of SEQ ID NO: 16; and
      a LCDR3 comprising amino acids 89-97 of SEQ ID NO: 16;
      and which binds to EGFRvIII; and
   a linker that connects the protein domain and the antibody variable region element.

2. The fusion protein of claim 1, wherein the fusion protein comprises one polypeptide chain.

3. The fusion protein of claim 1, wherein the Type 1 interferon protein domain comprises mutations H58A and R150A.

4. The fusion protein of claim 1, wherein the Type 1 interferon comprises mutations E59A and M149A.

5. The fusion protein of claim 1, wherein the linker connects the C-terminal end of the antibody variable region element to the N-terminal end of the protein domain.

6. The fusion protein of claim 1, wherein the linker connects the C-terminal end of the protein domain to the N-terminal end of the antibody or antibody variable region element.

7. The fusion protein of claim 1, wherein the linker is a peptide linker and has a net charge.

8. The fusion protein of claim 1, wherein the net charge of the linker is negative.

9. The fusion protein of claim 1, wherein the net charge of the linker is positive.

10. The fusion protein of claim 8, wherein the linker comprises amino acids selected from the group consisting of glycine, serine, glutamate, and aspartate.

11. The fusion protein of claim 9, wherein the linker comprises amino acids selected from the group consisting of lysine, arginine, and histidine.

* * * * *